(12) United States Patent  (10) Patent No.: US 8,728,498 B2
Zhang et al.  (45) Date of Patent: May 20, 2014

(54) ELECTROSPUN SILK MATERIAL SYSTEMS FOR WOUND HEALING

(75) Inventors: Xiaohui Zhang, Westmont, IL (US); David L. Kaplan, Concord, MA (US); Scott E. Wharram, Pepperell, MA (US); Stephen McCarthy, Tyngsboro, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 13/382,967

(22) PCT Filed: Jul. 14, 2010

(86) PCT No.: PCT/US2010/041953
§ 371 (c)(1),
(2), (4) Date: Mar. 21, 2012

(87) PCT Pub. No.: WO2011/008842
PCT Pub. Date: Jan. 20, 2011

(65) Prior Publication Data
US 2012/0171256 A1  Jul. 5, 2012

Related U.S. Application Data

(60) Provisional application No. 61/225,335, filed on Jul. 14, 2009.

(51) Int. Cl.
*A61K 9/00* (2006.01)
*A61F 13/00* (2006.01)
*A61K 9/70* (2006.01)

(52) U.S. Cl.
USPC .......................................... 424/400; 424/443

(58) Field of Classification Search
None
See application file for complete search history.

(56) References Cited

U.S. PATENT DOCUMENTS

| 1,989,005 | A | 1/1935 | Fink et al. |
| 4,233,212 | A | 11/1980 | Otoi et al. |
| 4,820,418 | A | 4/1989 | Hirotsu et al. |
| 5,047,507 | A | 9/1991 | Buchegger et al. |

(Continued)

FOREIGN PATENT DOCUMENTS

| CA | 2405850 | 10/2002 |
| EP | 1440088 | 7/2004 |

(Continued)

OTHER PUBLICATIONS

Agarwal et al., J. Appl. Polym. Sci., 63:401-410 (1997). "Effect of Moisture Absorption on the Thermal Properties of *Bombyx mori* Silk Fibroin Films.".

(Continued)

*Primary Examiner* — Carlos Azpuru
*Assistant Examiner* — Casey Hagopian
(74) *Attorney, Agent, or Firm* — Choate, Hall & Stewart, LLP

(57) ABSTRACT

The present invention relates to the processes of preparing silkfibroin/polyethylene oxide blended materials, and the resulting materials thereof, which are suitable for biomedical applications such as wound healing. In particular, the electrospun silk fibroin/PEO mats with a silk:PEO blend ratio of 2:1 to 4:1, treated with controlled evaporation, constraint-drying techniques, and/or alcohol treatment, and/or PEO extraction, demonstrate suitable physical and biofunctional properties, such as fiber structure, topography, absorption, water vapor transmission rates, oxygen permeation, and biodegradability, relevant to biomaterial systems with utility for wound dressings.

22 Claims, 26 Drawing Sheets

(56) References Cited

U.S. PATENT DOCUMENTS

| | | |
|---|---|---|
| 5,290,494 A | 3/1994 | Coombes et al. |
| 5,606,019 A | 2/1997 | Cappello |
| 5,728,810 A | 3/1998 | Lewis et al. |
| 5,770,193 A | 6/1998 | Vacanti et al. |
| 5,994,099 A | 11/1999 | Lewis et al. |
| 6,110,590 A | 8/2000 | Zarkoob et al. |
| 6,123,819 A | 9/2000 | Peeters |
| 6,175,053 B1 | 1/2001 | Tsubouchi |
| 6,592,623 B1 | 7/2003 | Bowlin et al. |
| 6,815,427 B2 | 11/2004 | Tsubouchi et al. |
| 6,902,932 B2 | 6/2005 | Altman et al. |
| 7,041,797 B2 | 5/2006 | Vollrath |
| 7,057,023 B2 | 6/2006 | Islam et al. |
| 7,285,637 B2 | 10/2007 | Armato et al. |
| 7,635,755 B2 | 12/2009 | Kaplan et al. |
| 7,662,409 B2 | 2/2010 | Masters |
| 7,674,882 B2 | 3/2010 | Kaplan et al. |
| 7,727,575 B2 | 6/2010 | Kaplan et al. |
| 7,842,780 B2 | 11/2010 | Kaplan et al. |
| 7,960,509 B2 | 6/2011 | Kaplan et al. |
| 8,071,722 B2 | 12/2011 | Kaplan et al. |
| 2002/0028243 A1 | 3/2002 | Masters |
| 2003/0007991 A1 | 1/2003 | Masters |
| 2003/0099630 A1 | 5/2003 | DiBenedetto et al. |
| 2003/0183978 A1 | 10/2003 | Asakura |
| 2004/0005363 A1 | 1/2004 | Tsukada et al. |
| 2004/0266992 A1 | 12/2004 | Migliaresi et al. |
| 2005/0260706 A1 | 11/2005 | Kaplan et al. |
| 2007/0187862 A1* | 8/2007 | Kaplan et al. ............ 264/172.11 |
| 2007/0212730 A1 | 9/2007 | Vepari et al. |
| 2008/0085272 A1 | 4/2008 | Kaplan et al. |
| 2008/0249452 A1 | 10/2008 | Tanaka et al. |
| 2008/0293919 A1 | 11/2008 | Kaplan et al. |
| 2009/0202614 A1 | 8/2009 | Kaplan et al. |
| 2009/0232963 A1 | 9/2009 | Kaplan et al. |
| 2009/0234026 A1 | 9/2009 | Kaplan et al. |
| 2010/0028451 A1 | 2/2010 | Kaplan et al. |
| 2010/0046902 A1 | 2/2010 | Kaplan et al. |
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2011/0046686 A1 | 2/2011 | Kaplan et al. |
| 2011/0076384 A1 | 3/2011 | Cannizzaro et al. |
| 2011/0135697 A1 | 6/2011 | Omenetto et al. |
| 2011/0152214 A1 | 6/2011 | Boison et al. |
| 2011/0171239 A1 | 7/2011 | Kaplan et al. |
| 2012/0121820 A1 | 5/2012 | Kaplan et al. |
| 2012/0123519 A1 | 5/2012 | Lovett et al. |

FOREIGN PATENT DOCUMENTS

| | | |
|---|---|---|
| GB | 1182153 | 2/1970 |
| JP | 55-139427 | 10/1980 |
| JP | 60-142259 | 7/1985 |
| JP | 60-259677 | 12/1985 |
| JP | 01118544 | 11/1989 |
| JP | 06-346314 | 12/1994 |
| JP | 08-295697 | 11/1996 |
| JP | 10-36676 | 2/1998 |
| JP | 2000-273264 | 10/2000 |
| JP | 2003192807 | 7/2003 |
| JP | 2004068161 | 3/2004 |
| WO | 99/01089 | 1/1999 |
| WO | 01/36531 | 5/2001 |
| WO | 01/56626 | 8/2001 |
| WO | 02/072931 | 9/2002 |
| WO | 03/022909 | 3/2003 |
| WO | 03/038033 | 5/2003 |
| WO | 2004/000915 | 12/2003 |
| WO | 2004/041845 | 5/2004 |
| WO | 2005/123114 | 12/2005 |
| WO | 2008/127405 | 10/2008 |
| WO | 2011/006133 | 1/2011 |

OTHER PUBLICATIONS

Fridrikh et al., Physical Review Letters, 90(14):144502-144506 (2003). "Controlling the Fiber Diameter during Electrospinning.".

Hu et al., Macromolecules, 39:6161-6170 (2006). "Determining Beta-Sheet Crystallinity in Fibrous Proteins by Thermal Analysis and Infrared Spectroscopy.".

Jin et al., Advanced Functional Materials, 15:1241-1247 (2005). "Water-Stable Silk Films with Reduced β-Sheet Content.".

Kowalewski et al., Bulletin of the Polish Academy of Sciences, 53(4):385-394 (2005). "Experiments and modelling of electrospinning process.".

Lawrence et al., J. Mater. Sci 43:6967-6985 (2008). "Processing methods to control silk fibroin film biomaterial features.".

Liu et al., Biomacromolecules, 9:116-121 (2008). "Proline and Processing of Spider Silks.".

Mi et al., Biomaterials, 22:165-173 (2001). "Fabrication and characterization of a sponge-like asymmetric chitosan membrane as a wound dressing.".

Mi et al., J. Biomed. Mat. Res. 59:438-439 (2002). "Control of wound infections using a bilayer chitosan wound dressing with sustainable antibiotic delivery.".

Reneker, et al., Polymer, 49:2387-2425 (2008). "Electrospinning jets and polymer nanofibers.".

Sugihara et al., Exp. Biol. Med., 225:58-64 (2000). "Promotive Effects of a Silk Film on Epidermal Recovery from Full-Thickness Skin Wounds.".

Tanaka et al., Insect Biochemistry and Molecular Biology 29:269-276 (1999). "Hydrophobic interaction of P25, containing Asn-linked oligosaccharide chains, with the H-L complex of silk fibroin produced by *Bombyx mori*.".

Van Der Heijden et al., Thermochimica Acta 378:27-34 (2001). "Phase behavior of polymer-diluent systems characterized by temperature modulated differential scanning calorimetry".

Vepari et al., Progress in Polymer Science, 32:991-1007 (2007). "Silk as a biomaterial.".

Wang et al., Macromolecules, 37:6856-6864 (2004). "Mechanical Properties of Electrospun Silk Fibers.".

Wang et al., Macromolecules, 39:1102-1107 (2006). "Production of Submicron Diameter Silk Fibers under Benign Processing Conditions by Two-Fluid Electrospinning.".

Wong et al., Appl. Phys. A-Mater 82:193-203 (2006). "Solution behavior of synthetic silk peptides and modified recombinant silk proteins.".

Zhou et al., Nucleic Acids Research 28(12):2413-2419 (2000). "Fine organization of *Bombyx mori* fibroin heavy chain gene.".

Asakura et al., Journal of Membrane Science, 59:39-52 (1991). "Porous membrane of *Bombyx mori* silk fibroin: structure characterization, physical properties and application to glucose oxidase immobilization.".

Asakura et al., Macromolecules, 17:1075-1081 (1984). "NMR of silk fibroin 2. 13C NMR study of the chain dynamics and solution structure of *Bombyx mori* silk fibroin.".

Asakura et al., Macromolecules, 18:1841-1845 (1985). "Conformational characterization of *B. mori* silk fibroin in the solid state by high-frequency 13C cross polarization-magic angel spinning NMR, X-ray diffraction and infrared spectroscopy.".

Chen et al., J Appl Polymer Sci, 65:2257-2262 (1997). "pH sensitivity and ion sensitivity of hydrogels based on complex-forming chitosan/silk fibroin interpenetrating polymer network.".

Chen et al., J Appl Polymer Sci, 73:975-980 (1999). "Separation of alcohol-water mixture by pervaporation through a novel natural polymer blend membrane-chitosan/silk fibroin blend membrane—chitosan / silk fibroin blend membrane.".

(56) References Cited

OTHER PUBLICATIONS

Chen et al., Proteins: Structure, Function, and Bioinformatics, 68:223-231 (2007). "Conformation transition kinetics of *Bombyx mori* silk protein.".
Database WPI Week 198205, Derwent Publications Ltd., London, GB AN 1982-09092E & JP 56 166235 A Dec. 21, 1981. Abstract.
Demura et al., Biosensors, 4:361-372 (1989). "Immobilization of biocatalysts with *Bombyx mori* silk fibroin by several kinds of physical treatment and its application to glucose sensors.".
Demura et al., J Membrane Science, 59:32-52 (1991). "Porous membrane of *Bombyx mori* silk fibroin: structure characterization, physical properties and application to glucose oxidase immobilzation.".
Derwent Record, Abstract of JP 08295697 A2 "Production of aqueous solution of silk fibroin at high concentration." Nov. 12, 1996.
Doshi et al. J Electrostatics, 35:151-160 (1995). "Electrospinning process and applications of electrospun fibers.".
Freddi et al., J Appl Polymer Sci, 56:1537-1545 (1995). "Silk fibroin/cellulose blend films: preparation, structure, and physical properties.".
Hijirida et al., Biophysical Journal, 71:3442-3447 (1996). "13C NMR of *Nephila clavipes* major ampullate silk gland.".
Hinman et al., Tibtech, 18:374-379 (2000). "Synthetic spider silk: a modular fiber.".
Huang et al., J Biomater Sci Polymer Edn, 12(9):979-993 (2001). "Engineered collagen-PEO nanofibers and fabrics.".
Huang et al., Macromolecules, 33:2989-2997 (2000). "Generation of synthetic elastin-mimetic small diameter fibers and fiber networks.".
Jin et al., Biomacromolecules, 3:1233-1239 (2002). "Electrospinning *Bombyx mori* silk with poly(ethylene oxide).".

Kweon et al., J Appl Polymer Sci, 80:1848-1853 (2001). "Preparation of semi-interpenetrating polymer networks composed of silk fibroin and poly(ethylene glycol) macromer.".
Lazaris, Science, 295:472-476 (2002). "Spider silk fibers spun from soluble recombinant silk produced in mammalian cells.".
Liang et al., J Appl Polymer Sci, 45:1937-1943 (1992). "Improvements of the physical properties of fibroin membranes with sodium alginate.".
MeGeed et al., Pharmaceutical Research, 19(7):954-959 (2002). "Controlled release of plasmid DNA from a genetically engineered silk-elastinlike hydrogel.".
Petrini et al., Journal of Materials Science: Materials in Medicine, 12:849-853 (2001). "Silk fibroin-polyurethane scaffolds for tissue engineering.".
Reneker et al., Nanotechnology, 7:216-223 (1996). "Nanometre diameter fibres of polymer, produced by electrospinning.".
Sawyer et al., JAMA, 191(9):740-742 (1965). "Dextran therapy in thrombophlebitis." Abstract.
U.S. Appl. No. 60/906,509, filed Mar. 13, 2007 by Omenetto et al.
U.S. Appl. No. 61/224,618, filed Jul. 10, 2009 by Numata et al.
Wang et al., Langmuir, 21:11335-11341 (2005). "Biomaterial coatings by stepwise deposition of silk fibroin.".
Yamada et al., Thin Solid Films, 440:208-216 (2003). "AFM observation of silk fibroin on mica substrates: morphologies reflecting the secondary structure.".
Zhou et al., Chem Commun, 2518-2519 (2001). "Preparation of a novel core-shell nanostructured gold colloid-silk fibroin bioconjugate by the protein in situ redox technique at room temperature.".

\* cited by examiner

ELECTROSPUN SILK MATERIAL SYSTEMS FOR WOUND HEALING

CROSS REFERENCE TO RELATED APPLICATIONS

This application is a 35 U.S.C. §371 National Phase Entry Application of International Application No. PCT/US2010/041953 filed Jul. 14, 2010, which designates the U.S., and which claims benefit under 35 U.S.C. §119(e) of U.S. Provisional Application No. 61/225,335 filed Jul. 14, 2009, the content of which is incorporated herein by reference in its entirety.

GOVERNMENT SUPPORT

This invention was made with funding under grant No. P41 EB002520, awarded by the National Institutes of Health (Tissue Engineering Resource Center). The U.S. government has certain rights in the invention.

FIELD OF THE INVENTION

The present invention relates to the processes for preparing silk/polyethylene oxide blended materials, and the resulting materials thereof, which are suitable for biomedical applications such as wound healing.

BACKGROUND OF THE INVENTION

Wound healing, or wound repair, is the body's natural process of regenerating dermal and epidermal tissue. The processes of wound healing are complex and fragile. Among these, the treatment of full-thickness burns continues to be one of the most challenging tasks in medicine. Patients sustaining full thickness injuries over a large percentage body surface area (BSA) often incur complications from eschars, which may lead to systemic bacterial infection, hypovolemia, hypothermia, hypoperfusion, and hemoglobinuria due to rhabdomyolysis and hemolysis. Currently, full thickness burn wounds are generally healed with minimal cicatrization by autologous skin grafting. Autologous skin grafting has limitations, however: Patients incurring full thickness burn wounds over 20% BSA are limited to either temporary stretched meshed allografts from cadavers or artificial dermal regeneration templates such as porcine xenografts and collagen coated semi-permeable synthetic membranes. Along with being immunologically incompatible with the patient, these substitutes induce healing with an acute distribution of wide irregular collagen bands resulting in an uneven grid-like surface and excessive hyperplastic, hypertrophic scarring.

Various synthetic and natural polymers may be used to develop wound dressing materials, for example, hydrolytically unstable synthetic aliphatic polyesters such as poly(g-lycolic acid) (PGA), poly(L-lactic acid) (PLA) or natural-origin polymer such as chitosan. These polymers may suffer from side reactions or reduced performance, however, when subjected to the specific wound environment. For example, the acidity of the hydrolyzed bi-products of PGA or PLA polymers may inhibit full-thickness wound healing cascades; when immersed in an acidic wound environment, chitosan becomes soluble due to amine group protonation which can result in premature loss of mechanical integrity.

Hence, there is a need for new types of biomaterials that not only have improved biodegradability, biocompatibility and possess the wound healing properties of natural skin, but also have improved physical and mechanical properties, and satisfactory flexibility suitable for an effective wound dressing.

SUMMARY OF THE INVENTION

The present invention provides a process for production of silk blend mats. The process comprises the steps of blending a polyethylene oxide (PEO) with an aqueous silk fibroin solution; electrospinning the blended solution, thereby forming a silk protein/PEO blended mat; and constraint-drying the electrospun silk mat. A crystallization dish technique may be employed in the constraint-drying step. The process may further comprise the step of treating the electrospun silk mat in alcohol and/or water solution prior to or after the drying step. The alcohol may be methanol, ethanol, isopropyl alcohol (2-propanol) or n-butanol. The process may further comprise the step of extracting the PEO from the silk mat. PEO may be extracted from the silk mat by leaching in water. Additionally, the process may further comprise the step of embedding at least one active agent in the silk mat, such as a therapeutic agent or a biological material.

The present invention also provides for a silk material prepared by the process comprising the steps of blending a polyethylene oxide (PEO) with an aqueous silk fibroin solution; electrospinning the blended solution, thereby forming a silk protein/PEO blended mat; and constraint-drying the electrospun silk mat.

Some embodiments of the invention relate to a silk material embedding or encapsulating at least one active agent for dressing a wound to promote wound healing prepared by the process comprising the steps of blending a polyethylene oxide (PEO) with an aqueous silk fibroin solution comprising at least one active agent; electrospinning the blended solution, thereby forming a silk protein/PEO blended mat encapsulating the active agent(s); and constraint-drying the electrospun silk mat. Alternatively, the active agent(s) may be added to the silk fibroin after blending with PEO or added to the electrospun silk material, for example, the electrospun silk/PEO mats may be coated with the active agent(s).

The present invention also relates to an electrospun silk mat comprising at least a silk fibroin protein, where the content of the silk fibroin protein in the silk mat ranges from about 50 wt % to about 90 wt %, and the silk mat has a thickness of about 20 to 80 microns.

The present invention also relates to an electrospun silk mat comprising a silk fibroin protein and a polyethylene oxide (PEO). The electrospun silk mat has a silk fibroin protein/PEO blend ratio from 2:1 to 4:1, or silk percentage is about 75% w/w to 90% (w/w); and the silk mat has a thickness of about 20 to 80 about microns.

In one embodiment, the electrospun silk mat is as thin as about 20 to 30 microns.

In one embodiment, the electrospun silk mat has interconnected pores with the pore throat size surface area averaging from about 0.1 to about 1 micron.

The electrospun silk mats prepared by the processes of the invention exhibit good structural, morphological, biofunctional and biocompatible properties suitable for biomedical application, particularly wound dressing. For example, the resulting silk mats of the invention degrade more than about 86% weight in less than 14 days; the equilibrium water content of the silk mats of the invention is more than about 82%; the oxygen transmission rate of the silk mats is more than about 15460 $cm^3/m^2/day$; and water vapor transmission rate of the silk mats is more than about 1934 $g/m^2/day$.

Some embodiments of the invention also relates to a method of promoting wound healing comprising contacting the wound with at least one constraint-dried electrospun silk mat comprising a silk fibroin protein, and optionally, at least one active agent. The electronspun silk mat has a silk fibroin content ranging from about 50 wt % to about 90 wt %; and the silk mat has a thickness of about 20 to about 80 microns.

Some embodiments of the invention also relates to a method of promoting wound healing comprising contacting the wound with at least one constraint-dried electrospun silk mat comprising a silk fibroin protein, PEO, and optionally, at least one active agent. The electronspun silk mat has a silk fibroin/PEO blend ratio from about 2:1 to about 4:1 (or the silk fibroin percentage in the electrospun silk mat is about 75% w/w to 90% w/w, or the PEO percentage in the electrospun silk mat is about 10% w/w to about 25% w/w); and the silk mat has a thickness of about 20 to about 80 microns.

BRIEF DESCRIPTION OF THE DRAWINGS

FIG. 7A depicts broad views of all three mats at 1.5× magnification. Contour lines in the images of 3:1 and 2:1 mats reflect directional fiber elongation and alignment. FIG. 7B shows close up views of all three silk mats at 1.5× magnification. Arrows in the images of 3:1 and 2:1 highlight fiber aggregation and alignment. FIG. 7C depicts the 12× magnification of 3:1 and 2:1 silk mats. Circles in the 3:1 image expose evidence of phase dispersion between aligned fibers. Arrows emphasize the detailed contour of taut elongated fibers in the 2:1 image. FIG. 7D shows that the circled region in the 50× image of the 2:1 silk mat reveals melded fibers. FIG. 7E depicts the 2.5× magnification of cross-sectional images for all three silk models. Images reflect the inverse relationship between fiber density and silk concentration.

FIG. 12A illustrates the linear fit analysis performed on the average biodegradation material loss across all material groups (SD±%, n=3). FIGS. 12B presents the scatter plot representation of logarithmic transformation of percent mass loss over all samples of each silk material group. Transformation indicates a degradation transition point just prior to the day three time point for all silk material systems. FIG. 12C illustrates the biodegradation rate analysis for each silk group for all time points, from day 0 to day 3 and from day 3 to day 14 time points. Data indicates two distinct degradation trends. Up to day 3, all the silk groups have accelerated enzymatic degradation rates between −10 and −12 (units=mass loss over time). After day 3, the enzymatic degradation slopes significantly declined to −3 to −5 for all silk materials.

FIGS. 14A and 14B show the S87-S76 mats viewed at 1.5× magnification. Images disclose progressive fiber elongation, aggregation and alignment. FIG. 14C are 12× magnification images exposing phase dispersion between aligned S82 fibers and well-defined elongated S76 fibers. FIG. 14D depicts the 50× magnification image showing the melded intertwined S76 fiber structure. FIG. 14E shows the cross-sectional view of S87-S76 mats at 2.5× magnification. Images reflect the inverse relationship between fiber density and silk concentration.

FIG. 16A illustrates the averaged percent linear fit representation of S87-S57 biodegraded material groups over each time point (SD±%, n=3). FIG. 16B presents the logarithmic transformation of all biodegraded samples over all time points. Transformation indicates a degradation transition point just prior to the day three time point for all S87-S75 material systems. FIG. 16C illustrates the biodegradation rate analysis for each silk group over all time points, from the start to day 3, and from day 3 to day 14. The data indicate two distinct degradation trends. Up to day 3, all silk groups had accelerated enzymatic degradation rates between −10 and −12 (units=mass loss over time). After day 3, the enzymatic degradation rates significantly declined between −3 and −5 for all silk materials.

DETAILED DESCRIPTION OF THE INVENTION

Figure 1A:
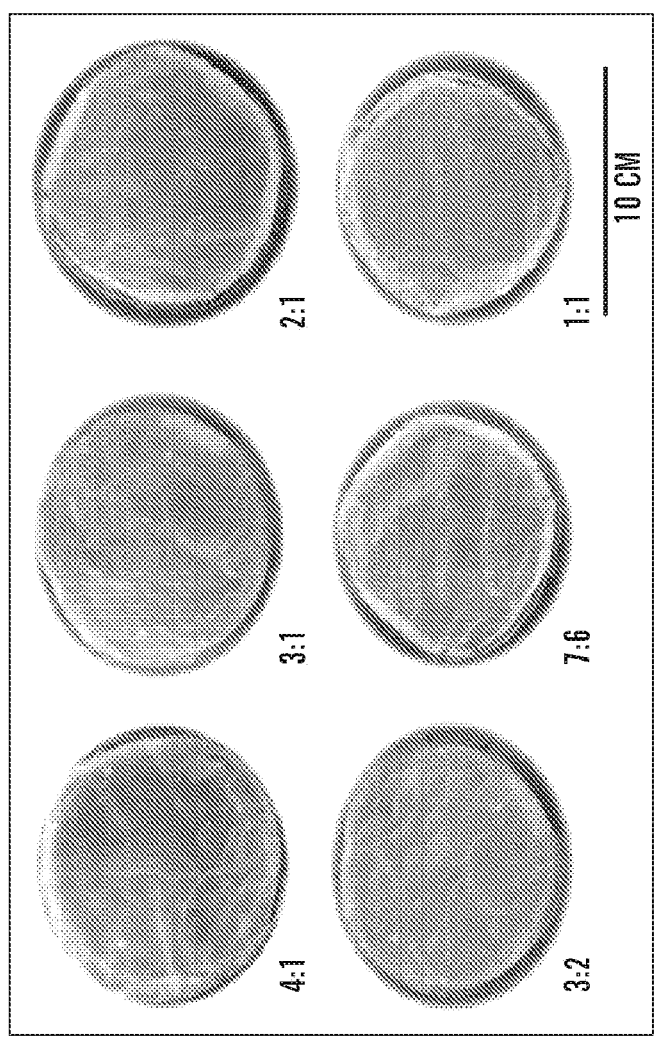
FIG. 1A shows six electrospun silk mats with silk/PEO ratios of 4:1, 3:1, 2:1, 3:2, 7:6, and 1:1, corresponding to 86.5%, 82.8%, 76%, 70.6%, 65.1% and 61.5% w/w silk fibroin protein percentage for each material group, respectively. The 10 cm diameter silk mats were treated with methanol and immersed in water.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention relates to the processes of preparing silk/polyethylene oxide blended materials, and the resulting materials thereof, which are suitable for biomedical applications such as wound healing. In particular, the electrospun silk fibroin/PEO mats with a silk fibroin/PEO blend ratio of 2:1 to 4:1 and dried via controlled evaporation and a constraint-drying technique, demonstrated suitable physical and bio-functional properties, such as fiber structure, topography, porosity, absorption, water vapor transmission rates, oxygen permeation, and biodegradability, relevant to biomaterial systems with utility for wound dressings The treatment of full-thickness burn wounds continues to be one of the most challenging tasks in medicine. Every year in the U.S., three thousand deaths occur and over one million patients are treated for burn wounds sustained from thermal, radiation, chemical and electrical sources which range from first degree epidermal injury to third degree full thickness dermal wound. Beers et al., MERCK MANUAL DIAGNOSIS & THER. (Merck & Co., Inc., Boston, Mass., 2006). Patients sustaining full thickness injuries over a large percentage of BSA often incur complications from eschars, including systemic bacterial infection, hypovolemia, hypothermia, hypoperfusion, and hemoglobinuria due to rhabdomyolysis and hemolysis. Ratner et al., BIOMATS. SCI. INTRO. MATS. MED. (Acad. Press, NY, 2004); Beers et al., 2006; Malafaya et al., 59 Adv. Drug Deliv. Rev. 207-33 (2007). Without immediate treatment, full-thickness burn wounds can trigger hypovolemic shock, immuno-suppression, and bacterial sepsis leading to systemic inflammatory response syndrome (SIRS), organ failure, and death.

Currently, full thickness burn wounds are typically healed with minimal cicatrization by autologous skin grafting. Skin is a durable biomaterial composite with excellent flex strength which offers a physical barrier to deleterious bacteria and provides an important blood-surface interface promoting balanced static blood flow and thrombotic wound healing cascades. The excellent adsorption, gas and water vapor transmissibility properties of skin allow for the drainage of proteinaceous exudates while inhibiting edema and dehydration thus promoting thermoregulation, cellular infiltration and soft tissue regeneration. Kim et al., 341 Int. J. Pharm. 35-43 (2007); Lee et al., 11 J. Mater. Sci.-Mater. Med. 817-23 (2000). The immediate application of a permanent split-thickness autologous skin graft will initiate neovascularization after 72 hours and often results in complete dermal reconstruction without complications of joint contractures, ischemia, scarring or systemic toxicity. Ratner et al., 2004; Beers et al., 2006.

There are limitations to autologous skin grafting, however. Patients incurring full thickness burn wounds over 20% BSA are typically treated with either temporary stretched meshed allografts from cadavers, or artificial dermal regeneration templates such as porcine xenografts and collagen coated semi-permeable synthetic membranes. Along with being immunologically incompatible with the patient, these substitutes often induce healing with an acute distribution of wide irregular collagen bands resulting in an uneven grid-like surface and excessive hyperplastic, hypertrophic scarring. Queen et al., 8 Biomats. 367-71 (1987); Ratner et al., 2004; Beers et al., 2006. Therefore, it is necessary to develop an effective wound dressing which not only possesses the wound healing properties of natural skin but is also fully biodegradable.

Various synthetic and natural polymers which have good biodegradability, biocompatibility and mechanical properties may be used to develop wound dressing materials. Hydrolytically unstable synthetic aliphatic polyesters such as poly(glycolic acid) (PGA), poly(L-lactic acid) (PLA), and poly(lactic-co-glycolic acid) (PLGA) are employed in many medical applications including surgical implants, bone cements, resorbable sutures, and microsphere controlled release systems. Quynh et al., 43 Eur. Polym. J. 1779-85 (2007); Wu & Wu 91 Polym. Degrad. Stab. 2198-204 (2006). Although porous electrospun PLA and PGA fibers are currently being explored as wound dressing materials, the acidity of the hydrolyzed bi-products of these polymers may inhibit full-thickness wound healing cascades. Quynh et al., 2007; Wu & Wu, 2006. The natural-origin polymer chitosan, a disaccharide constructed of glucosamine and N-acetylglucosamine and similar to heparin, has been found to accelerate wound healing by promoting thrombotic cascades and stimulating polymorphonuclear (PMN) and mononuclear cellular migration to the wound site. Kim et al., 341 Int. J. Pharm. 35-43 (2007); Malafaya et al., 2007. When immersed in an acidic wound environment, however, chitosan becomes soluble due to amine group protonation which can result in premature loss of mechanical integrity. Hence the co-polymerization of other synthetic polymers to form films, gels or sponges with the flexibility is necessary for a full thickness wound dressing. Kim et al., 2007; Malafaya et al., 2007.

The present invention provides for a natural fibroin silk which has distinct biological properties across a wide range of material morphologies including films, fibers, gels, and porous sponges. Vepari & Kaplan 32 Prog. Polym. Sci. 991-1007 (2007). Produced by silkworms and spiders, silk fibroin is a protein based biopolymer primarily composed of glycine and alanine. Vepari & Kaplan, 2007; Zhou et al. 12 Nucleic Acids Res. 2413-19 (2000); Tanaka et al., 29 Insect Biochem. Mol. Biol. 269-76 (1999). Structurally, silk fibroin biopolymer contains a repetitive sequence of amino acids that form a heavy chain that crystallizes, and a less crystalline light chain. The interaction of amphiphilic regions of the fibroin yields a significant content of crystalline β-sheets (approximately 55%), along with other secondary structures to generate the mechanical and bio-functional attributes of this unique biopolymer. Vepari & Kaplan, 2007; Wang et al., 39 Macromol. 1102-07 (2006); Wang et al., 37 Macromol. 6856-64 (2004); Jin et al., 15 Adv. Funct. Mater. 1241-47 (2005); Hu et al., 39 Macromol. 6161-70 (2006). The tightly packed crystalline β-sheets exclude water, while the less crystalline domains in the assembled protein remain organized via hydrogen bonding and can respond to changes in water content. Wong et al., 82 Appl. Phys. A-Mater. 293-303 (2006). Extensive cell and tissue studies have been conducted with silk protein biomaterials, including bone, cartilage, ligament and blood vessel engineering, among others, demonstrating the biocompatible and effective tissue regenerative features of this protein system. Vepari & Kaplan 2007. With regard to wound dressings, silk films have been shown to heal full thickness skin wounds in rats faster and with lower inflammatory response than traditional porcine-based wound dressings. Sugihara et al., 225 Exp. Biol. Med. 58-64 (2000).

An embodiment of the present invention provides for silk matrices with potential utility for wound dressings prepared utilizing a blend of silk fibroin/polyethylene oxide (PEO) two-fluid electrospinning techniques. Wang et al., 39 Macromol. 1102-07 (2006). Electrospinning is a simple, versatile, and useful technique for fabricating nanofibrous membranes from a rich variety of functional materials. Doshi & Reneker 35 J. Electro. 151-60 (1995); Reneker & Chun 7 Nanotech. 216-23 (1996); Fridrikh et al., 90 Phys. Rev. Let. 144502-06 (2003). Although a significant number of natural and synthetic materials have been electrospun to form wound dressings, challenges remain in terms of biocompatibility, mechanical properties, and overall functional performance. In the present invention, continuously spinning silk fibroin to a targeted platform produced large confluent silk mats, constructed of layered fiber sheets, with a thickness relative to the silk/PEO ratio concentration and volume of spinning dope used. The silk mats were immersed in methanol, triggering the physical crosslinking associated with β-sheet crystallization, inducing the formation of water stabilized materials. Exploiting the unique fiber porosity and surface roughness of variant silk/PEO blends (Jin et al., 3 Biomacromol. 1233-39 (2002); Wang et al., 37 Macromol. 6856-64 (2004)), silk material systems with different silk/PEO blended ratios were prepared and evaluated for physical and bio-functional properties in the context of wound healing needs.

The present invention thus provides for processes for production of silk blend mats. The process comprises the steps of blending a polyethylene oxide (PEO) with an aqueous silk fibroin solution; electrospinning the blended solution, thereby forming a silk protein/PEO blended mat; and constraint-drying the electrospun silk mat. A crystallization dish or polystyrene container with the desired mouth size may be employed in the constraint-drying step.

Electrospinning can be performed by any means known in the art (see, for example, U.S. Pat. No. 6,110,590). For example, a steel capillary tube with a 1.0 to 2.0 mm internal diameter tip is mounted on an adjustable, electrically insulated stand. The capillary tube is generally maintained at a high electric potential and mounted in the parallel plate geometry. The capillary tube may be connected to a syringe filled with silk/biocompatible polymer solution. A constant volume flow rate is usually maintained using a syringe pump, set to keep the solution at the tip of the tube without dripping. As displayed in Table 1, the electric potential (10-12 kV), solution flow rate (0.014-0.032 mL/min), and the working distance between the capillary tip and the collection screen (20-22.5 cm) are adjusted so that a stable jet is obtained. Dry or wet fibers are collected by varying the distance between the capillary tip and the collection screen.

TABLE 1

Eectrospinning parameters for each silk/PEO blend.

| 8% Silk/PEO (w/w) | Viscosity (mPa·s) | Potential-Ground Working Distance (cm) | Injection Rate (mL/min) |
|---|---|---|---|
| 4:1 (5% PEO) | ≈128 | 22 ± .5 | .032 ± .002 |
| 3:1 (5% PEO) | ≈152 | 22 ± .5 | .030 ± .002 |
| 2:1 (5% PEO) | ≈240 | 22 ± .5 | .028 ± .002 |
| 3:2 (6% PEO) | ≈424 | 20.5 ± .5 | .024 ± .002 |

TABLE 1-continued

Eectrospinning parameters for each silk/PEO blend.

| 8% Silk/PEO (w/w) | Viscosity (mPa · s) | Potential-Ground Working Distance (cm) | Injection Rate (mL/min) |
|---|---|---|---|
| 7:6 (6% PEO) | ≈768 | 20.5 ± .5 | .018 ± .002 |
| 1:1 (6% PEO) | ≈1120 | 20.5 ± .5 | .014 ± .002 |

Viscosities for the 8% wt silk, 5% PEO, and 6% PEO solutions were ≈24, ≈4464, and ≈7520 centipoise (mPa · s) respectively. Three batch solutions of 4.5 mL, 8 mL, and 10.4 mL for each blend were made up to create 10, 13, and 16.5 cm diameter silk mats respectively.

A collection plate or a collection screen suitable for collecting silk fibers can be a wire mesh or a polymeric mesh. Alternatively, the collection screen is an aluminum foil (10-16.5 cm diameter). The aluminum foil can be coated with Teflon fluid to make peeling off the silk fibers easier. One skilled in the art will be able to readily select other means of collecting the fiber solution as it travels through the electric field. As is described in more detail below, the electric potential difference between the capillary tip and the aluminum foil counter electrode may be gradually increased to about 10-12 kV, however, one skilled in the art should be able to adjust the electric potential to achieve suitable jet stream.

The electrospun mat is then constraint-dried. The process of the invention may further comprise the step of treating the electrospun silk mats in alcohol/water solution before or after the drying steps to induce the beta-sheet formation and crystallization. The alcohol may be methanol, ethanol, isopropyl alcohol (2-propanol) or n-butanol. Furthermore, the PEO may be extracted from the silk mat. Extraction of PEO from silk mat may be performed by leaching the electrospun silk blend mats in water (e.g., $dH_2O$) for a period of time, such as over 1 to 3 days.

As used herein, the term "fibroin" includes silkworm fibroin and insect or spider silk protein. Lucas et al., 13 Adv. Protein Chem. 107-242 (1958). For example, fibroin is obtained from a solution containing a dissolved silkworm silk or spider silk. The silkworm silk protein is obtained, for example, from *Bombyx mori*, and the spider silk is obtained from *Nephil clavipes*. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that may be used.

An aqueous silk fibroin solution may be prepared from silkworm cocoons using techniques known in the art. Suitable processes for preparing silk fibroin solution are disclosed, for example, in U.S. patent application Ser. No. 11/247,358; WO/2005/012606; and WO/2008/127401. In one embodiment, *B. mori* cocoons are boiled for about 30 minutes in an aqueous solution. The aqueous solution may be 0.02 M sodium carbonate. The cocoons are rinsed with water to extract the sericin proteins and the extracted silk is dissolved in an aqueous salt solution. Salts useful for this purpose include, but not limited to, lithium bromide, lithium thiocyanate, calcium nitrate or other chemicals capable of solubilizing silk. For example, the extracted silk maybe dissolved in about 9-12 M LiBr solution at 60° C. for 4 hours, yielding a 20% (w/v) solution. The salt is consequently removed using dialysis. The solution maybe centrifuged to remove small amounts of silk aggregates that may form during the process, usually from environment contaminants that are present on the cocoons. The final concentration of silk fibroin aqueous solution may be approximately 8% (w/v). To obtain a silk fibroin solution with a higher concentration, the silk fibroin solution with a lower concentration may be dialyzed against a hygroscopic polymer, for example, PEG, a polyethylene oxide, amylose or sericin. For example, an 8% silk fibroin solution may be dialyzed against 10% (w/v) PEG (10,000 g/mol) solution. The dialysis is for a time period sufficient to result in a final concentration of aqueous silk solution between 10-30%. In most cases dialysis for 2-12 hours is sufficient.

The silk fibroin solution can be combined with one or more biocompatible polymers such as polyethylene oxide, polyethylene glycol, collagen, fibronectin, keratin, polyaspartic acid, polylysin, alginate, chitosan, chitin, hyaluronic acid, and the like; or one or more active agents, such as cells, enzymes, proteins, nucleic acids, antibodies and the like, as described herein. See, e.g., WO 2004/062697 and WO 2005/012606. Silk fibroin can also be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; U.S. Applications Ser. No. 61/227,254; Ser. No. 61/224,618; Ser. No. 12/192,588.

A broad range of silk fibroin and PEO concentrations, in the aqueous solution, are suitable for preparing the blended solutions for electrospinning the silk materials. For example, the concentration of silk fibroin in the solution may be less than about 30 wt % before the blending; and the concentration of PEO in the solution may range from about 1% to about 15 wt % before the blending, depending on the solubility and viscosity of PEO solution. For example, an aqueous solution having a concentration about 5 wt %-15 wt % silk fibroin and an PEO solution having a concentration about 3 wt %-10 wt % PEO may be used for blending. In one embodiment, 8 wt % silk fibroin solution and 5 wt % PEO solution is used for blending. In another embodiment, 8 wt % silk fibroin solution and 6 wt % PEO solution is used for blending. Both the initial concentrations of silk fibroin solution and PEO solution and the initial blending ratio between silk fibroin protein and PEO may depend on the viscoelastic and surface tension properties desired to generate stable fluid jets during electrospinning. Jin et al., 3 Biomacromol.s 1233-39 (2002). The initial concentrations of silk fibroin solution and PEO solution and the initial blending ratio between silk fibroin protein and PEO may also depend on the desired weight percentage of silk fibroin and/or PEO in the final silk blend mat.

In one embodiment, the silk biomaterials of the present invention may contain at least one therapeutic agent. To form these materials, the silk fibroin or silk fibroin/PEO solution is mixed with a therapeutic agent prior to forming the matrix, or is loaded into the material after it is formed. The variety of different therapeutic agents that can be used in conjunction with the biomaterials of the present invention is vast.

In general, therapeutic agents which may be administered via the pharmaceutical compositions of the invention include, without limitation: antiinfectives such as antibiotics and antiviral agents; chemotherapeutic agents (e.g., anticancer agents); anti-rejection agents; analgesics and analgesic combinations; anti-inflammatory agents; hormones such as steroids; cell attachment mediators, such as the peptide containing variations of the "RGD" integrin binding sequence known to affect cellular attachment, biologically active ligands, and substances that enhance or exclude particular varieties of cellular or tissue ingrowth such as bone morphogenic proteins (e.g., BMPs 1-7), bone morphogenic-like proteins (e.g., GFD-5, GFD-7, and GFD-8), epidermal growth factor (EGF), fibroblast growth factor (e.g., FGF 1-9), platelet derived growth factor (PDGF), insulin like growth factor (IGF-I and IGF-II), transforming growth factors (e.g., TGF-β I-III), TGF-, YIGSR peptides, glycosaminoglycans (GAGs), hyaluronic acid (HA), integrins, selectins and cadherins; vascular endothelial growth factor (VEGF); and other naturally derived or genetically engineered proteins, polysaccharides, glycoproteins, or lipoproteins. Growth factors are know in the art, see, e.g., Rosen & Thies, CELLULAR & MOL. BASIS BONE FORMATION & REPAIR (R.G. Landes Co., 2004).

The active agent can represent any material capable of being embedded in the silk materials. For example, the agent may be a therapeutic agent, or a biological material, such as cells (including stem cells), proteins, peptides, nucleic acids (e.g., DNA, RNA, siRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cell attachment mediators (such as RGD), cytokines, enzymes, small molecules, drugs, dyes, amino acids, vitamins, antioxidants, antibiotics or antimicrobial compounds, anti-inflammation agents, antifungals, viruses, antivirals, toxins, prodrugs, chemotherapeutic agents, or combinations thereof. See, e.g., PCT/US09/44117; U.S. Patent Application Ser. No. 61/224,618). The agent may also be a combination of any of the above-mentioned agents. Encapsulating either a therapeutic agent or biological material, or the combination of them, is desirous because the encapsulated product can be used for numerous biomedical purposes.

In some embodiments, the active agent may also be an organism such as a fungus, plant, animal, bacterium, or a virus (including bacteriophage). Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 2008/106485; PCT/US2009/059547; WO 2007/103442.

Exemplary antibodies that may be incorporated in silk fibroin include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents may also be antimicrobial peptides such as defensins, magainin and nisin; or lytic bacteriophage. The antibiotic agents can also be the combinations of any of the agents listed above. See also PCT/US2010/026190.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like. Interactions between components may also be used to functionalize silk fibroin through, for example, specific interaction between avidin and biotin. The active agents can also be the combinations of any of the enzymes listed above. See U.S. Patent Application Ser. No. 61/226,801.

When introducing therapeutic agents or biological material into the silk fibroin, other materials known in the art may also be added with the agent. For instance, it may be desirable to add materials to promote the growth of the agent (for biological materials), promote the functionality of the agent after it is released from the silk mats, or increase the agent's ability to survive or retain its efficacy during the period it is embedded in the silk. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-I), bone morphogenetic growth factors (BMPs), nerve growth factors, and related proteins may be used. Growth factors are known in the art, see, e.g., Rosen & Thies, CELLULAR & MOLECULAR BASIS BONE FORMATION & REPAIR (R.G. Landes Co., Austin, Tex., 1995). Additional options for delivery via the silk mats include DNA, siRNA, antisense, plasmids, liposomes and related systems for delivery of genetic materials; peptides and proteins to activate cellular signaling cascades; peptides and proteins to promote mineralization or related events from cells; adhesion peptides and proteins to improve silk mats-tissue interfaces; antimicrobial peptides; and proteins and related compounds.

Additional biocompatible material may also be blended into the silk fibroin mats, such as polyethylene glycol (see PCT/US09/64673), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, glycerol (see PCT/US2009/060135), and other biocompatible polymers, see WO 2004/0000915. Alternatively, the silk may be mixed with hydroxyapatite particles, see PCT/US08/82487. As noted herein, the silk fibroin may be of recombinant origin, which provides for further modification of the silk such as the inclusion of a fusion polypeptide comprising a fibrous protein domain and a mineralization domain, which are used to form an organic-inorganic composite. These organic-inorganic composites can be constructed from the nano- to the macro-scale depending on the size of the fibrous protein fusion domain used, see WO 2006/076711. See also U.S. patent application Ser. No. 12/192,588.

The silk-fibroin embedded active agents or biological materials may be suitable for long term storage and stabilization of the cells and/or active agents. Cells and/or active agents, when incorporated in the silk mats, can be stable (i.e., maintaining at least 50% of residual activity) for at least 30 days at room temperature (i.e., 22° C. to 25° C.) and body temperature (37° C.). Hence, temperature-sensitive active agents, such as some antibiotics, can be stored in silk mats without refrigeration. Importantly, temperature-sensitive bioactive agents can be delivered (e.g., through injection) into the body in silk mats and maintain activity for a longer period of time than previously imagined. See, e.g., PCT/US2010/026190.

The silk-fibroin embedded active agents (e.g., therapeutic agents) or biological materials are suitable for a biodelivery device. Techniques for using silk fibroin as a biodelivery device may be found, for example, in U.S. patent application Ser. No. 10/541,182; Ser. No. 11/628,930; Ser. No. 11/664,234; Ser. No. 11/407,373; PCT/US07/020,789; PCT/US08/55072; PCT/US09/44117. Some embodiments of the present invention relate to the utility of silk-fibroin embedded therapeutic agents or biological materials as drug delivery systems for potential utility in medical implants, tissue repairs and for medical device coatings.

The silk mats structure enables the biodelivery vehicle to have a controlled release. Controlled release permits dosages to be administered over time, with controlled release kinetics. In some instances, delivery of the therapeutic agent or biological material is continuous to the site where treatment is needed, for example, over several weeks. Controlled release over time, for example, over several days or weeks, or longer, permits continuous delivery of the therapeutic agent or biological material to obtain preferred treatments. The controlled delivery vehicle is advantageous because it protects the therapeutic agent or biological material from degradation in vivo in body fluids and tissue, for example, by proteases. See, e.g., PCT/US09/44117.

Controlled release of the bioactive agent from the silk mats may be designed to occur over time, for example, for greater than about 12 hours or 24 hours, inclusive; greater than 1 month or 2 months or 5 months, inclusive. The time of release may be selected, for example, to occur over a time period of about 12 hours to 24 hours, or about 12 hours to 1 week. In another embodiment, release may occur for example on the order of about 1 month to 2 months, inclusive. The controlled release time may be selected based on the condition treated.

For example, a particular release profile may be more effective where consistent release and high local dosage are desired.

Alternatively, a therapeutic agent could be coated on to the silk material with a pharmaceutically acceptable carrier. Any pharmaceutical carrier can be used that does not dissolve the matrix. The therapeutic agents may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. For example, the amount of drug may represent about 0.001% to about 70%, or about 0.001% to about 50%, or about 0.001% to about 20% by weight of the material. Upon contact with body fluids the drug will be released.

The silk material suitable for tissue engineering scaffolds can be further modified after fabrication. For example, the scaffolds can be coated with bioactive substances that function as receptors or chemoattractors for a desired population of cells. The coating can be applied through absorption or chemical bonding.

Some embodiments of the invention relate to a silk material embedding or encapsulating at least one active agent as a wound dressing to promote wound healing by blending a polyethylene oxide (PEO) with an aqueous silk fibroin solution comprising at least one active agent; electrospinning the blended solution, thereby forming a silk protein/PEO blended mat encapsulating the active agent(s); and constraint-drying the electrospun silk mat. Alternatively, the active agent(s) may be added to the silk fibroin after blending with PEO or added to the electrospun silk material, for example, the electrospun silk/PEO mats may be coated with the active agent(s).

The silk materials of the present invention are capable of topically delivering bioactive molecules and may represent a new generation of biomaterials. For example, electrospun silk mats which are made of nanoscale silk fibers, containing EGF, have been used for the promotion of wound healing processes. EGF incorporated into the silk mats could be slowly released in a time-dependent manner (e.g., 25% EGF release in 170 hours). The silk materials of the invention may be characterized in a 3-D wounded human skin-equivalents model, which displays the same structure as human skin and is able to heal using the same molecular and cellular mechanisms found in vivo. When the biofunctionalized silk mats are placed on the wounded human skin-equivalents model as a dressing, the silk mats aid the healing by decreasing the time of wound closure by the epidermal tongue by 90%. Schneider et al., Acta Biomater., (2009).

Some embodiments of the invention relate to an electrospun silk mat comprising a silk fibroin protein and PEO. In one embodiment, the electrospun silk mat has a silk fibroin protein/PEO blend ratio from about 2:1 to about 4:1. Based on silk/PEO weight ratios and the equation:

$$\text{Silk \%} = \frac{\text{Silk \%}}{\text{Silk \% + PEO \%}} \quad \text{(Equation 1)}$$

the w/w silk percentage of the silk mats may range from about 75% w/w to 90% w/w. The electrospun silk mat has a thickness in a range of about 20 microns to about 80 microns.

PEO concentration, or silk/PEO blend ratio, has a direct influence on the silk fiber surface area and the bulk morphology during the electrospinning process. Jin et al., 3 Biomacromol. 1233-39 (2002); Wang et al., 37 Macromol. 6856-64 (2004). As the PEO concentration increases, the size of the fibroin micelle and globule structures that form in the fiber decrease. Additionally, once encased in the whipping electrified fluid jet, these globule structures align and elongate up to 100,000 times. Wang et al., 2006; Kowalewski et al., 53 Bulletin Polish Acad. Sci., Tech. Sci. 385-94 (2005); Reneker & Yarin, 49 Polymer 2387-425 (2008). The present invention demonstrates that silk/PEO blend ratio plays a major role in properties of resulting silk mats including the fiber thickness, density, orientation, phase dispersion, porosity and mat thickness. Consequently, fibers formed with increased PEO concentration had a reduction in geometrical shape, surface area and bulk volume which correlates to the progressive visual and textural transformation observed from the 4:1 down to the 1:1 silk/PEO blended mats.

In one embodiment, six silk/PEO blended material systems prepared with the silk/PEO blend ratio of 4:1, 3:1, 2:1, 3:2, 7:6, and 1:1 were electrospun into confluent 16.5 cm and 10 cm diameter mats. The physical properties of each sample were evaluated in both water saturated and dry states. Immersed in water, the six matrices had a uniform conformation, displaying an opaquely translucent canescent appearance and were pliable with a silky texture, but with extended handling exhibited degenerating tensile strength respective of silk concentration, as shown FIG. 1A. The silky texture is referenced to describe the dynamic hygroscopic nature of fibroin where water molecules continuously plasticize throughout the amorphous polymer matrix. Either forming hydrogen bonds to amino, hydroxyl, or carboxyl acid end groups or free to disperse throughout the hydrophilic domain; this fluent environment is continuously transitioning due to kinetic energy minimization resulting in the soft silky texture of these saturated material systems. Hu et al., 39 Macromol. 6161-70 (2006); Agarwal et al., 63 J. Appl. Polym. Sci. 401-10 (1997); van der Heijden et al., 378 Thermochim. Acta 27-34 (2001); Wong et al., 2006. After a drying period of 24 hours at ambient temperature, the physical characteristics progressively changed over the six material systems. Relative to decreasing silk concentration, 86.5%, 82.8%, 76%, 70.6%, 65.1% and 61.5%, the mats changed from a snow-white pliable wafer texture with cohesive flex strength to a translucent-brown, ultra-thin, less-pliable, film-like material, as shown in FIGS. 2 and 3.

In the present invention, the drying method also influenced the physical and mechanical properties of the silk/PEO blended mats, such as the thickness of the electrospun silk/PEO blended mats. For example, an air-drying method employing polystyrene Petri dish may be used. Alternatively, a method of constraint-drying may be used. For example, a crystallization dish technique may be used for drying the electrospun silk mats.

The thickness of the electrospun silk mats of the present invention is from about 20 microns to about 80 microns. When a constraint-drying method is used, the thickness of the electrospun silk mats may average about 20 microns to 30 microns.

Figure 2A:
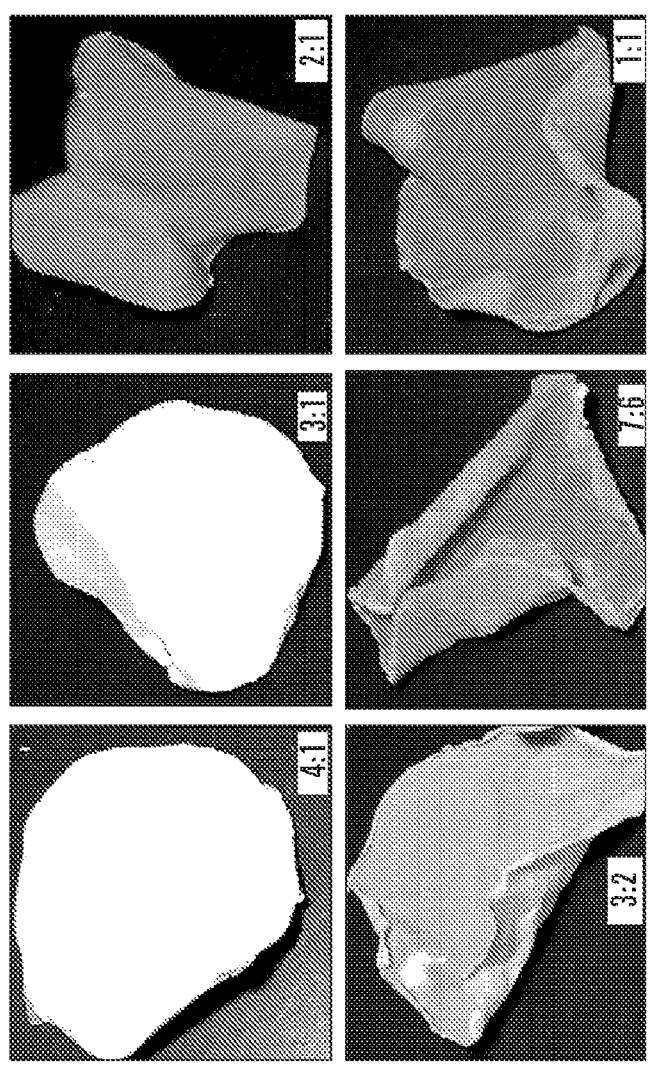
FIGS. 2A and 2B show 3.5 cm diameter air-dried (or unconstrained-dried) silk samples. The images reflect the progressive material deformation with respect to the decreasing silk concentration.
Figure 4:
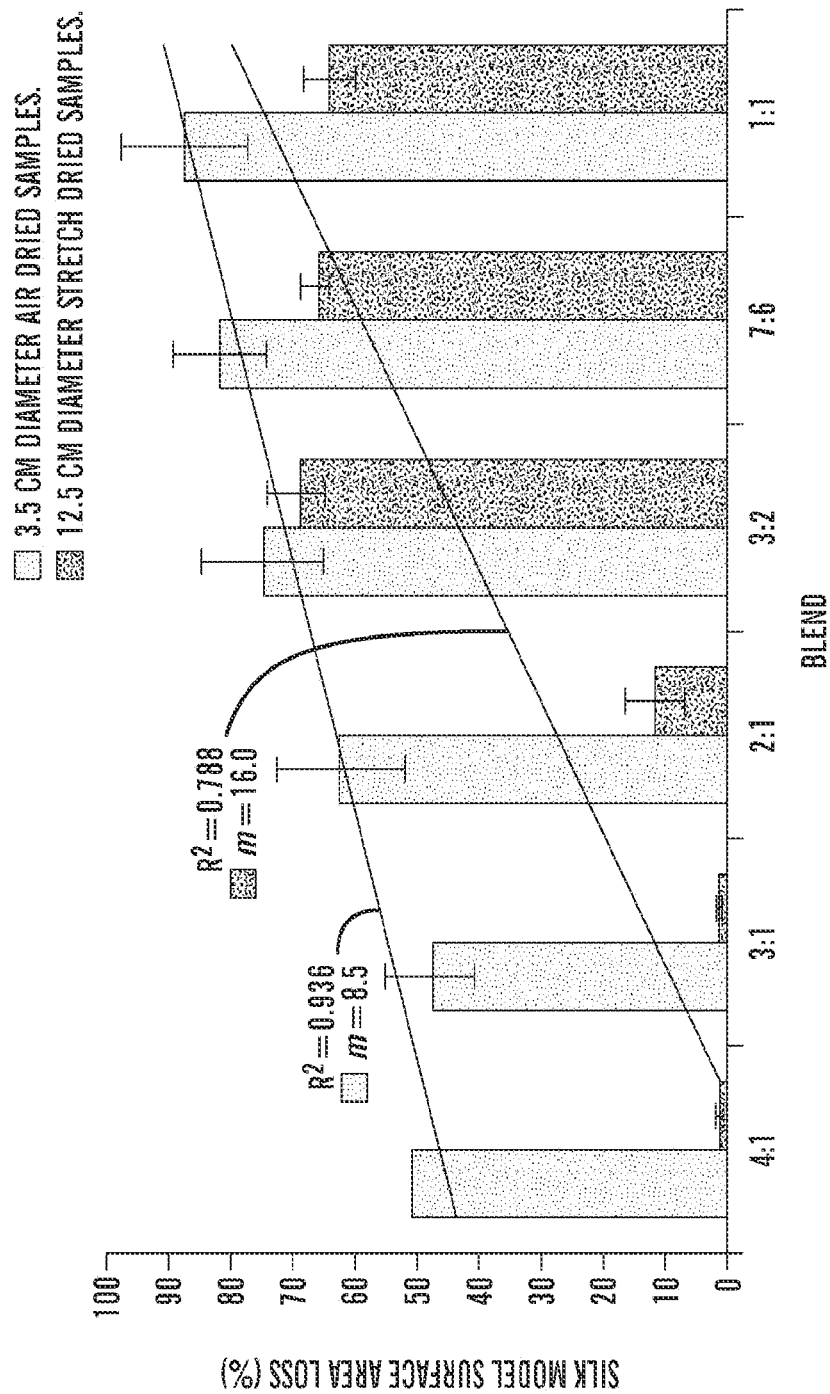
FIG. 4 is a graph depicting the percentage of the silk surface area transformation for small and large material group samples after air and constraint drying techniques. Surface area was determined via circular geometric assessment. Linear curve analysis was performed on the average percent surface area loss across all material groups (SD±%, n=3). Surface area loss between drying techniques was significantly different for the 4:1 and 3:1 material groups (P=0.001). Slope (m) and $R^2$ values indicate a linear progressive loss of surface area with decreasing silk concentration for air dried samples. In contrast, the surface area loss for the constraint-dried material groups escalated 30-fold from 2% for the 4:1 and 3:1 mats to over 60% for the 3:2, 7:6 and 1:1 material groups.
Figure 5:
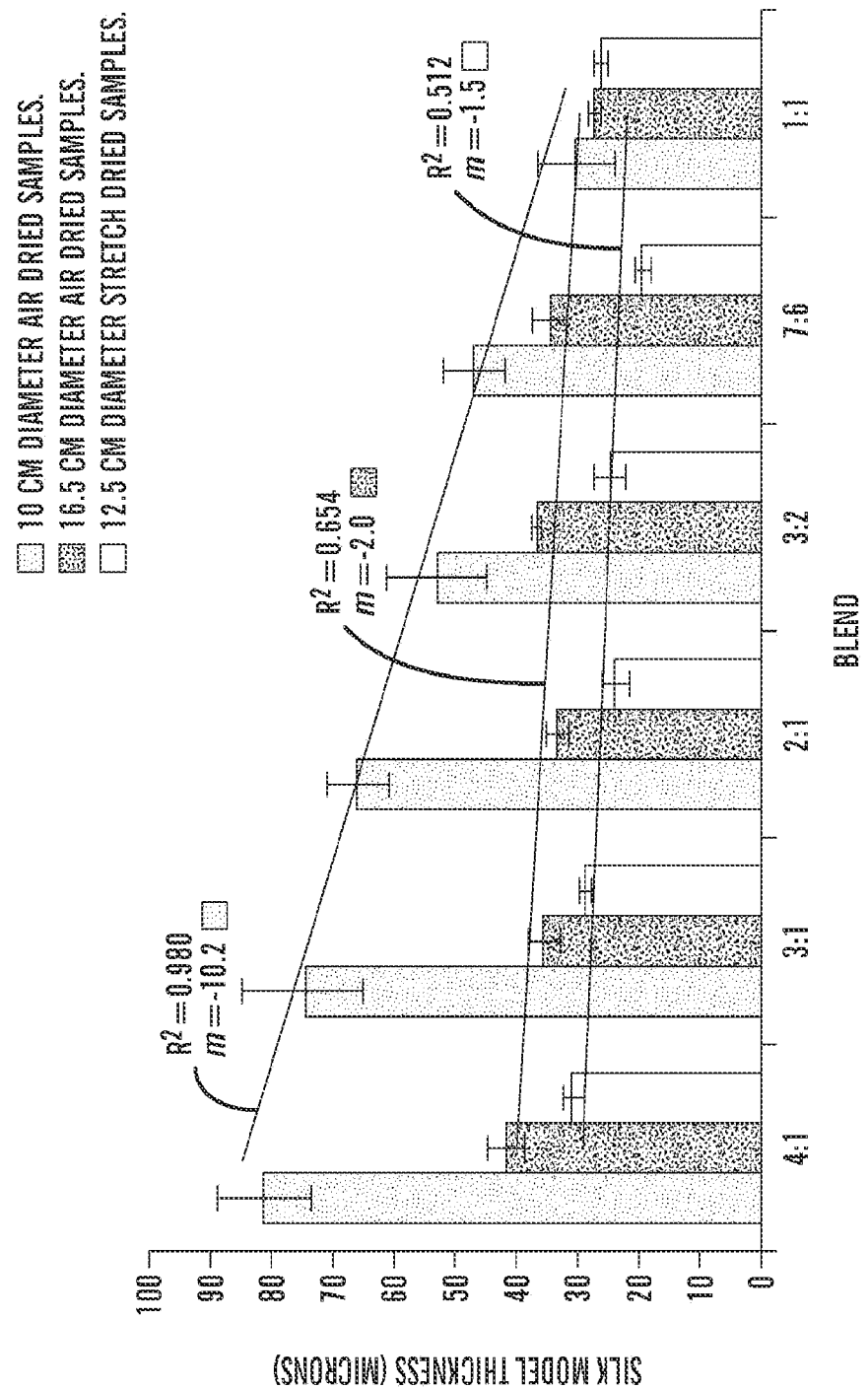
FIG. 5 is a graph depicting the relationship between silk material groups and thickness of the membranes based on (1) size of electrospun mat, and (2) after air and stretch drying techniques. Material thickness was determined utilizing the Ono Sokki EG-225F Digital Indicator. Linear curve analysis was performed on the average material thickness across all material groups (SD±%, n=6). All 10 cm air dried material groups were significantly thicker than the 16.5 air dried and 12.5 constraint-dried groups (P=0.001). Relative to silk concentration, slope (m) and $R^2$ values indicate a linear thickness reduction for the 10 cm air dried samples. Thickness slopes for the 16.5 cm air dried and 12.5 constraint-dried groups approached horizontal signatures with small degree of divergence over silk concentrations.

For example, the 3.5 cm diameter samples of the electrospun silk mats with the silk/PEO blend ratio of 4:1, 3:1, 2:1, 3:2, 7:6, and 1:1 were punched from 10 cm diameter mats and air dried using the polystyrene Petri dish method. The resulting silk mats are shown in FIG. 2A. Saturated, some 3.5 cm diameter samples were difficult to handle, often folding over in half in order to achieve a net force surface-surface hydrophobic equilibrium and displaying hydrophilic behavior with layered silk sheet separation and displacement. Throughout the water drying phase, as polar water molecules evaporated from the large surface area of this non-woven porous biomaterial, surface energy was minimized by the shifting of hydrophilic to hydrophobic domains at the interfaces. This dynamic surface structure reorganization manifests heavy chain realignment and β-sheet crystallization. Vepari & Kaplan, 2007; Jin et al., 200); Hu et al., 39 Macromol. 6161-70 (2006). Characteristic of twisted pleated β-sheet formation, none of the matrices dried in a completely flat orientation with only the 4:1 and 3:1 matrices maintaining the original circular shape. Additionally, there is a proline residue positioned at the terminus of the amorphous domains interlaced between the crystalline domains in the heavy chain of fibroin. Zhou et al., 2000. Proline has been shown to super-contract with dehydration, thus increasing the fiber's capacity to shrink. Liu et al., 9 Biomacromol. 116-21 (2008). With deceasing silk concentrations, these factors contribute in the dried samples losing between 51.0±0.0% and 87.5±9.9% of their surface area from the saturated to dry states (n=3), as shown in FIG. 4. The thickness measurements of each dried set of samples progressively declined from 81.7±7.5 to 77.5±10.5, to 66.7±5.1, to 53.3±8.1, to 46.7±5.1, and to 30.0±6.4 microns, respectively (n=6), as shown in FIG. 5.

Figure 3A:
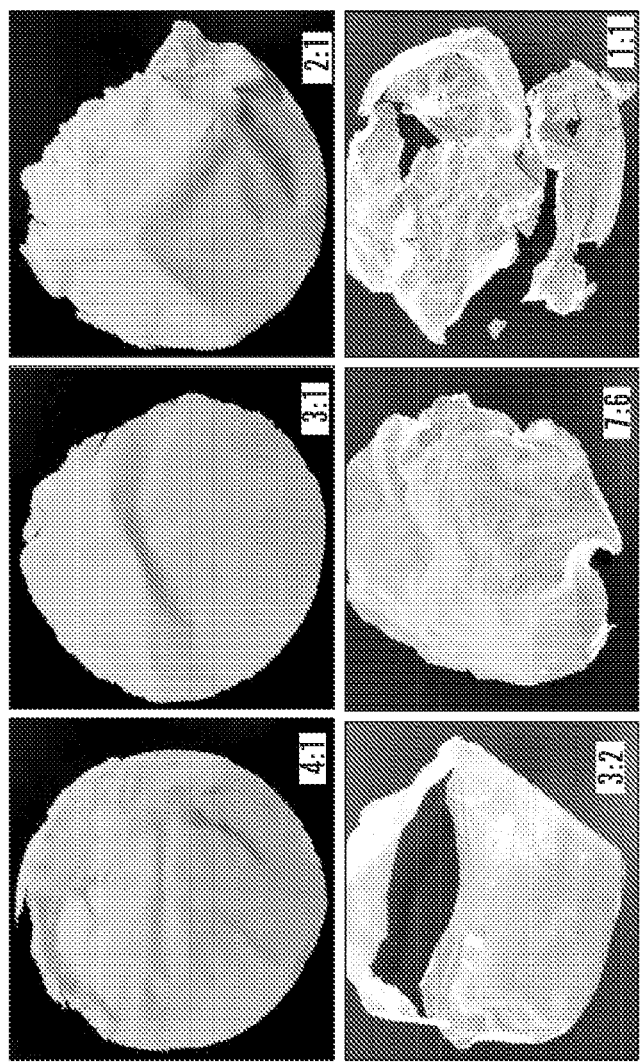
FIGS. 3A and 3B show 13 cm diameter constraint-dried silk mats (3A) and 12.5-cm diameter constrain-dried S87-S57 silk mats (3B). The images reveal the increased material shearing and deformation with respect to the decreasing silk concentration.
Figure 3B:
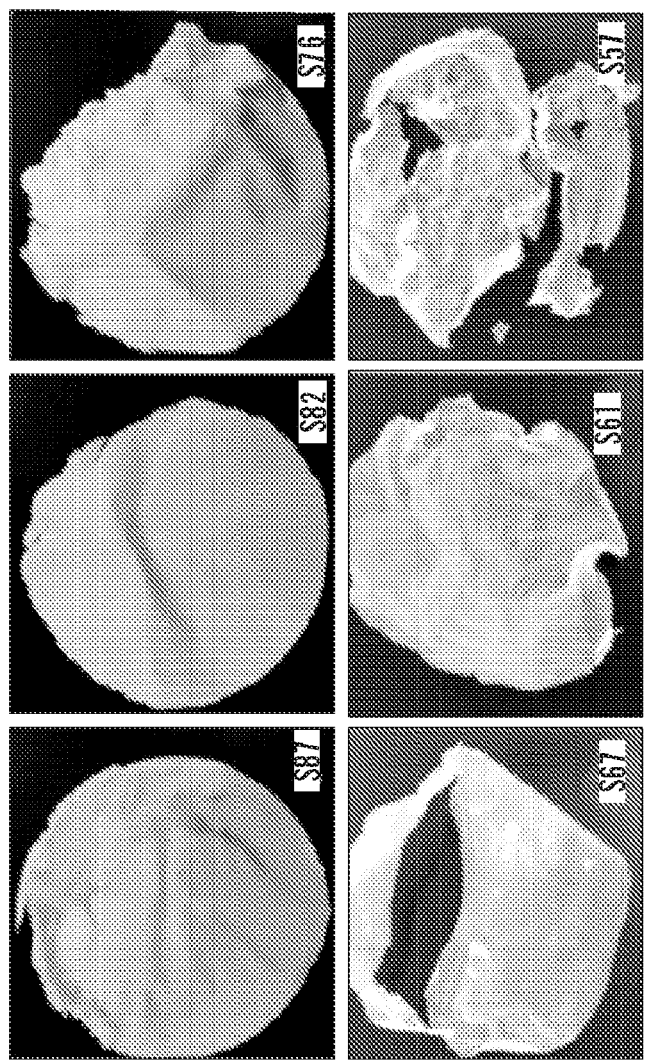

In another embodiment, the 12.5 cm diameter electrospun silk mats with the silk/PEO blend ratio of 4:1, 3:1, 2:1, 3:2, 7:6, and 1:1 were dried using the crystallization dish technique. The resulting silk mats are shown in FIG. 3A. Immersed in water, these larger samples were easier to unfold. With respect to hydrophilic forces, layered sheet separation was only observed in the interior region of each sample without sheet displacement. This may be because these samples were not punched from larger mats, thus retaining the crosslinked crystallized regions at the edge of the samples. During the drying phase, as the saturated samples uniformly dried from the rim towards the center of the sample, each set of mats progressively shrank across the mouth of the dish. The 4:1 and 3:1 samples completely dried attached to the rim of the crystallization dish resulting in a completely flat, pliable, white membrane-like material. As the 3:2, 7:6, and 1:1 samples dried, crystallizing drawing forces stressed the material beyond the fiber elongation yield point, resulting in structural failure with the material shearing at the dish rim and propagating into the interior region of the sample. With this drying method, the decreasing silk concentration influenced the material structural integrity and flex strength. Although the 2:1 sample sheared away from the dish rim, there was little evidence of material deformation, with properties similar to the 4:1 and 3:1 samples. The 4:1 and 3:1 matrices retained 98% of the original surface area while the 2:1 mats lost 11.8%±2.7%, as shown in FIG. 4. The 3:2, 7:6 and 1:1 samples shrank 68.8%±9.1%, 65.9%±%4.3 and 63.9%±6.5%, respectively (n=3). The average thickness for each dried set of mats was 31.2±1.8, 28.7±1.2, 24.3±2.3, 25.3±2.3, 20.0±1.4 and 26.0±0.9 microns, respectively, as shown in FIG. 5.

Figure 6A:
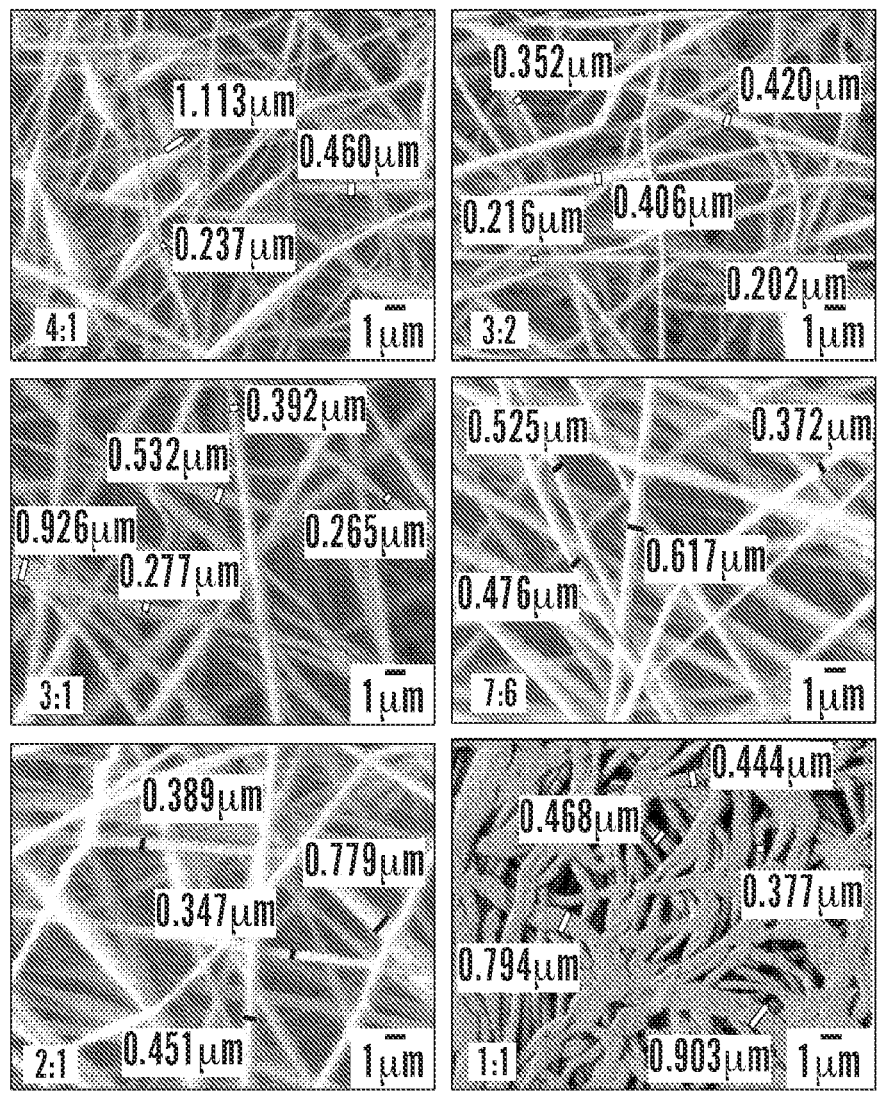
FIGS. 6A and 6B show the FE SEM images of silk material groups prior to methanol treatment at 6.5× magnification. With the increased PEO concentration, fiber beading was reduced over S87P13-S76P24 silk mats. Uniform well-distributed S67P33-S61P39 fibers transition into irregularly shaped melded fibers shown in the dense S57P43 structure.

In the present invention, the resulting fibers of the electrospun silk/PEO blended mats have a substantially uniform diameter distribution throughout the mat structure. The SEM images in FIG. 6A are of all six silk/PEO material groups immediately following the electrospinning process and prior to the saturating methanol and PEO leaching treatments. Overall, these electrospun silk/PEO fibers range from 200 nm to 500 nm in diameter. As reported by Huang et al, 2001, fiber bead formation was increasingly pronounced with decreasing PEO concentration. Wang et al., 2006; Zhou et al., 2000; Huang et al., 12 J. Biomat. Sci. Polym. Ed. 979-93 (2001). Specifically, the 4:1, 3:1, and 2:1 (fibroin:PEO) samples each had bead segments at random positions within the fibers ranging from just over a micron down to 700 nm in width. Beading was minimized on the 3:2 and 7:6 sample sets with well defined fine circular-shaped fibers rendering an ordered appearance throughout the structures. The 1:1 sample set had a unique appearance where the fibers were irregular and non-circular in shape transitioning into a non-uniform, dense mat structure. It is plausible that this transition may be attributed to fiber convergence via liquid-liquid/liquid-solid phase dispersion when congregating on the apparatus ground stage. The 1:1 individual fibers ranged from 300 to 500 nm whereas the melded fibers measured between 700 to 900 nm.

"Constraint-drying technique" or "constraint-drying", as used herein, refers to the process where the silk material is dried while being constrained, such that it dries while undergoing a drawing force. For example, the constraining force may be attributed to the resultant contraction forces which occur as the silk material dries while attached over the mouth of a crystallization dish. As described, these saturated silk materials are initially draped over and attached to the mouth of a crystallization dish. As water molecules evaporate, hydrophobic domains at the surface substrate and throughout the bulk region of the protein initiate the loss of free volume from the interstitial space of the non-woven cast and within bulk region of the material. The loss of free volume causes the material to contract and draw radially towards the rim of the crystallization dish. Attached to the rim of the crystallization dish, the material becomes constrained with the continuous loss of free volume and the fibers become aligned and elongated in the direction of the radial stress. Dependant on silk volume, if the material fibers contract beyond the elongation yield point, material shearing will occur at the material/crystallization dish rim surface interface. Contrary to the constrain-drying method, the air-dried samples in the petri dish continuously contract until dry into twisted, irregular conformations.

Figure 9:
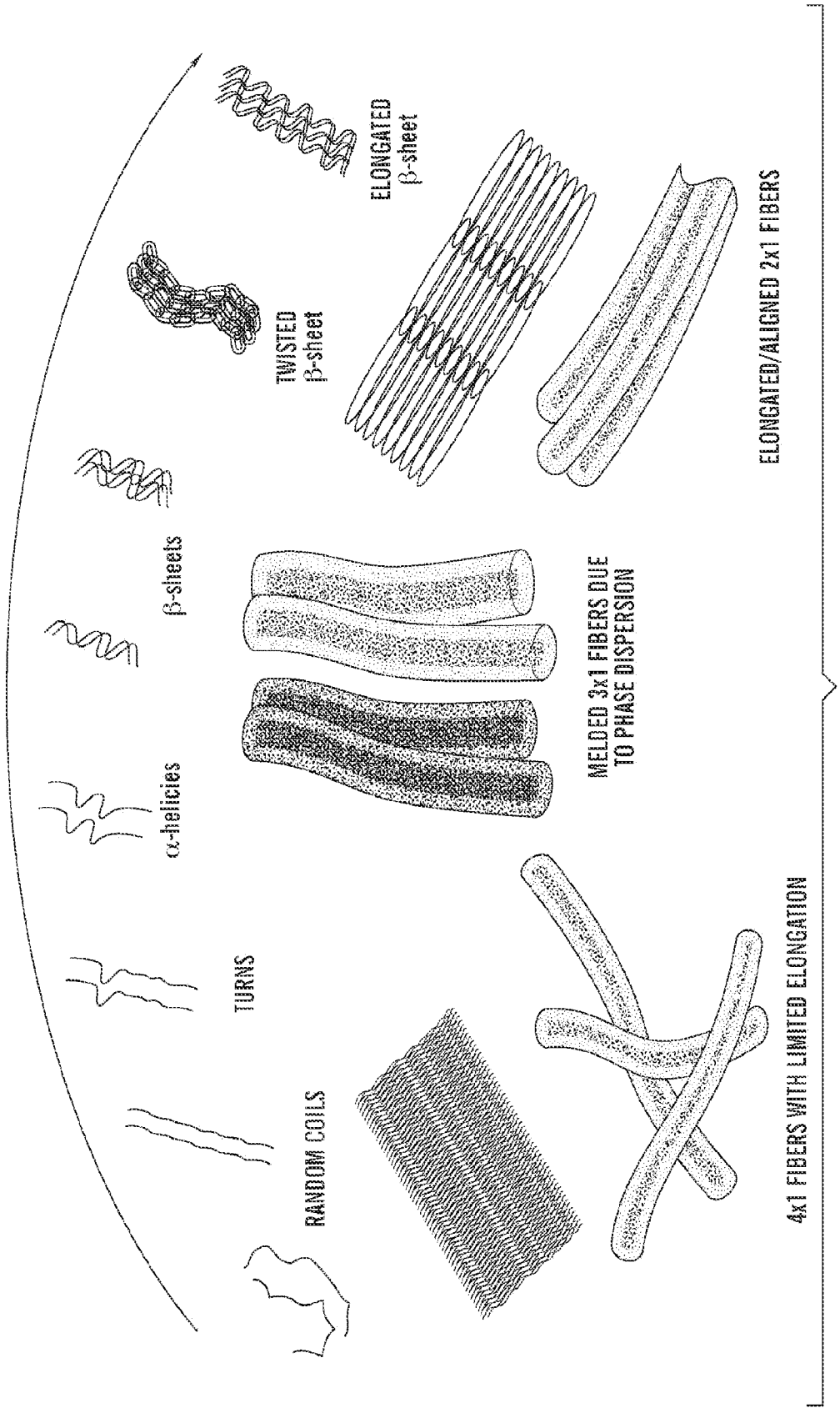
FIG. 9 is a conceptual diagram illustrating the progressive polymer chain and fiber conformations utilizing the crystallization dish drying method. At the top, distributed unaligned secondary structures transition from a hydrophilic environment to aligned protein aggregates driven by hydrophobic interaction. As fibers begin to draw, β-sheets assemble predominately via inter-chain formations and elongate in the direction of radial stress. Fiber formations at the bottom of the diagram reflect the inverse relationship between silk concentration and fiber alignment and elongation.

In one embodiment, the constraint-dry method is performed with controlled evaporation. The method comprises taking electrospun silk/PEO blended mats from a water bath, draping the mats over a crystallization dish, with one-third of the dish filled with water, and placing the dish containing the mats in a desiccator between 20% and 50% Relative Humidity and drying overnight. A conceptual diagram illustrating the progressive polymer chain and fiber conformations utilizing the crystallization dish drying method is shown in FIG. 9. At the top, distributed unaligned secondary structures transition from a hydrophilic environment to aligned protein aggregates driven by hydrophobic bonding. As fibers begin to stretch, water annealed β-sheets assemble via inter-chain vs. intra-chain formations. Fiber formations at the bottom of the diagram reflect the inverse relationship between silk concentration and fiber alignment and elongation.

In one embodiment, the SEM images of silk/PEO blended mats prepared using the constaint-dry method, such as crystallization dish method, as shown in FIG. 7. The silk/PEO blend ratios of the mats prepared are 4:1, 3:1 and 2:1, respectively. The surface topographies reflect a dense, random distribution of fibers throughout each model. Evaluation shows increasing evidence of fiber contraction, elongation, and realignment which occurs with this drying technique. Referencing FIG. 7B, the fibers of the 4:1 mats have a relaxed twisted appearance without any noticeable fiber contraction or alignment. In contrast, the fibers of the 3:1 and 2:1 mats become elongated aligned and attached forming web-like micro textures. Focusing in on fiber formation in FIG. 7C, the elongated fibers in the 3:1 mat form a taut, webbed structure with evidence of phase dispersion between aligned fibers culminating in a liquescent appearance. The webbed structure for the 2:1 fibroin:PEO samples consists of an intertwining network of well defined, elongated, aligned fibers forming rope-like arrangements.

The fiber alignment and elongation manifested through the constraint-drying technique can be attributed to the water annealing properties of silk fibroin. Jin et al., 15 Adv. Funct. Mater. 1241-47 (2005); Agarwal et al., 63 J. Appl. Polym. Sci. 401-10 (1997); Lawrence et al., 43 J. Mat. Sci. 6967-85 (2008); Wong et al., 2006. Acting as a plasticizer within the polymer bulk region, water molecules propagate inter-molecular movement between low cohesive energy polymer chains, promoting polymer fluidity and realignment. As the water molecules evaporate, polymer chains are drawn and orient in the direction of the radial stress originating around the rim of the crystallization dish. With drawn polymer chain alignment, proline folding at the terminus of the amorphous light chain is reduced which promotes an escalation of bilateral inter chain laminar structures and reduction of crystallized intra-chain twisted conformations. Zhou et al., 2000; Liu et al., 9 Biomacromol. 116-21 (2008). Predominate inter chain hydrophobic interaction compresses free volume from the bulk region, influences crystalline secondary structure alignment and transition of amorphous silk I to the crystalline silk II state. Jin et al., 15 Adv. Funct. Mater. 1241-47 (2005); Agarwal et al., 1997; Lawrence et al., 43 J. Mat. Sci. 6967-85 (2008); Wong et al., 82 Appl. Phys. A-Mater. 293-203 (2006). With continued evacuation of water molecules, the bulk volume decreases and contracts until the fibers start to elongate over the mouth of the crystallization dish. As shown in FIG. 9, the combination of these constituents produce mats with elongated aligned fibers with high strength material properties along the fiber axis. Beyond the elongation yield point, shearing deformation takes place within and along the amorphous secondary structures of both heavy and light (H,L) chains.

Figure 7A:
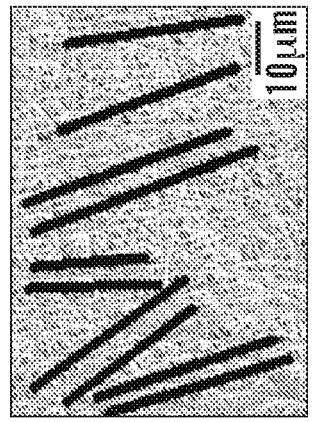
FIGS. 7A-7E are SEM images of methanol-treated silk mats with silk/PEO ratios of 4:1, 3:1 and 2:1, respectively.
Figure 7A:
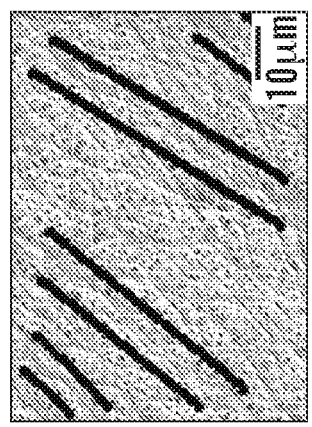
Figure 7A:
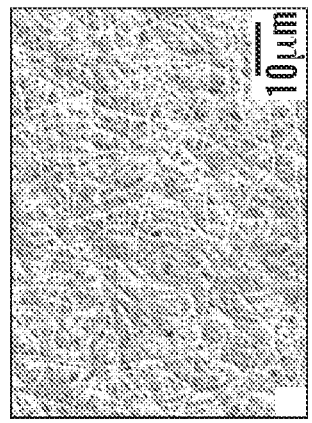
Figure 7B:
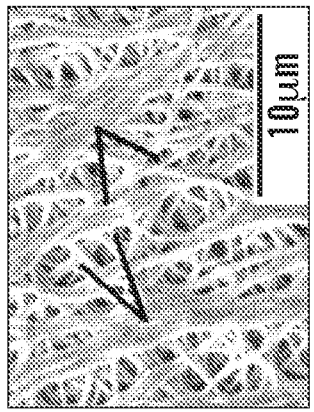
Figure 7B:
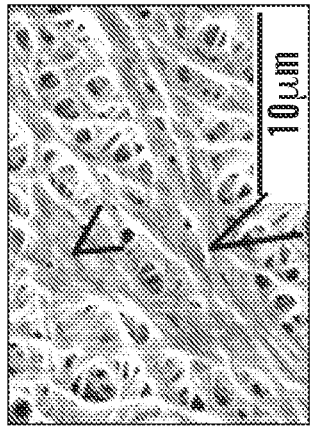
Figure 7B:
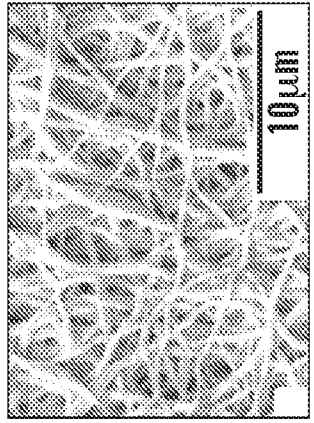
Figure 7C:
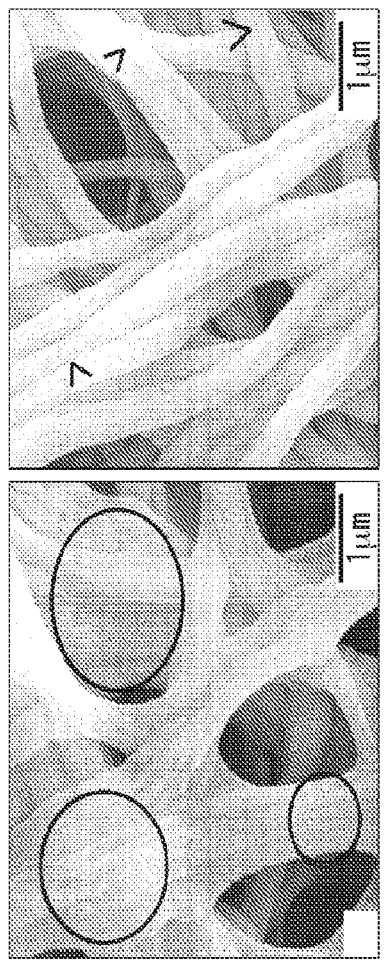
Figure 7E:
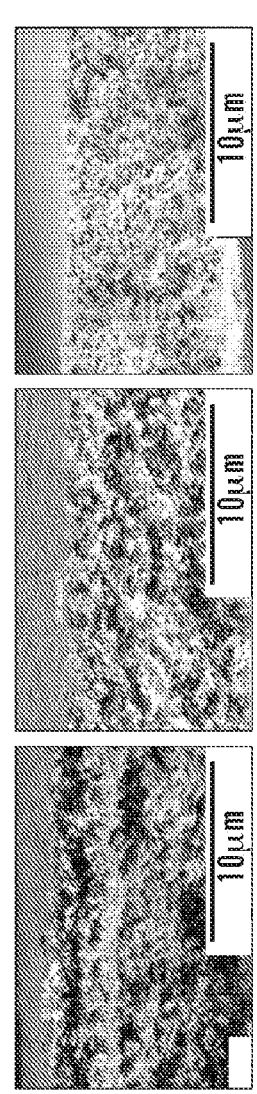
Figure 7D:
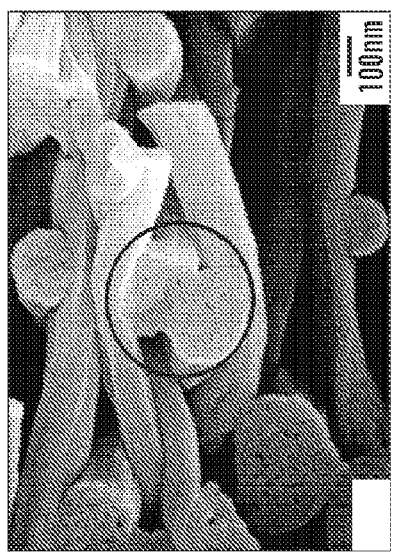

The appearance of macroscopic phase dispersion between aligned 3:1 fibers in FIG. 7C and the 2:1 fibers in FIG. 7D can also be attributed to plasticizing properties of water. Differential scanning calorimetry of water and *B. mori* silk fibroin film systems revealed the glass transition temperature (Tg) of dehydrated silk fibroin decreased from 178° C. to below 40° C. with 20-23 wt % water absorption. Agarwal et al., 1997. Although crystalline conformation influences diluent absorption throughout the biomaterial, the equilibrium water content (EWC) of each silk mat group was greater than 80 wt % (Table 4), indicating considerable hydrophilic interactions; forecasting a reduction in Tg and plausible phase dispersion. Hu et al., 39 Macromol. 6161-70 (2006). Additionally, the interlaced hydrophobic and hydrophilic domains throughout the silk polymer chains result in a dynamic mobile surface substrate as the material transitions from surface-liquid to surface-gas, surface-surface interfaces. Ratner et al., BIOMATS. SCI.: INTRO. MATS. MED. (Acad. Press, NY, 2004; Allcock, INTRO. MATS. CHEM. (Wiley & Sons, Hoboken, N.J., 2008). Specifically, as the diluent evaporates, hydrophilic domains are interchanged with hydrophobic segments at the surface. Factoring in the phase dispersion described above, when this phenomena occurs between interfaced fibers, amorphous secondary structures become interspersed resulting in melded fibers. It is also conceivable that the linear secondary structures between fibers may become aligned forming thermodynamically stable crystalline β-stands. Lawrence et al., 43 J. Mat. Sci. 6967-85 (2008); Fink, 3 Folding & Design R9-R23 (1998).

The silk mats of the invention may have interconnected pores with the pore throat size surface area averaging from about 0.1 to about 1 micron. Cross-sectional views in FIG. 7E reveal different features for silk mats with several different silk/PEO blend ratios. These images show an increased fiber density with decreasing silk concentration; and the fiber aggregation across matrices is also different for silk mats with different silk/PEO blend ratio. The 4:1 blended fibers aggregated in horizontal sheets with numerous large interspatial crevasses. The 3:1 and 2:1 blended fibers demonstrated increased fiber bundling, reflective of fiber contraction and a progressive reduction of interspatial gaps respective of decreasing silk volume. These observations correspond to the decreasing mat thickness respective of silk concentration. The three images in FIG. 7B represent the interconnecting porosity throughout this biomaterial. Pores had a throat size surface area averaging from 294, 201, to 103 nm$^2$ for each matrix, respectively. The descending pore size distribution shown in FIG. 9 corresponds to the increased fiber density seen in cross-sectional views and relates to the assembly of the fibers with respect to decreasing number of bead regions and fiber diameter for the 4:1, 3:1, and 2:1 matrices.

Figure 10:
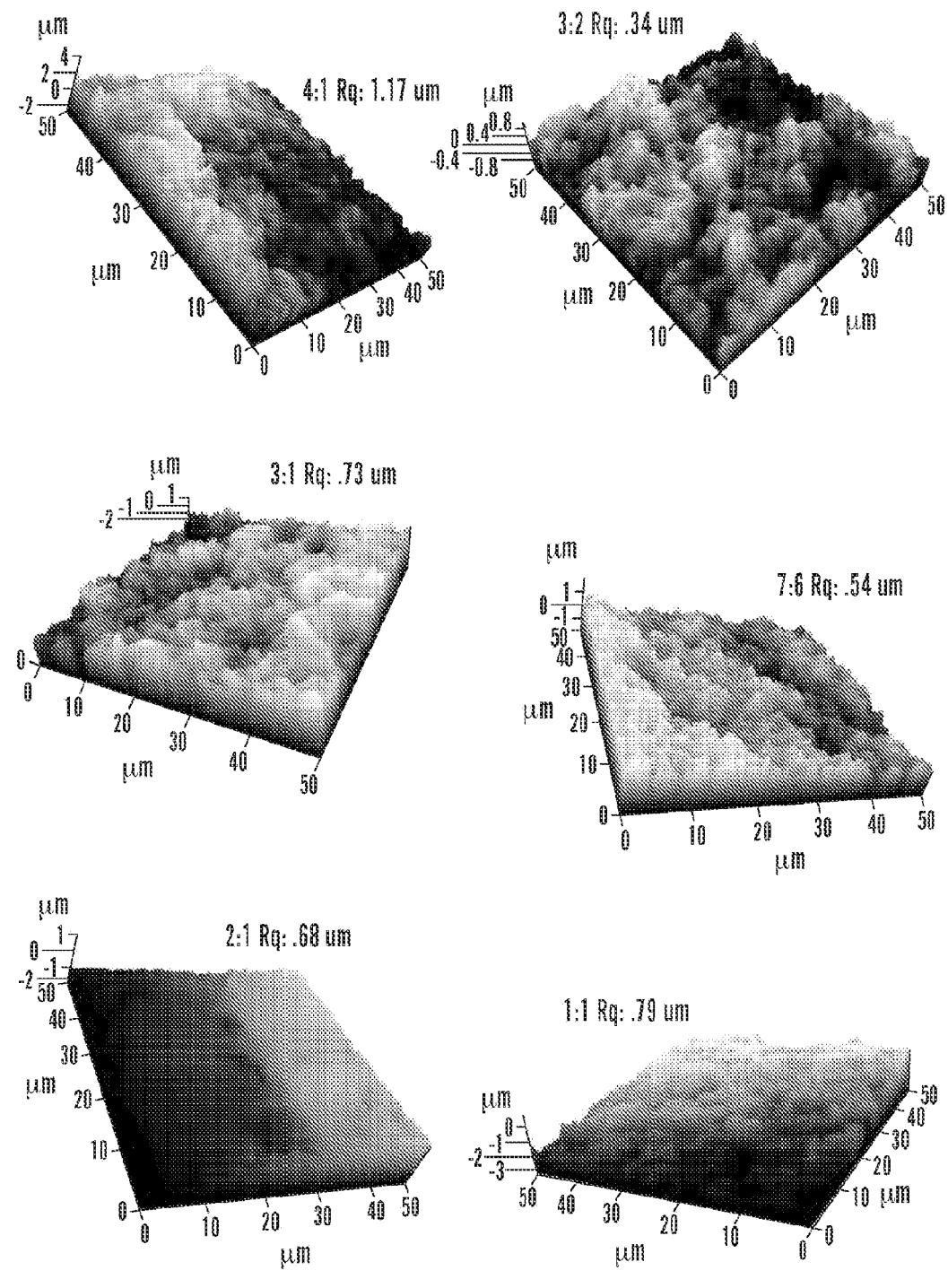
FIG. 10 demonstrates 50×50 micron 3D AFM images and roughness values for silk material groups after methanol treatment. The images were obtained using an Ultrasharp NSC16/AlBS probe in a non-contact mode (resonant frequency: 170 kHz, force constant: 45 N/m).

The material surface roughness influences cellular contact guidance via stress/sheer free planes which facilitate the net force biomechanical equilibrium that controls cell orientation, attachment, growth, and migration. The silk/PEO blended mats of the invention that undergoes constraint-drying treatment have a smaller surface roughness than the silk mats undergoing the air dried methods. AFM images in FIG. 10 display the 3D morphological imagery and sample root-square-mean roughness values for the silk mats of the invention with different silk/PEO blend ratio after drying with the polystyrene-dish air drying method. Regional domain roughness analysis was characterized by the roughness variation throughout the X and Y planes of the image. Overall these silk material systems demonstrated class three surface topographies exhibiting well-defined surface irregularities with roughness values ranging from 500 nm up to 1.4 microns (n=3). The 4:1 and 1:1 samples had a relatively uniform roughness with nano-sized irregularities measuring 1.17±0.00 and 0.78±0.01 microns, respectively. The 3:1, 2:1, and 3:2 samples had a roughness standard deviation between 0.1 and 0.17 microns, ranging from 0.65±0.10, 0.88±0.17, and 0.76±0.16 microns, respectively. The 7:6 mats had the greatest variation in regional roughness averaging 1.01±0.43 microns. AFM roughness evaluation was also performed on the silk/PEO blended mats constraint-dried with the crystallization dish technique. The 4:1, 3:1, and 2:1 samples over a 16×16 micron area have roughness values of 0.66, 0.36 and 0.25 microns, respectively. Although the area size of samples is reduced and sample size are limited (n=1), the roughness of the stretched dried mats are at least 44% flatter than the air-dried mats. The constraint-dried samples appear to decrease linearly in roughness with respect to silk concentration whereas there is no evident trend for the air-dried samples. This observation coincides with the fiber elongation properties of constraint-dried samples compared to the twisted irregularities of air-dried samples.

The electrospun silk/PEO blended mats prepared by the processes of the present invention exhibit good structural, morphological, biofunctional and biocompatible properties suitable for biomaterial application, such as wound dressing. For example, the resulting silk mats of the invention degrade more than about 86% (wt) in less than 14 days; the equilibrium water content of the silk mats of the invention is more than about 82%; the oxygen transmission rate of the silk mats is more than about 15460 cm$^3$/m$^2$/day; and water vapor transmission rate of the silk mats is more than about 1934 g/m$^2$/day.

Figure 12A:
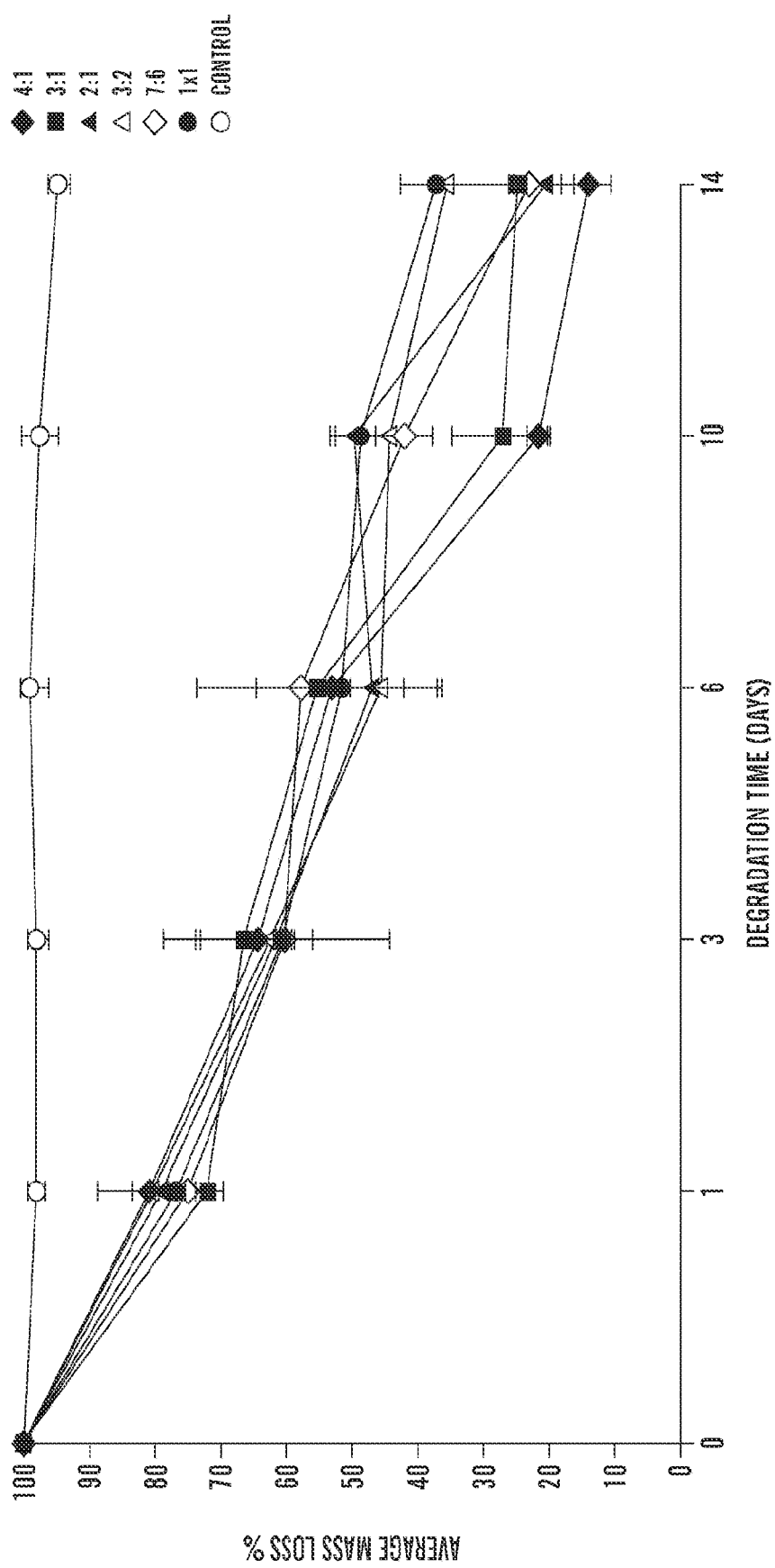
FIGS. 12A-12C are graphs representing in vitro enzymatic biodegradation analysis of silk material groups over 1, 3, 6, 10, and 14 day time points. Three-ply 25±5 mg circular 3.5 cm samples were incubated at 37° C. in a 6 mL solution of 1 mg/mL protease XIV in PBS at pH 7.4. Control samples were immersed in PBS without enzyme. Enzymatic and control solutions were replenished daily.

The embodiments of the present invention provide for silk materials with enzymatic biodegradation to facilitate epithelialization with time release biotherapies. The enzymatic biodegration of electrospun silk/PEO blended mats with different blend ratios were evaluated over more than 14 days. The in vitro biodegradability revealed linear degradation for all the material groups across all time points resulting in 22.6%±3.4% degradation after 1 day and up to 74.0%±8.8% material loss after 14 days for each group, respectively, as shown in FIG. 12A. The data allows the inference that up until 6 days, degradation rates for all blends were relatively close at 48.2±4.6%. After day 10, a 27% weight loss differential was recorded for different material groups with the silk/PEO blend ratio ranging from 4:1 (78%) to 1:1 (51%). After 14 days, enzymatic degradation ranged from 85.6±3.8% (4:1) down to 62.5±5.2% (1:1). Morphologically, upon visually inspection, all the materials systems primarily degraded via surface erosion over the first 6 days. After the 10-day time point, the 4:1 and 3:1 samples demonstrated increased fiber cleavage degradation resulting in mat fraying, fragmentation, and disintegration into particulate debris. The biodegradation behavior of the 4:1 and 3:1 samples can be attributed to the enzymatic access to the interior fiber structure of the mat due to increased fiber size, mat porosity and decreased fiber density properties of these blends.

Figure 12B:
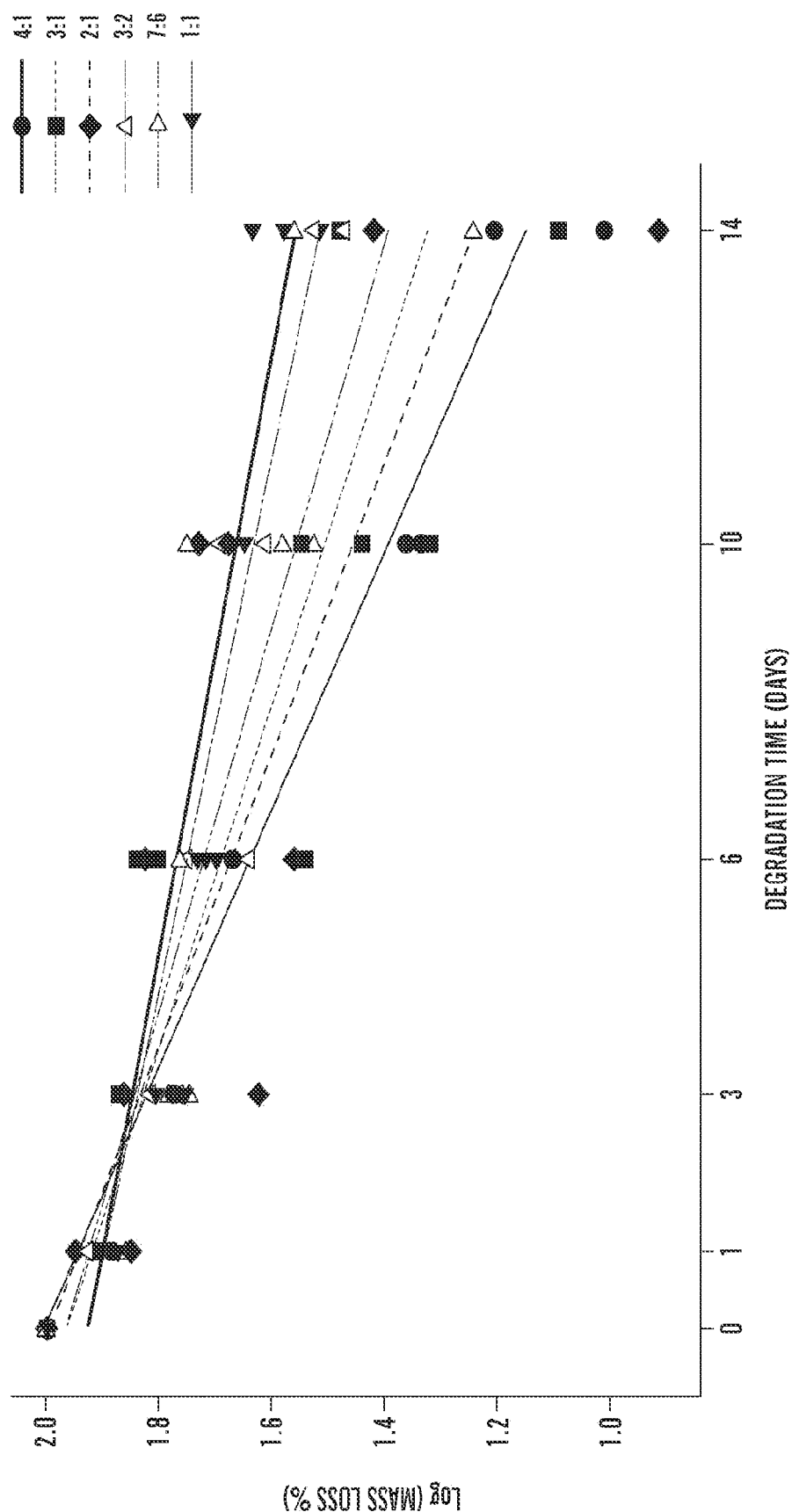
Figure 12C:
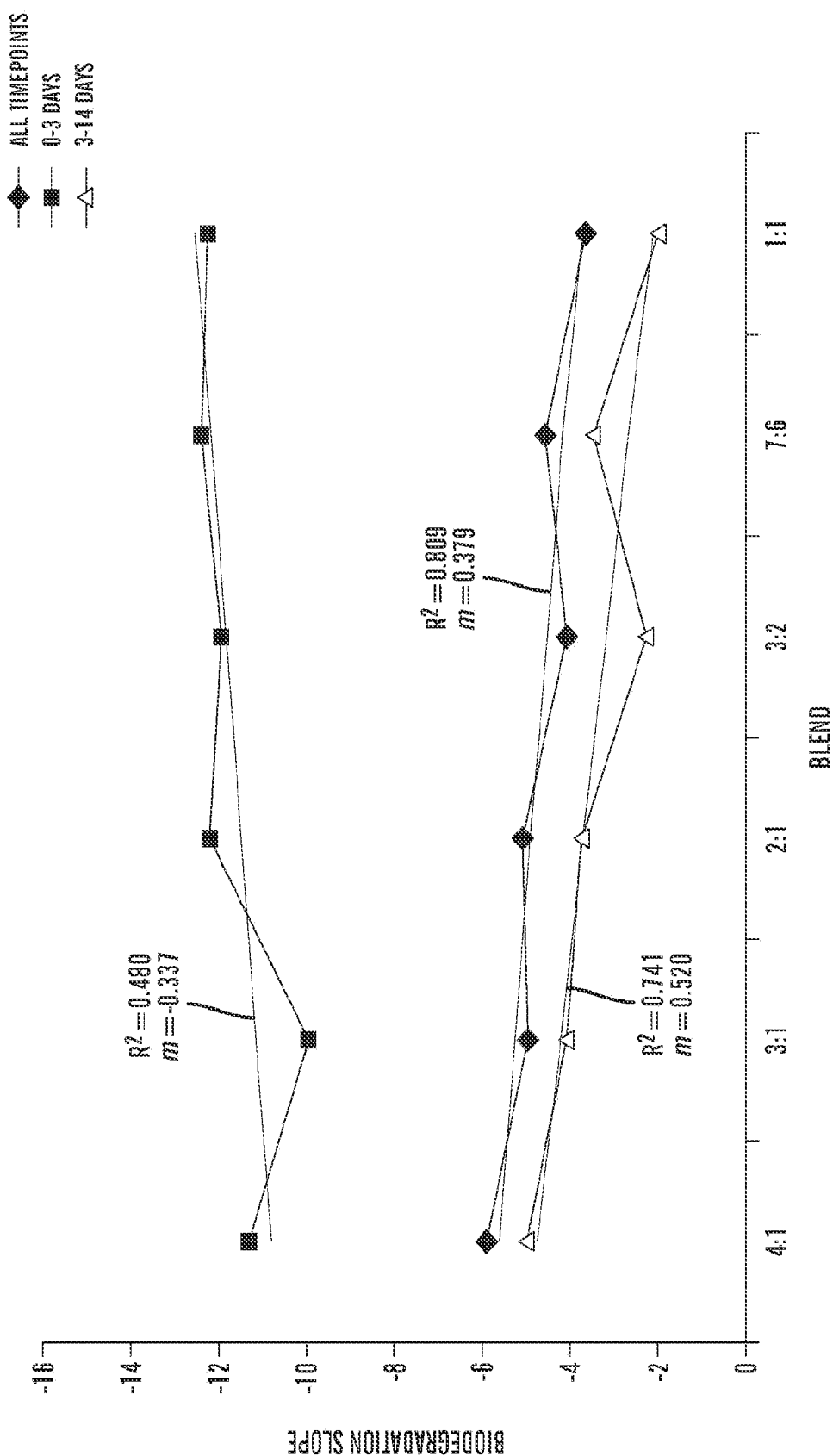

Linear regression analyses were performed across all samples for each silk/PEO blend ratio using Minitab® 15.2.30. Referencing the scatter plot in FIG. 12B, the logarithmic transformation executed over each material group revealed a distinct transition point for all material groups just prior to the day three degradation time point. Regression analysis was then performed for each material group over all time points, from the start to day-3 time points and between day 3 and day 14 time points. As displayed in FIG. 12C, the degradation slopes for all material groups substantially altered after day three. From the start to day 3, the enzymatic degradation rate averaged at −11.68±0.91 slope units; after day 3 up until day 14, the rate of degradation leveled off to −3.41±1.12. During the initial degradation phase, amorphous regions degrade at an accelerated rate compared to internal crystalline regions. This hypothesis may be verified employing Fourier self-deconvolution (FSD) on the infrared absorbance spectra of these silk materials at the start and after 3 days of enzymatic degradation. Hu et al., 2006.

Normal human skin regenerates in about 21 days. The present invention allows design of the matrix to correspond to a desired degradation rate by, for example, comparing the time for protease to break down the silk materials into fragments in order to facilitate epithelialization with time release biotherapies. The results show that after 14 days, 86% of the 4:1 silk/PEO blend mats had dissolved away, which compares favorably with the chitosan/poloxamer dressing which degraded 82% after 14 days when exposed to lysozyme, and to PLGA/PLLA (90/10) with 20% degradation after 14 days in PBS. Degradation rates in vivo may also be addressed, as enzyme levels may vary, and is has been shown that silk biomaterials can degrade in weeks to years in vivo depending on material format, location, and related variables. Wang et al., 2008.

The silk materials produced by the processes of the present invention may be used in a variety of medical applications such as wound closure systems, including vascular wound repair devices, hemostatic dressings, full thickness burn wound dressing, patches and glues, sutures, drug delivery and in tissue engineering applications, such as, for example, scaffolding, ligament prosthetic devices and in products for long-term or bio-degradable implantation into the human body. A exemplary tissue engineered scaffold is a non-woven network of electrospun fibers.

Additionally, these biomaterials can be used for organ repair replacement or regeneration strategies that may benefit from these unique scaffolds, including but are not limited to, spine disc, cranial tissue, dura, nerve tissue, liver, pancreas, kidney, bladder, spleen, cardiac muscle, skeletal muscle, tendons, ligaments, and breast tissues.

In one embodiment, the present invention provide for silk materials with useful properties in a full thickness burn wound dressing, including the ability to process the material into a bandage, manage wound site edema and $O_2/CO_2$ gas permeation, and the ability to administer time synchronized antibiotic, immunological, and tissue regeneration biotherapies. In the present invention, with constraint-drying technique employed, it was discovered that silk concentration played a major role in properties including fiber thickness, density, orientation, phase dispersion, porosity and mat thickness. For example, the electrospun silk mats with the silk/PEO blend ratio from 4:1 to 2:1 are used and possess useful physical properties in a full thickness wound dressing displaying a pliable membrane-like material with minimal surface area loss and exhibit pore throat surface area sizes below 0.3 $\mu m^2$ providing an impermeable barrier to gram negative bacilli and gram positive cocci sepsis-initiating bacterial pathogens.

The absorption and equilibrium water content (EWC) properties of the materials play an role in controlling the accumulation of wound exudates, which can provide a feeding bed for bacteria. In one embodiment, the overall absorbability and EWC performance for the silk material with a silk/PEO blend ratio ranging from 4:1 to 1:1 were relatively close within each group, ranging from 400% to 700% and 82% to 86%, respectively. Considering the difference in fiber density across the silk material groups, each material group with different blend ratio still displayed similar swelling qualities. Comparing these models with other wound dressing candidates in Table 2, the silk mats of the invention perform as well as the sponge-like natural chitosan based dressings. Although the chitosan/poloxamer dressing candidate have good absorption and EWC properties, the all-natural, FDA-approved silk material systems of the present invention offer biocompatibility and remarkable mechanical robustness in comparison to these other systems.

TABLE 2

Average water absorption and equilibrium water content comparison between chitosan derivatives based wound dressings and silk material systems of the invention.

| Dressing Biomaterial | Absorption (%) | Equilibrium Water Content (%) |
|---|---|---|
| Silk Models | 460-610 | 82-86 |
| Bilayer Chitosan* | 280-950 | NA |
| Asymmetric Chitosan** | 130-760 | NA |
| Chitosan Polymer*** | 1700-2400 | 94-96 |

*Gibran et al., 70 J. Surg. Res. 1-6 (1997);
**Quynh et al., 2007;
***Wu & Wu, 2006.

In order to maintain homeostatic body temperature, normal skin permeates body fluid at a rate of 204 g/m² per day. Lamke et al., 3 Burns 159-65 (1977). It has also been reported that the evaporative water loss for a full thickness granulating wound is 5,138 g/m² per day, and that an ideal full thickness wound dressing ought to have a water vapor transmissibility rate (WVTR) of 2,000-2,500 g/m² per day to permit adequate moisture level while preventing excessive dehydration. Queen et al., 1987. In one embodiment, the saturated and dry silk materials in the present invention have WVTRs of 1,977±35 and 1,469±81 g/m²/day at 37° C. and 50% RH which performed comparatively to the chitosan dressings which ranged from 1,180 to 2,830 g/m²/day at relative temperature and humidity as shown in detail in Table 3. Considering the thickness of the electrospun silk mats of the present invention (30-80 microns) versus the sponge-like bilayer and asymmetric chitosan dressings (60-800 microns), it is plausible that a multi-layered silk dressing can be tailored to achieve the desired WVTRs stated above. Additionally, oxygen transmissibility rates from 25,000 down to 7,800 cm³/m² per day can be attributed to the fiber size, porosity and fiber density of each material group revealed in the SEM photos, as shown in FIG. 7. The hydrophobic nature of this biomaterial facilitates the ability to tailor these mats to an ideal thickness for optimum gas and water vapor transmission performance in balancing wound exudate drainage, edema and dehydration.

TABLE 3

Average water vapor and oxygen transmissibility rate comparison between chitosan derivatives-based wound dressings and the silk material systems of the present invention.

| Dressing Biomaterial | Water Vapor Transmissibility Rate g/(m² · d) | Oxygen Gas Transmission Rate cm³/(m² · d) | Material Thickness (microns) |
|---|---|---|---|
| Silk Models | 1400-2000 | 7.8-25.0E+03 | 6.41E−02 |
| Bilayer Chitosan* | 1187-1230 | 4.6-18.4E+05 | 5.63E−02 |
| Asymmetric Chitosan** | 2100-2800 | 2.87-84.2E+05 | 3.96E−02 |
| B-chitin*** | 2400-2800 | NA | 4.27E−02 |

*Gibran et al., 70 J. Surg. Res. 1-6 (1997);
**Quynh et al., 2007;
***Hu et al., 2006.

The network of interconnecting pores throughout the silk matrices proves a useful material system for the absorption of water into the interstitial spaces of the non-woven structure. The modified electrospun silk fibers (silk/PEO blend ratio of 4:1) have a porosity of up to 68%. Wang et al., 37 Macromol. 6856-64 (2004). Increased surface area promotes water absorption into the bulk region of the biopolymer as energy is minimized by polar water molecules bonding to hydroxyl, carboxyl, and amino groups residing within the hydrophilic regions of both heavy and light chains. Swelling occurs as miscible diluent molecules flow between polymer chains generating free volume. Air dried 2.8 cm electrospun silk mats with silk/PEO blending ratio of 4:1, 3:1, 2:1, 3:2, 7:6, and 1:1 were punched from 10 cm diameter mats. Referencing Table 4, absorption ranged from 461% to 613%, with all silk material groups averaging 551%±54%. In addition, although the average dry weight for each silk model linearly decreased from 22.5 mg (silk/PEO blend ratio of 4:1) down to 13.6 mg (silk/PEO blend ratio of 1:1), the equilibrium water content remained relatively constant at 84%±1% for all the material systems. The data suggest that water absorption is independent of fiber diameter, density, porosity and secondary structure assembly properties of each silk concentration.

TABLE 4

Average water absorption and equilibrium water content measurements for electrospun silk/PEO blended mats immersed in de-ionized water for 24 hrs. (±values = SD, n = 6).

| Blend (Silk Fibroin: PEO) | Dry Weight (mg) | Saturated Weight (mg) | Equilibrium Water Content % | Absorption (%) |
| --- | --- | --- | --- | --- |
| 4:1 | 22.1 ± 6.5 | 121.8 ± 25.3 | 82 ± 3 | 461 ± 82 |
| 3:1 | 21.5 ± .30 | 148.0 ± 18.8 | 85 ± 1 | 593 ± 85 |
| 2:1 | 14.2 ± 1.7 | 90.7 ± 16.1 | 84 ± 2 | 538 ± 84 |
| 3:2 | 14.4 ± 0.8 | 90.2 ± 5.6 | 84 ± 1 | 530 ± 84 |
| 7:6 | 14.1 ± 0.7 | 94.3 ± 13.8 | 85 ± 2 | 569 ± 85 |
| 1:1 | 13.6 ± 3.8 | 93.9 ± 12.7 | 86 ± 2 | 613 ± 86 |

Figure 11:
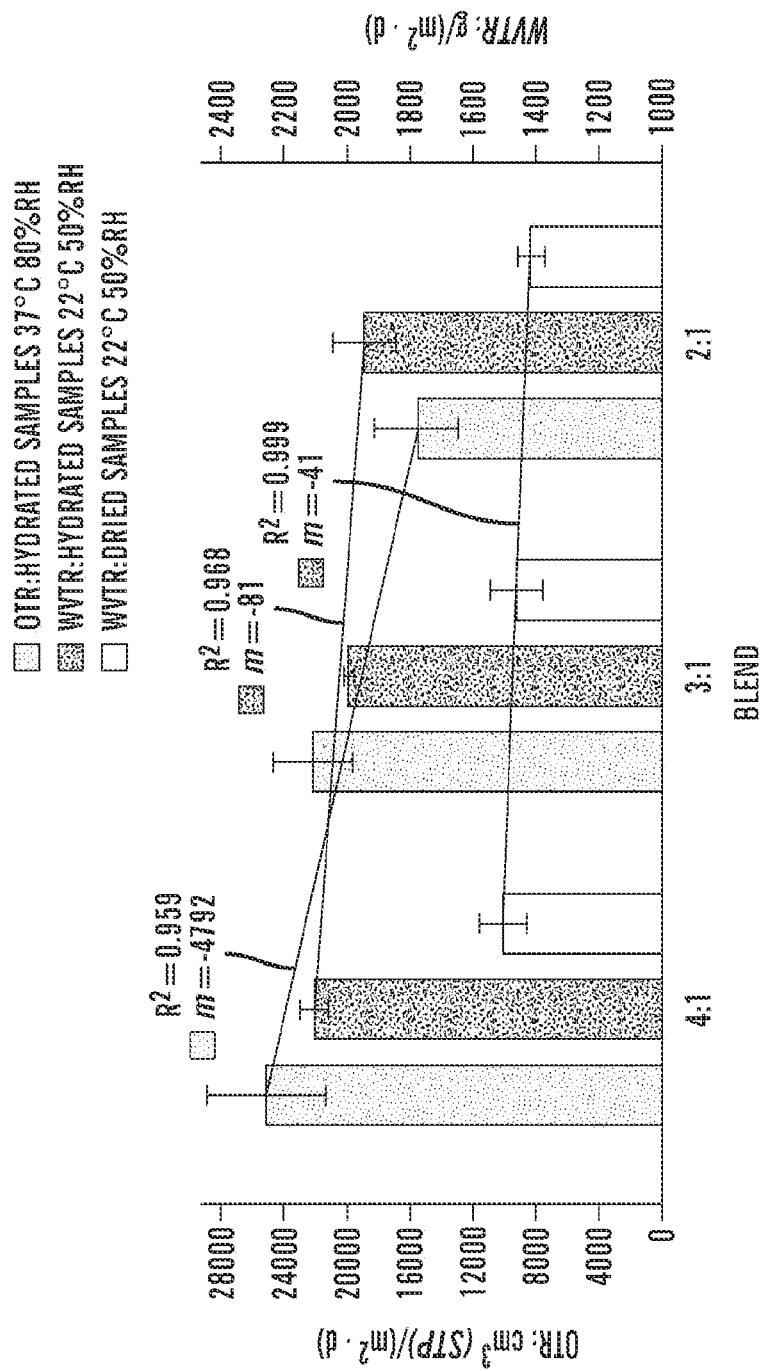
FIG. 11 represents oxygen and water vapor transmissibility performance for 4:1, 3:1 and 2:1 silk material systems under varying environmental conditions. Linear curve fit analysis was executed over the average OTR and WVTR measurements across all material groups (SD±%, n=3). Slope (m) and $R^2$ values indicate a linear reduction of OTR and WVTR performance across all material groups. Although OTR $R^2$ values disclose minimal divergence for OTR measurements across material groups, the standard deviation within each group ranged from ±14.6, 11.2, and 16.9 percent, respectively.

A dressing that promotes oxygen/carbon dioxide gas exchange will reduce wound acidity, inhibit anaerobic bacterial infection, and thus form an environment which promotes wound healing. Mi et al., 22 Biomats. 165-73 (2001); Mi et al., 59 J. Biomed. Mat. Res. 438-49 (2002). Displayed in Table 5, The average Oxygen Transmission Rates (OTRs) of samples evaluated under hydrated conditions (37° C. and 80% RH) exhibited average OTRs from 25,000 $cm^3/m^2/day$ for the 4:1 samples down to 7,800 $cm^3/m^2/day$ for the 1:1 samples. These decreasing OTRs can be attributed to the decreasing fiber size, pore throat size, and increased fiber density of the respective silk material groups. As previously stated, the 4:1, 3:1, and 2:1 models had micron plus fiber diameters with bead regions forming a porous scaffold with a loosely distributed fiber density. The 3:2 and 7:6 fibers had smaller diameters ranging between 200 nm and 500 nm, exhibiting increased fiber density and decreased mat porosity. Additionally, phase dispersed 1:1 fibers formed sheets of fibroin with reduced porosity and generating a crystalline-amorphous glass barrier. In contrast, all saturated and air dried samples for each group of materials tested at 37° C. and 50% RH exceeded the 100,000 $cm^3/m^2/day$ analyzer threshold prior to the completion of one 15 minute interval of testing. As would be expected, these results reflect that in a dry or near dry state these porous material have a greater oxygen permeation rate than when oxygen is diffused through water molecules residing in the interstitial space and bulk region of a saturated non-woven fabric. Linear curve analysis in FIG. 11 discloses an OTR reduction of 9,600 $cm^3/m^2/day$ from the 4:1 to the 2:1 silk blend matrices.

TABLE 5

Average oxygen transmissibility rates for saturated electrospun silk/PEO blended mats were measured with the Illinois Instruments 8001 Oxygen Permeation Analyzer at 37° C. at 80% RH.

| Blend Fibroin: PEO | Oxygen Gas Transmission Rate | Thickness (μm) | Oxygen Transmission per mm Thickness |
| --- | --- | --- | --- |
| 4:1 | 25048 ± 3651 | 81.7 ± 7.5 | 2046 |
| 3:1 | 21972 ± 2465 | 77.5 ± 10.5 | 1703 |
| 2:1 | 15459 ± 2610 | 66.7 ± 5.1 | 1031 |
| 3:2 | 16777 ± 2555 | 53.3 ± 8.1 | 894 |
| 7:6 | 12089 ± 6136 | 46.7 ± 5.1 | 565 |
| 1:1 | 7820 ± 6898 | 30.0 ± 6.4 | 235 |

Oxygen permeability ($PO_2$) and oxygen permeability coefficient ($P'O_2$) values were calculated in accordance with ASTM 3985-05. (±values = SD, n = 3).
Oxygen Gas Transmissibility Rate: $O_2GTR$: $cm^3/(m^2 \cdot d)$; Oxygen Transmission per Unit Thickness: $cm^3/(m^2 \cdot d)/unit$ thickness The water vapor transmissibility of a full thickness wound dressing plays an important role in controlling the evaporation of body fluids at the wound site. A wound dressing exhibiting excessive water vapor transmissibility properties can invoke hypovolemia, hypothermia, and hypertension. Peppas, HYDROGEL MED. & PHARM. II & III (CRC Press, Boca Raton, Fla., 1987); Beers et al., 2006. Water vapor transmissibility rates (WVTR) were calculated over 24 hours for 25 $cm^2$ stretch-dried 4:1, 3:1, and 2:1 silk/PEO mats. Efforts to ascertain WVTRs for 3:2, 7:6, and 1:1 mats were unsuccessful due to the material deformation during drying phases. Constraint-dried materials were evaluated in both hydrated and dry states. WVTRs for saturated and dry 4:1, 3:1, and 2:1 material groups averaged 1,977±35 $g/m^2/day$ for saturated and 1469±81 $g/m^2/day$ for dry, as shown in Table 6. Saturated samples outperformed dry samples, most likely due to direct liquid-membrane-gas interface versus the liquid-gas-membrane-gas interface. The hygroscopic properties of the hydrated mats enabled expedient presentation of water molecules to the biomaterial surface-gas interface promoting thermodynamic reaction and accelerated evaporation. As displayed in FIG. 11, WVTRs across all three silk concentrations were relatively the same, with negligibly descending variation of 162 $g/m^2/day$ and 82 $g/m^2/day$ attributed to fiber size, mat density, porosity and secondary structure properties.

TABLE 6

Average water transmissibility rates for saturated and dry 4:1, 3:1 and 2:1 constraint-dried silk/PEO matrices were measured with a Perm Cup in accordance with ASTM D1653 folloing the water cup method at 22.8 ± 0.6° C. and 50% ± 2% RH, after 24 hrs. (±values = SD, n = 3).

| Blend | Saturated WVTR $(g/(m^2 \cdot d))$ | Dry WVTR $(g/(m^2 \cdot d))$ |
| --- | --- | --- |
| 4:1 | 2097 ± 44 | 1495 ± 75 |
| 3:1 | 1898 ± 24 | 1456 ± 86 |
| 2:1 | 1934 ± 98 | 1413 ± 42 |

Some embodiments of the invention also relates to a method of promoting wound healing comprising contacting a wound with at least one electrospun silk mat comprising a silk fibroin protein, a polyethylene oxide (PEO), and at least one active agent. The electronspun silk mat has a silk fibroin protein/PEO blend ratio from about 2:1 to about 4:1 (or silk percentage is about 75% w/w to 90% w/w); and the silk mat has a thickness of about 20 to 80 about microns.

The present invention provides for electrospun silk/PEO materials that are suitable for biomedical application such as effective wound dressings. The physical and bio-functional properties of electrospun silk/PEO matrices were evaluated to assess structural, morphological and biocompatibility characteristics related to wound dressings. For example, the properties such as the absorption, water vapor transmission, oxygen permeability, and biodegradability bio-functional properties are useful for wound dressing applications. Variations in silk/polyethylene oxide (PEO) content were used to generate different matrices in terms of morphology and structure. Applying two-fluid silk/PEO electrospinning techniques, large confluent silk mats were produced and surface texture and bulk properties were quantified: including fiber structure, topography, absorption, water WVTR, oxygen permeation, and biodegradability. In the hydrated state, all material groups exhibited absorbability and VTR suitable for wound healing. Oxygen transmission rates (OTR) suggested oxygen/carbon dioxide gas exchange features suitable for wound sites. In vitro enzymatic biodegradation identified degradation of 23%±3% of initial weight for 1 day and up to 74±9% for 14 days. Multiple drying methods were explored to address material properties related to the storage and distribution of such wound mat systems. Employing controlled evaporation and constraint-drying techniques, silk concentration was a determining factor in the properties of each matrix, influencing fiber elongation, alignment, density, porosity and phase dispersion. The electrospun silk/PEO mats with a silk/PEO blend ratio of 2:1 to 4:1, treated with controlled evaporation and a constraint-drying technique, demonstrated particularly suitable properties relevant to biomaterial systems with potential utility for wound dressings. These silk material systems may be useful for antibiotic delivery, macrophage response, fibroblast/keratinocyte cell and cytokine impact, and related biological issues.

Particular embodiments of the invention are described in non-limiting examples.

The present invention may be as defined in any one of the following numbered paragraphs:

1. A process for producing a silk mat, comprising:
    blending a polyethylene oxide (PEO) with an aqueous silk fibroin solution;
    electrospinning the blended solution, thereby forming a silk protein/PEO blended mat; and
    constraint-drying the electrospun silk mat.
2. The process of paragraph 1, further comprising treating the electrospun silk mat with alcohol.
3. The process of paragraph 1 or 2, further comprising extracting the PEO from the silk mat.
4. The process as in any one of paragraphs 1-3, further comprising embedding at least one active agent in the silk mat.
5. The process of paragraph 4, wherein the active agent is a therapeutic agent or a biological material, selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and combinations thereof.
6. The process of paragraph 5, wherein the active agent is a cell selected from the group consisting of progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, precursor cells, and combinations thereof.
7. The process of paragraph 6, the active agent further comprises a cell growth media.
8. The process of paragraph 6, wherein the active agent is an antibiotic.
9. A silk material prepared from the process comprising:
    blending a polyethylene oxide (PEO) with an aqueous silk fibroin solution;
    electrospinning the blended solution, thereby forming a silk protein/PEO blend mat; and
    constraint-drying the electrospun silk mat.
10. A silk material encapsulating at least one active agent for dressing a wound to promote wound healing prepared from the process comprising:
    blending a polyethylene oxide (PEO) with an aqueous silk fibroin solution comprising at least one active agent;
    electrospinning the blended solution, thereby forming a silk protein/PEO blend mat encapsulating the active agent(s); and
    constraint-drying the electrospun silk mat encapsulating the active agent(s).
11. The silk material of paragraph 10, wherein the active agent is a therapeutic agent or a biological material, selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and combinations thereof.
12. The silk material of paragraph 11, wherein the active agent is a cell selected from the group consisting of progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, precursor cells, and combinations thereof.
13. The silk material of paragraph 12, the active agent further comprises a cell growth media.
14. The silk material of paragraph 12, wherein the active agent is an antibiotic.
15. The silk material as in any one of paragraphs 9 to 14, wherein the electrospun silk mat is further treated with alcohol.
16. The silk material as in any one of paragraphs 9 to 15, wherein the PEO is extracted from the electrospun silk mat.
17. An electrospun silk material comprising a silk fibroin protein ranging from about 50 wt % to about 100 wt %, wherein the electrospun silk mat has a thickness of about 20 microns to 80 about microns.
18. The electrospun silk material of paragraph 17, wherein the content of silk fibroin protein in the electrospun silk mat ranges from about 75 wt % to about 90 wt %.
19. The electrospun silk material of paragraph 17 or 18, further comprising a blend of a polyethylene oxide (PEO) in the electrospun silk mat, wherein the content of PEO in the electrospun silk mat ranges from about 0 wt % to about 50 wt %.
20. The electrospun silk material of paragraph 19, wherein the content of PEO in the electrospun silk mat ranges from about 10 wt % to about 25 wt %.
21. The silk material as in any one of paragraphs 17 to 20, further comprising at least one active agent.
22. The silk material of paragraph 21, wherein the active agent is a therapeutic agent or a biological material, selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and combinations thereof.
23. The silk material as in any one of paragraphs 17 to 22, wherein the silk mat has a thickness of about 20-30 microns.

24. The silk material as in any one of paragraphs 17 to 23, wherein the silk mats have interconnected pores with the pore throat size surface area averaging from about 0.1 to about 0.3 microns.
25. The silk material as in any of the paragraphs 9 to 24, wherein the resulting silk mat has a water absorption content of more than about 460%.
26. The silk material as in any of the paragraphs 9 to 25, wherein the resulting silk mat has an equilibrium water content more than about 82%.
27. The silk material as in any of the paragraphs 9 to 26, wherein the resulting silk mat has an oxygen transmission rate of more than about 15460 $cm^3/m^2/day$.
28. The silk material as in any of the paragraphs 9 to 27, wherein the resulting silk mat has a water vapor transmission rate of more than about 1934 $g/m^2/day$.
29. A method of promoting wound healing comprising contacting a wound with at least one electrospun silk mat comprising a silk fibroin protein and, optionally, at least one active agent;
wherein the silk fibroin protein ranges from about 50 wt % to about 90 wt %,
wherein the silk mat has a thickness of about 20 micron to about 80 micron;
wherein the silk mat has a water absorption content of more than about 460%, or equilibrium water content more than about 82%; and
wherein the resulting silk mat has an oxygen transmission rate of more than about 15460 $cm^3/m^2/day$.
30. The method of paragraph 29, wherein the silk fibroin protein ranges from about 75 wt % to about 90 wt %.
31. A method of promoting wound healing comprising contacting a wound with at least one electrospun silk mat comprising a silk fibroin protein, a polyethylene oxide (PEO) and, optionally, at least one active agent;
wherein the silk/PEO blend ratio is from about 4:1 to about 2:1;
wherein the silk mat has a thickness of about 20 micron to about 80 micron;
wherein the silk mat has a water absorption content of more than about 460%, or equilibrium water content more than about 82%; and
wherein the resulting silk mat has an oxygen transmission rate of more than about 15460 $cm^3/m^2/day$.
32. The method as in any one of paragraphs 29 to 31, wherein said silk mat has a water vapor transmission rate of more than about 1934 $g/m^2/day$.
33. The method as in any one of paragraphs 29 to 32, wherein the active agent is a therapeutic agent or a biological material, selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and combinations thereof.

EXAMPLES

Example 1

Materials. Cocoons of *Bombyx mori* silk (Tajima Shoji Co., Yokohama, Japan) were prepared to generate an 8 wt % silk solution. Wang et al., 2006. Six silk materials were prepared with 4:1, 3:1, 2:1, 3:2, 7:6, and 1:1 w/w silk:PEO (920,000 g/mol) ratio solutions. The 4:1, 3:1, and 2:1 blends contained 5% PEO, while the 3:2, 7:6, and 1:1 blends contained 6% PEO in order to maintain the minimum 7.2% silk/PEO polymer concentration necessary for viscoelastic and surface tension properties to generate stable fluid jets during electrospinning. Jin et al., 3 Biomacromol.s 1233-39 (2002).

The electrospinning apparatus built for this research followed previously published procedures (Wang et al., 2002) employing a high voltage power supply (Gamma High Voltage Research ES-30P, Ormond Beach, Fla.), a 10 to 60 ml syringe pump (Braintree Scientific 8000, Braintree, Mass.), potential and ground stages, 1.5 mm polyethylene tubing and a 16 gauge 5.08 cm steel capillary tube. See, e.g., WO 2004/0000915; WO 2004/062697.

The silk/PEO solution was pumped through polyethylene tubing from the syringe pump to the 12 kV DC charged steal capillary tube inserted in the potential plate. Id.; Reneker & Yarin, 49 Polymer 2387-25 (2008); Jin et al., 2002. Electrospun fibers were collected on a ground stage, placed approximately 17 cm below the potential plate and located approximately 2 cm to 3 cm beyond the vertical fall line of the capillary tip. Based on these weight ratios and the equation:

$$\text{Silk \%} = \frac{\text{Silk \%}}{\text{Silk \% + PEO \%}} \quad \text{(Equation 1)}$$

The w/w silk percentage for each model equated to 86.5%, 82.8%, 76%, 70.6%, 65.1% and 61.5%, respectively. Solution viscosities were determined with a Brookfield HATD viscometer (Brookfield Engineering Laboratories, Inc., Stoughton, Mass.) using a #5 spindle at 69° F. equaling 128, 152, 240, 424, 768, and 1120 mPa-S, respectively. Mats of 16.5 cm and 10 cm diameter were electrospun for each of the six material groups at room temperature (RT) with a relative humidity below 60% to evaluate differences in mat thickness due to the electrospinning process.

Drying Methods. Drying techniques were employed to evaluate the physical properties of the silk electrospun material mats. In an air-dry method, 3.5 cm, 2.8 cm and 2.2 cm diameter samples were punched from 10 cm diameter mats immersed in water. After being pressed between weighing paper (VWR, West Chester, Pa.), the samples were placed vertically on the side wall of a polystyrene Petri-dish until nearly dry. Thereafter the samples were periodically repositioned to prevent sticking and dried for 24 hours at RT.

In a constraint-dry method, large 16.5 cm diameter samples were taken from a water bath and draped over the mouth of a 125×65 mm crystallization dish ⅓ filled with de-ionized water, placed in a desiccator between 20% and 50% RH at RT, and dried overnight. The silk/PEO mats were draped such that the mat contacted, and lightly adhered to, the rim along the entire circumference of the mouth. During the drying phase, as the saturated samples uniformly dried from the rim towards the center of the sample, each set of mats progressively shrank across the mouth of the dish. The 4:1 and 3:1 samples completely dried attached to the rim of the crystallization dish resulting in a stretched, completely flat, pliable, white membrane-like material. Sample weight (Mettler Toledo AB54-S/FAC, Columbus, OH) and thickness (Ono Sokki EG-225F Digital Indicator, Addison, Ill.; AA821 radius point; 25 g force) measurements were recorded for each silk system.

Example 2

Material Characterization

Fiber thickness and surface topography were characterized using a JEOL JSM 740-1F FE-SEM (Tokyo, Japan) at 1.5×, 6.5× and 12× magnifications (acceleration voltage: 1 kV, working distance: 13.6 mm). Cross-sectional images were taken using 2.5×, 5×, 10×, and 50× magnifications (acceleration voltage: 5 kV, working distance: 6 mm). Cross-sectional samples were cut into 2×5 mm pieces and flash frozen in liquid nitrogen and broken in half using tweezers. Samples were mounted on carbon tape with the cross-sectional surface facing up. All samples were coated with 100 Å Au using the Denten Vacuum Desk IV (Moorestown, N.J.) with the following settings: vacuum: 80-90 mtorr, sputtering set point: 20-30%, deposition time: 2 min. Surface morphology, roughness, and 3D features of the samples were obtained via the PSIA XE-150 AFM (Santa Clara, Calif.), using the Ultrasharp NSC16/AIBS probe in non-contact mode (resonant frequency: 170 kHz, force constant: 45 N/m). XEI data analysis software (Park Solutions, Santa Clara, Calif.) was employed for characterization of surface roughness. Material porosity, defined by a pore extending a minimum depth of five fiber layers (~1 μm), was statistically evaluated applying a distribution bucket algorithm over a 50×50 μm area. Pore throat size and pore surface area were geometrically estimated over circular regions with pore size diameters ranging from 0.15, 0.30, 0.45, 0.60, 0.75, 0.90, 1.05 and 1.25 μm.

Example 3

Water and Oxygen Permeability

Absorption. Six 2.8 cm diameter test samples were dried with the polystyrene-dish method, placed in sterile 6-well tissue culture treated polystyrene plates and immersed in de-ionized water for 24 hrs to reach swelling equilibrium. The samples were then removed and gently dabbed onto Kimwipe® tissues until a minimal stable pendant drop was maintained at the end of the sample. The saturated samples were then weighed and water absorption and equilibrium water content (EWC) were calculated by the following equations:

$$\text{Absorption \%} = \frac{(W^w - W^d)}{W^d} * 100\%$$

$$EWC\ \% = \frac{(W^w - W^d)}{W^w} * 100\%$$

where $W^w$ and $W^d$ are the weights of the wet and dry sample, respectively. Kim et al., 341 Int. J. Pharm. 35-43 (2007). The results of Absorption (%) and EWC (%) are shown in Table 4.

Oxygen Transmission Rate. The Oxygen transmission rate (OTR) was measured using the Illinois 8001 Oxygen Permeation Analyzer (Illinois Instruments, Johnsburg, Ill.; ASTM 3985-05). Circular 5 $cm^2$ de-ionized water saturated samples were tested over 15 minute test intervals in a hydrated environment at 37° C. and 80% RH and under drier conditions at 37° C. and 50% RH. A successful test was concluded upon the recording three consecutive oxygen transmission rates within 1%. Oxygen transmissibility was recorded by $cm^3/m^2$ per day according to ASTM 3985-05. Samples were sealed between the 5 $cm^2$ masks using Apiezon Type T Grease (Manchester, UK). The results for oxygen gas transmission rate and oxygen transmission rate per unit thickness are shown in Table 5.

Water Vapor Transmission Rate. WVTR was measured using the Perm Cup (Gardner Co., Pompano Beach, Fla.) according to the ASTM D1653 water cup method B. Saturated and dried 25 $cm^2$ diameter samples were sealed to the open mouth of a cup filled to 6 mm of the top edge and placed in a temperature and humidity controlled environment maintained at 73±1° F. (22.8±0.6° C.) and 50±2% RH for 24 hrs. The loaded cup setup was weighed at the start and after 24 hours to 0.1 mg granularity. Temperature and relative humidity were verified every 6 hr and water vapor transmission calculated by cup weight loss in $g/m^2$ per day.

Biodegradation. The protease employed for biodegradability was shown to non-discriminatingly cleave silk fibroin at multiple locations in the protein structure. Horan et al. 26 Biomats. 3385-93 (2005); Li et al., 24 Biomats. 357-65 (2003). Three-ply circular 3.5 cm samples from the six material groups were manicured to weigh 25±5 mg and sterilized in three 20-minute baths of 70% ethanol, rinsed with PBS and then incubated at 37° C. in a 6 mL solution of 1 mg/mL protease XIV (EC 3.4.24.31, 5.6 U $mg^{-1}$' Streptomyces griseus, Sigma, St. Louis, Mo.) in PBS at pH 7.4. Jin et al., 15 Adv. Funct. Mater. 1241-47 (2005); Horan et al., 2005. Control samples were immersed in PBS without enzyme. Enzymatic and control solutions were replenished daily. Biodegradability was measured at 1, 3, 6, 10, and 14 days after rinsing samples in deionized water for 1 hr. Samples were transferred from culture well plates to designated pre-weighed weight boats using a small spatula and a 25-g. capillary tube attached to a 4 mL syringe. Samples were dried at RT for 24 hr under a sterile hood and then weighed to determine percent weight loss over time. Linear regression analysis was done using Minitab® 15.1.30 (Minitab Inc., State College, Pa.).

Example 4

Materials. Cocoons of *Bombyx mori* silk (Tajima Shoji Co., Yokohama, Japan) were prepared to generate an 8 wt % silk solution. Wang et al., 2006. Six silk materials were prepared with 4:1, 3:1, 2:1, 3:2, 7:6, and 1:1 w/w silk:PEO (900,000 g/mol) ratio solutions. The 4:1, 3:1, and 2:1 blends contained 5% PEO, while the 3:2, 7:6, and 1:1 blends contained 6% PEO in order to maintain the minimum 7.2% silk/PEO polymer concentration necessary for viscoelastic and surface tension properties to generate stable fluid jets during electrospinning.

Solution viscosities were determined with a Brookfield HATD viscometer (Brookfield Engineering Laboratories, Inc., Stoughton, Mass.) using a #5 spindle at 69° F. equaling 128, 152, 240, 424, 768, and 1120 mPa·$S^{-1}$, respectively.

The electrospinning apparatus built for this research followed previously published procedures, employing a high voltage power supply (Gamma High Voltage Research ES-30P, Ormond Beach, Fl.), a 60 mL syringe pump (Braintree Scientific 8000, Braintree, Mass.), potential and ground stages, 1.5 mm polyethylene tubing and a 16 gauge 5.08 cm steel capillary tube.

The silk/PEO solution was pumped through polyethylene tubing from the syringe pump to the 12 kV DC charged steel capillary tube inserted in the potential plate. Electrospun fibers were collected on an aluminum foil covered ground stage, placed approximately 21 cm below the potential plate and located approximately 2.5 cm beyond the vertical fall line of the capillary tip.

Ten and 4.5 mL batch solutions for silk/PEO at each blend ratio listed above were used to create 16.5 and 10 cm silk mats, respectively. Solutions were electrospun at room temperature (RT, 20-22° C.) and at a relative humidity (RH) below 60%. Silk/PEO mats were immersed in a 90% MeOH solution for 20 min to induce β-sheet formation and crystallization. PEO was extracted with leaching in three 1 L dH$_2$O baths over 72 h.

Based on the weight ratio equation $$\text{Silk \%} = \frac{\text{Silk \%}}{\text{Silk \% + PEO \%}} \quad \text{(Equation 1)}$$

the silk content for each model was 86.5 wt %, 82.8 wt %, 76.2 wt %, 66.7 wt %, 60.9 wt %, and 57.1 wt %, respectively. Untreated, water soluble silk/PEO mats were designated as S87P13, S83P17, S76P24, S67P33, S61P39, and S57P43 (S87P13-SP57P43). Mats denoted as S87, S83, S76, S67, S61, and S57 (S87-S13) represent methanol-treated, PEO-extracted silk mats.

Drying Methods. Unconstrained and constrained drying techniques were employed to evaluate the physical properties of the S87-S57 silk material groups.

In the unconstrained-drying method, saturated 3.5 cm diameter samples were punched from 10 cm electrospun casts, hand pressed between weighing paper (VWR, West Chester, Pa.) and then vertically placed on the sidewall of a polystyrene Petri dish for maximized surface-to-air interface until nearly dry. Samples were periodically repositioned to prevent sticking and dried for 24 h at RT.

Applying the constrained drying technique, silk material was dried while undergoing a drawing force while draped over and attached to the mouth of a crystallization dish. Taken from a water bath, 16.5 cm diameter S87-S57 samples were draped over a 125×65 mm$^2$ crystallization dish that was one-third filled with dH$_2$O and dried under ambient conditions overnight. Sample weight (Mettler Toledo AB54-S/FAC, Columbus, Ohio) and thickness (Ono Sokki EG225F Digital Indicator, Addison, Ill.; AA821 radius point; 25 g force) measurements were recorded for each silk system.

Material Characterization. Fiber morphology, surface topography, and cross-sectional properties were characterized by a field emission scanning electron miscroscope (FE-SEM, JEOL JSM 740-1F, Tokyo, Japan) over 1.5-50× magnification. Fiber morphology was evaluated for S87P13-S57P43 and constrain-dried S87-S76 sample sets. Surface topography and cross-sectional properties were assessed for constrain-dried S87-S76 samples. Cross-sectional samples were cut into 2×5 mm$^2$ pieces and flash frozen in liquid nitrogen and broken in half using tweezers. Samples were mounted on carbon tape with the cross-sectional surface facing up. All samples were coated with 100 Å Au using the Denton Vacuum Desk IV (Moorestown, N.J.) at the following settings: vacuum 80-90 mtorr, sputtering set point 20-30%, deposition time 2 min.

Surface morphology of S87-S57 samples were measured via the PSIA XE-150 atomic force microscope (AFM, Santa Clara, Calif.), using the Ultrasharp NSC16/AIBS probe in non-contact mode (resonant frequency: 170 kHz, force constant: 45 N·m$^{-1}$). Image roughness and three-dimensional (3D) features were rendered by XEI quantitative analysis (Park Solutions Inc., Santa Clara, Calif.). Material porosity was defined by a pore extending a minimum depth of 5 fiber layers (~1 μm). A pore throat size frequency distribution was measured over a 50×50 μm$^2$ area.

Absorption. Unconstrained dried, 2.9 cm diameter S87-S57 samples were pre-weighed and then immersed in dH$_2$O for 24 h to reach swelling equilibrium. The samples were then gently dabbed onto Kimwipe® tissues until minimal water was observed on the sample surface. The saturated samples were then weighed and water absorption and equilibrium water content (EWC) were calculated by the following equations:

$$\text{Absorption \%} = \frac{(W^w - W^d)}{W^d} * 100\%$$

$$EWC \% = \frac{(W^w - W^d)}{W^w} * 100\%$$

where $W^w$ and $W^d$ are the weights of the wet and dry sample, respectively.

Oxygen Transmission Rate. The oxygen transmission rate (OTR) was measured using the Illinois 8001 oxygen permeation analyzer (Illinois Instruments, Johnsburg, Ill.; ASTM 3985-05). OTRs were measured for circular 5 cm$^2$ hydrated S87-S57 samples tested over 15 min intervals at 37° C. and 80% RH. OTRs for unconstrained dried S87-S57 mats were measured at 37° C. and 50% RH. Oxygen transmissibility was recorded in cm$^3$·m$^{-2}$·d$^{-1}$ according to ASTM 3985-05 and a successful test was concluded upon recording of three consecutive OTRs within 1%. Samples were sealed between 5 cm$^2$ masks using Apiezon Type T Grease (Manchester, UK).

Water Vapor Transmission Rate. Water vapor transmission rate (WVTR) was measured using the Perm Cup (Gardner Company, Pompano Beach Fla.) according to the ASTM D1653 water cup method B. Hydrated and constrain-dried circular 25 cm$^2$ S87-S76 samples were sealed over the mouth of a Perm Cup filled to 4 mm from the top with dH$_2$O. Pre-weighed assembly was placed in an environment maintained at 73±1° F. (22.8±0.6° C.) and 50±2% RH and re-weighed after 24 h to 0.1 mg granularity. Temperature and relative humidity were verified every 6 h and water vapor transmission calculated by assembly weight loss in g·m$^{-2}$·d$^{-1}$.

Biodegradation. The protease employed for biodegradability was shown to indiscriminately cleave silk fibroin at multiple locations in the protein structure. Three-ply circular 3.5 cm unconstrained dried S87-S57 samples were cut to weigh 25±5 mg, sterilized via three 20 min immersions in 70% ethanol, rinsed with phosphate-buffered saline (PBS, pH=7.4, Invitrogen 291, Carlsbad, Calif.), and then incubated at 37° C. in a 6 mL PBS solution of 1 mg·mL$^{-1}$ protease XIV (EC 3.4.24.31, 5.6 U·mg$^{-1}$, *Streptomyces griseus*, Sigma, Mo.). Control samples were immersed in PBS without enzyme. Enzymatic and control solutions were replenished daily. Biodegradability was measured at 1, 3, 6, 10, and 14 d after rinsing samples in dH$_2$O for 1 h. Samples were transferred from culture well plates to designated pre-weighed weight boats using a tapered flat end micro spatula and a 25 gauge capillary tube attached to a 4 mL syringe. Samples were dried at RT for 24 h under a sterile hood and then weighed to determine percent weight loss over time. Linear regression analysis was performed using Minitab® 15.1.30 (Minitab Inc., State College, Pa.).

Figure 1B:
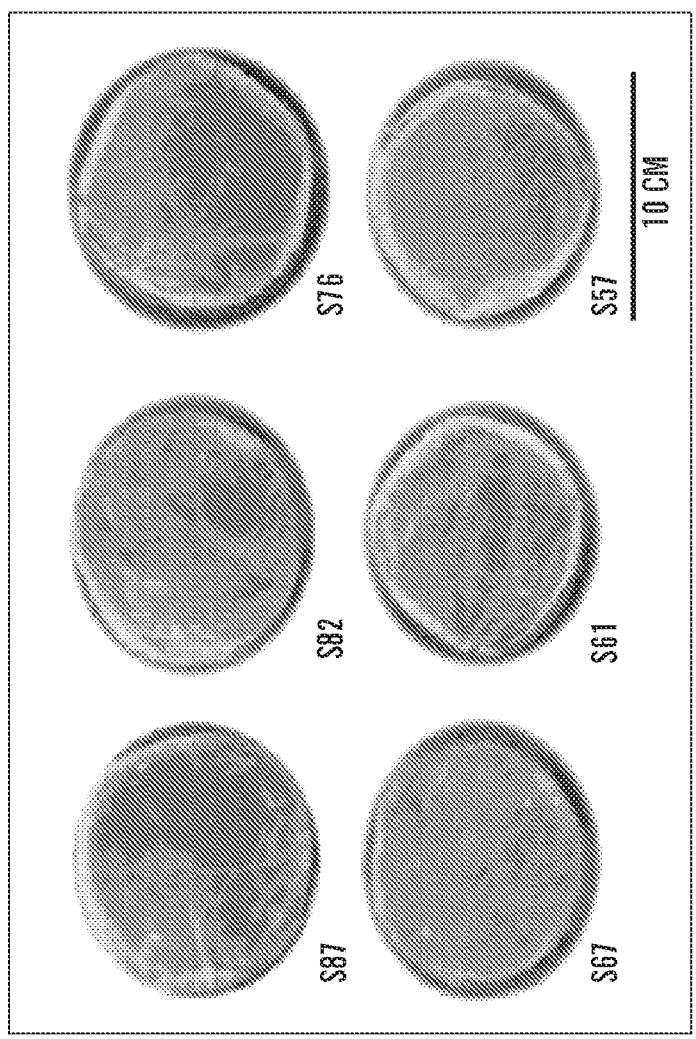
FIG. 1B shows the 10 cm diameter S87-S57 silk mats immersed in dH$_2$O. Each mat exhibited a uniform conformation with a pliable soft silky texture. White spots and creases reflect air bubbles and folds in the materials.

Initial Evaluation. Employing the silk/PEO electrospinning process, all six S87P13-S57P43 material systems were electrospun into 16.5- and 10-cm diameter mats. The physical properties of each S87-S57 sample were evaluated in hydrated and dry states. Immersed in dH$_2$O, all six S87-S57 material groups had a uniform conformation with an opaquely translucent appearance and were pliable with a silky texture, but extended handling exhibited increased material shearing respective to decreasing silk concentration (FIG. 1B). Silky texture was referenced to describe the dynamic hygroscopic nature of fibroin where water molecules absorb and plasticize throughout the amorphous bulk matrix. Either forming hydrogen bonds to amino, hydroxyl, or carboxyl acid end groups or free to disperse throughout the hydrophiic domain, highly mobile water molecules are continuously transitioning with kinetic energy minimization producing the soft silky texture of these saturated material systems.

Figure 2B:
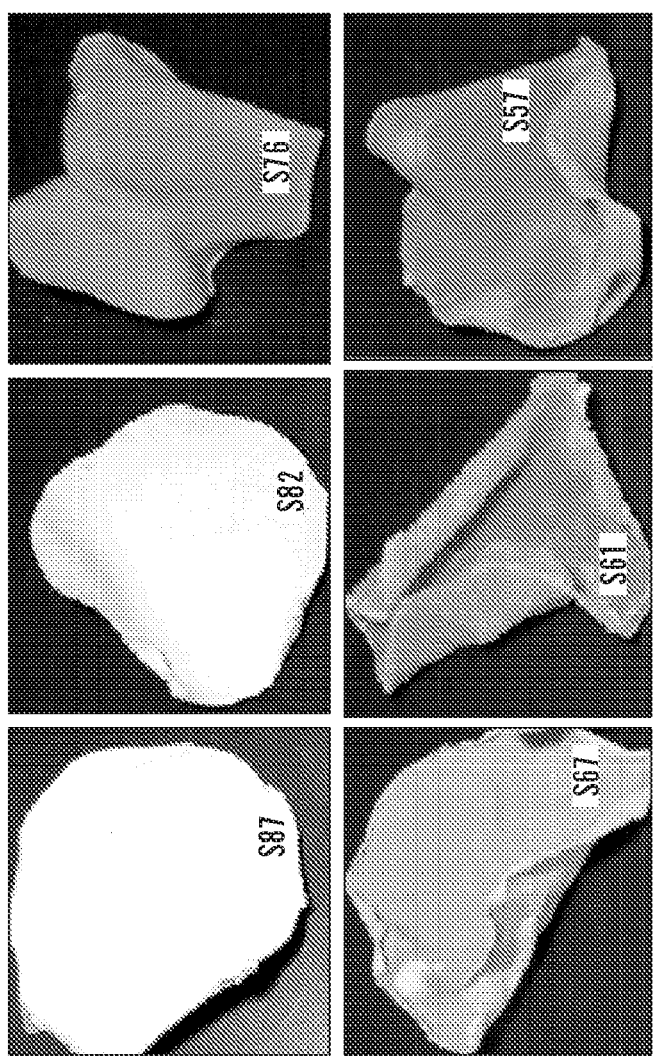

Drying Method 1. Hydrated, the 3.5-cm S87-S57 samples may fold over in half to achieve a net force surface-surface hydrophobic equilibrium and display a hydrophilic propensity with layered silk sheet separation and displacement. After the 24 h drying period, however, the physical characteristics progressively changed over S87-S57 material systems. Relative to decreasing silk concentration, the mats were transformed from snow white, pliable, wafer-like structures to a translucent-brown, ultra-thin, film-like materials with limited cohesive flex strength (FIG. 2B).

Characteristic of the twisted pleated β-sheet formations of protein polymers, the matrices were not dried in a completely flat orientation with only the S87 and S82 groups retaining the original circular shape. Additionally, there is a proline positioned at the terminus of the amorphous domain interlaced between the heavy chain crystalline regions. Proline has been shown to contract with dehydration, increasing the fiber's capacity to shrink. These factors contribute to the twisted, irregular conformations of the unconstrained dried samples losing between 51.0±0.0% and 87.5±9.9% of their surface area (FIG. 13).

Figure 13A:
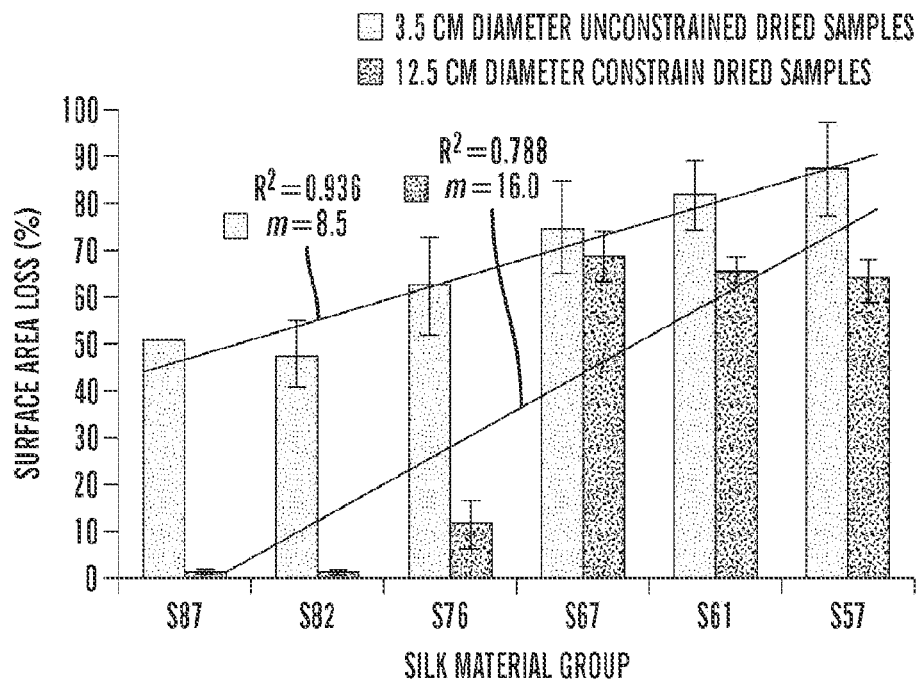
FIG. 13A is a graph depicting the percentage of the silk surface area transformation for the unconstrained and constrain-dried S87-S57 silk mats. Surface area loss between drying techniques was significantly different for the S87 and S82 silk mats (P=0.001) (bars=standard deviation, n=3).
Figure 13B:
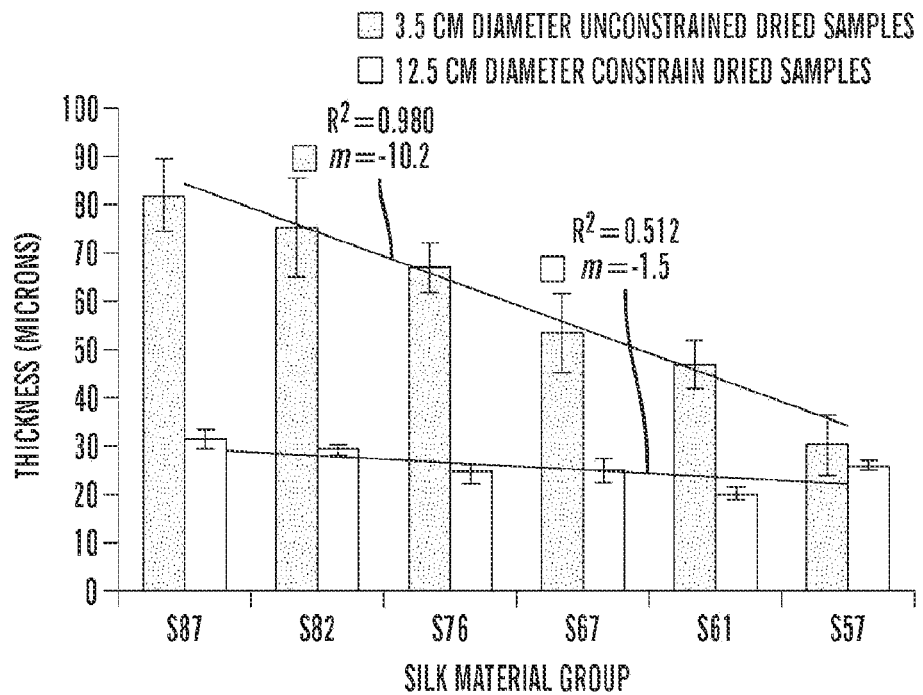
FIG. 13B is a graph depicting the material thickness relationship between the unconstrained and constrained drying techniques for S87-S57 samples. S87-S61 unconstrained-dried silk mats were significantly thicker than the constraindried groups (P=0.001) (SD±%, n=6).

Thickness measurements for the unconstrained dried S87-S57 material groups linearly declined from 81.7±7.5 μm to 77.5±10.5 μm, 66.7±5.1 μm, 53.3±8.1 μm, 46.7±5.1 μm, and 30.0±6.4 μm, respectively (FIG. 13). PEO concentration may have a direct influence on fiber surface area and bulk morphology during the electrospinning process. Wang et al., 2006. As the PEO concentration increases, the size of the fibroin micelle and globule structures that form the silk fiber decrease. Additionally, longitudinal stresses within the whipping electrified fluid jet cause these globule structures to align and elongate up to 10000 times. Wang et al., 2006; Kowalewski et al., 2005; Reneker & Yarin, 2008. Consequently, silk fibers formed with increased PEO concentration had a reduced bulk volume which correlates to the progressive physical transformation observed over the unconstrained dried S87-S57 material groups.

Drying Method 2. Hydrated, the 12.5-cm S87-S57 samples were easier to unfold. Layered sheet separation was only observed in the interior region of each mat without lateral displacement. Perhaps this may be attributed to the fact that these samples were not punched from larger samples, thus retaining the crystallized regions at the parameter of the samples. Referencing the constrain-dried mats in FIG. 3B, the S87 and S82 samples dried attached to the crystallization dish, retaining 98% of the original surface area, resulting in flat, pliable, white membranes. The S67, S61, and S57 groups did not fare as well. As these samples dried, drawing forces stressed the material beyond the fiber elongation yield point resulting in structural failure and a 60% surface area loss. Material shearing typically was initiated at the dish rim and propagated into the interior region of the silk mat. Although the S76 sample sheared from the dish rim, there was only a 12% surface area loss and the physical properties were similar to the S87 and S82 matrices (FIG. 13).

During the constrained drying period, water molecules evaporating at the surface substrate and throughout the protein bulk region initiated methyl group convergence and hydrophobic chain interaction. This cascade actualized the loss of free volume and fibroin contraction. Attached to the rim of the crystallization dish, the material became constrained, causing the fibers to draw and elongate in the direction of the radial stress. Given that the material is homogeneous across each sample group and the average thickness for the 12.5 cm constrain-dried S76 and S67 samples were negligible (FIG. 13), it appeared that the shearing point of each material group was dependent on bulk volume of each fiber.

Figure 6B:
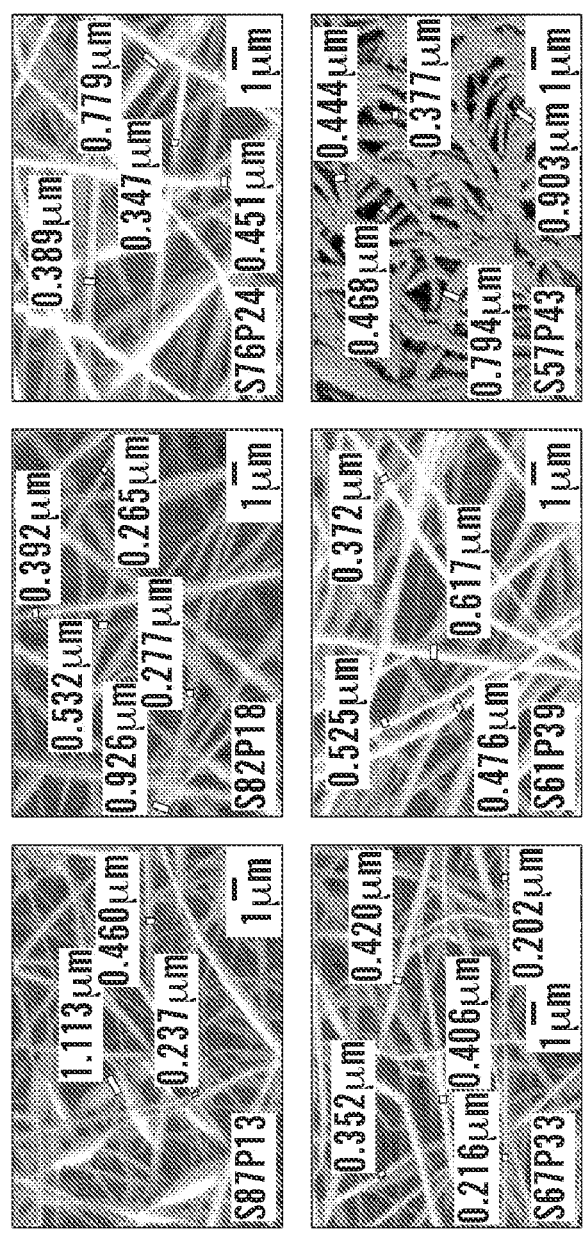

Material Characterization. FE-SEM micrographs of untreated S87P13-S57P43 mats are shown in FIG. 6B. Overall, these electrospun silk/PEO fibers range from 200 nm to 500 nm in diameter with a uniform distribution throughout the structure, and fiber bead formation was increasingly pronounced with decreasing PEO concentration. Wang et al., 2006; Zhou et al., 2000; Huang et al., 2001. S87P13, S82P18, and S76P24 fibers had randomly dispersed beaded segments ranging from just over a μm down to 700 nm in diameter. Beading was minimized in S67P33 and S61P39 images, disclosing a uniform distribution of well-defined 200 nm-500 nm diameter fibers. The S57P43 sample had a unique morphology manifested from irregular and non-circular shaped fibers transitioning into a non-uniform, dense mat structure. Dense mat appearance may be attributed to un-solidified fiber phase dispersion when congregating on the apparatus ground stage. S57P43 fibers ranged from 300 to 500 nm in diameter whereas the melded fibers measured between 700 nm and 900 nm.

The FE-SEM images in FIG. 14 show the constrain-dried S87-S76 material groups. Although the surface topographies in FIG. 14A reflect a dense, random distribution of fibers throughout each model, closer evaluation reveals increasing evidence of fiber elongation and realignment, which occurs with the contrain-drying technique. S87 fibers in FIG. 14B have a relaxed twisted appearance with limited fiber elongation or alignment. In contrast, S82 and S76 fibers became elongated and aligned forming web-like micro textures. The S82 mat in FIG. 14C exhibits taut webbed structure with evidence of phase dispersion between adjacent fibers culminating in co-continuous transparent morphology. The webbed structure for the S76 samples is defined by an intertwining network of well-defined, elongated, aligned fibers forming rope-like arrangements.

Figure 8A:
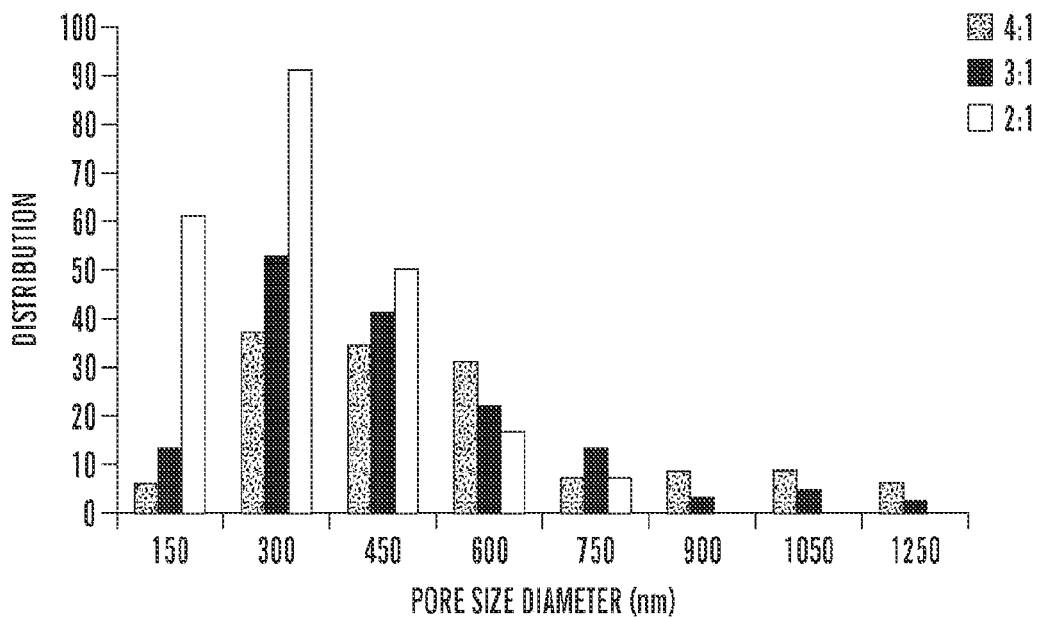
FIGS. 8A and 8B are histograms of pore throat size distributions for the 4:1, 3:1, and 2:1 constraint-dried mats (8A) or S87-76 mats (8B) over a 50×50 μm region. Respective to decreasing silk concentration, the number of pores escalated from 139 to 226 with an increased accumulation of pores with reduced throat size diameters.
Figure 8B:
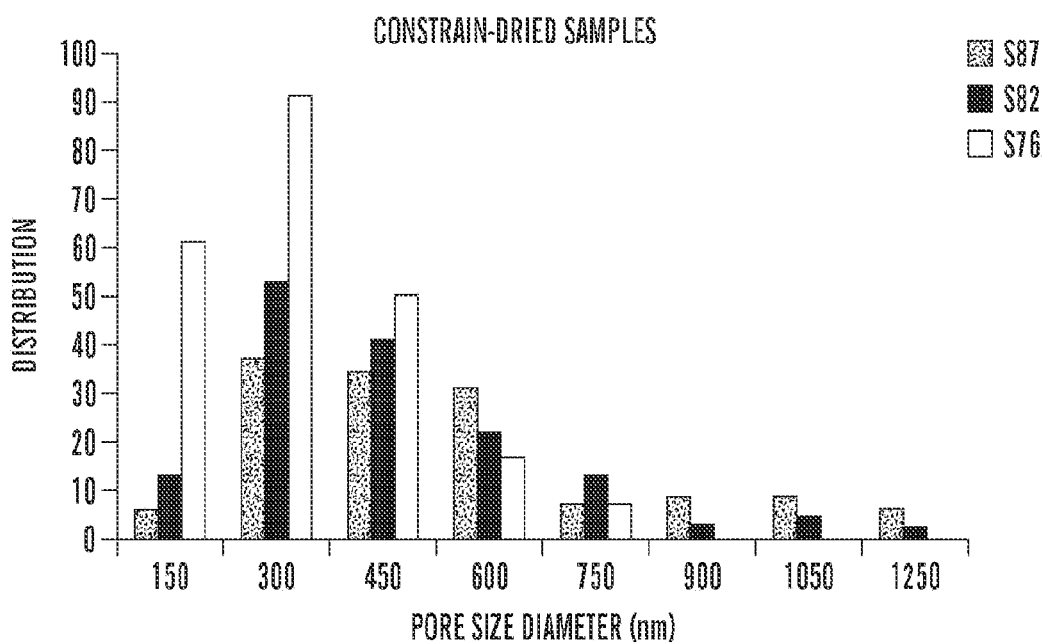

The fiber alignment and elongation manifested through the contrain-drying technique can be attributed to the amphiphilic properties exhibited with the silk fibroin block copolymer design. Acting as a plasticizer within hydrophilic regions, water molecules propagate nter-molecular movement between low cohesive energy amorphous chains promoting secondary structure mobility and realignment. As stated, evaporation actuates hydrophobic chain interaction and free volume loss which causes the fiber to contract and draw in the direction of the radial stress. As secondary structures begin to elongate, proline folding at the terminus of the amorphous light chain becomes inhibited which promotes the alignment of bilateral inter-chain laminar structures and restricts crystallized intra-chain twisted conformations. Predominant inter-chain hydrophobic interactions also influence crystalline secondary structure transition from amorphous silk I to crystalline silk II. The combination of these effects produce mats with mechanical stability and flex strength along the fiber axis (FIG. 8B). Beyond the elongation yield point, shearing deformation takes place within and along the amorphous secondary structures of both heavy and light chains.

Figure 14A:
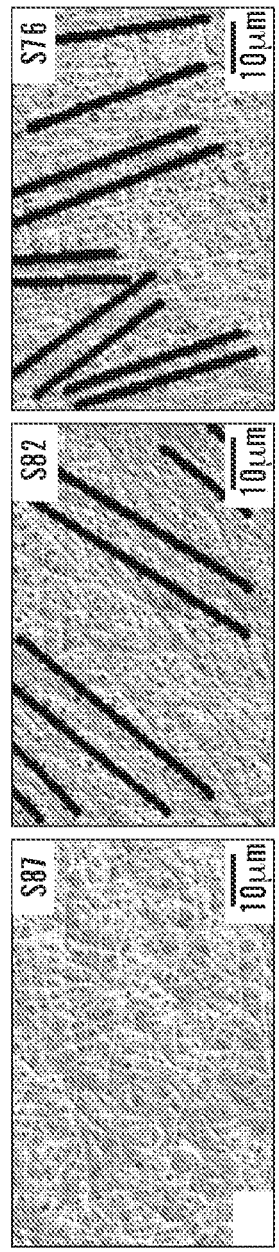
FIGS. 14A-E are FE-SEM micrographs of constrain-dried S87, S82, and S76 silk mats, respectively.
Figure 14B:
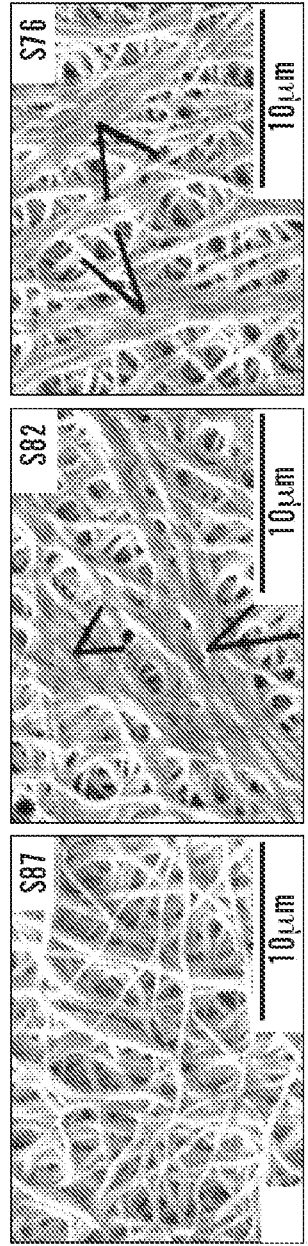
Figure 14D:
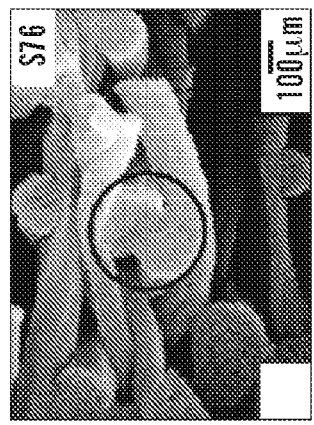
Figure 14C:
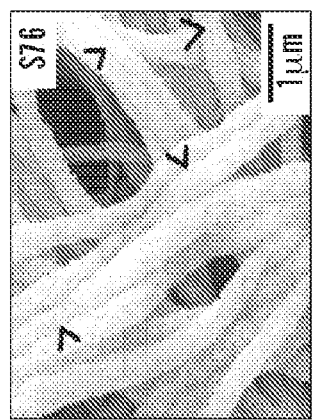
Figure 14C:
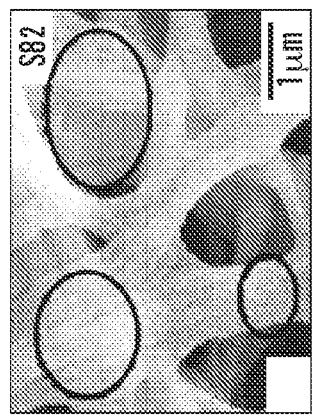

The appearance of macroscopic phase dispersion between aligned S82 fibers in FIG. 14C and the S76 fibers in FIG. 14D can also be attributed to plasticizing properties of water. Differential scanning calorimetry of hydrated B. mori silk films revealed that the glass transition temperature (Tg) of dehydrated silk fibroin decreased from 178° C. to below 40° C. with 20-23 wt % water absorption. Although crystalline conformation influences absorption throughout the bulk region, the EWC for each hydrated group was greater than 80 wt % (Table 7), indicating considerable hydrophilic interaction, forecasting Tg reduction and plausible phase dispersion. Additionally, a mobile material surface substrate is exhibited when interfacial energy is minimized as hydrophilic and hydrophobic molecules reverse during surface/liquid, surface/gas, surface/surface thermodynamic transitions. Factoring in both phase dispersion and hydrophiic/hydrophobic surface interchange over the drawn drying period, amorphous secondary structures become interspersed between interfaced fibers creating melded fiber conformations. It is also conceivable that the linear secondary structures between fibers may become aligned forming thermodynamically stable crystalline β-stands.

TABLE 7

Average absorption and EWC measurements for 2.9 cm diameter unconstrained-dried S87-S57 samples immersed in $dH_2O$ for 24 h (±SD, n = 6).

| Silk material group | Dry Weight mg | Saturated Weight mg | EWC % | Absorption % |
|---|---|---|---|---|
| S87 | 22.1 ± 6.5 | 121.8 ± 25.3 | 82 ± 3 | 461 ± 82 |
| S82 | 21.5 ± 3.0 | 148.0 ± 18.8 | 85 ± 1 | 593 ± 85 |
| S76 | 14.2 ± 1.7 | 90.7 ± 16.1 | 84 ± 2 | 538 ± 84 |
| S67 | 14.4 ± 0.8 | 90.2 ± 5.6 | 84 ± 1 | 530 ± 84 |
| S61 | 14.1 ± 0.7 | 94.3 ± 13.8 | 85 ± 2 | 569 ± 85 |
| S57 | 13.6 ± 3.8 | 93.9 ± 12.7 | 86 ± 2 | 613 ± 86 |

Figure 14E:
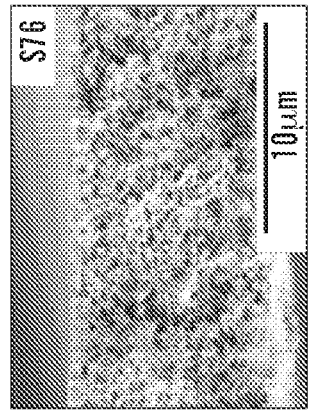
Figure 14E:
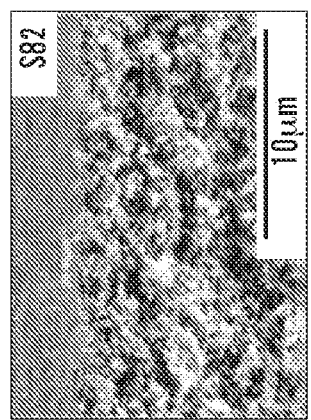
Figure 14E:
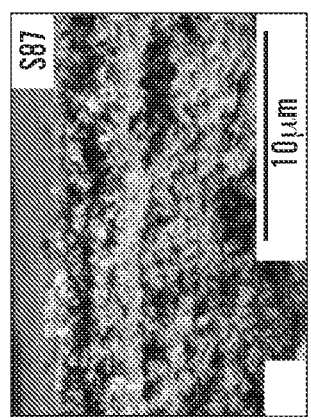

Cross-sectional views of constrain-dried S87-S76 material groups in FIG. 14E disclose increased fiber density and aggregation with respect to decreasing silk concentration. The S87 fibers aggregated in horizontal sheets with numerous large interspatial gaps. The S82 and S76 mats demonstrated increased fiber bundling and progressive reduction of interspatial gaps. These observations correspond to the decreasing mat thickness respective to silk volume. The S87-S76 micrographs in FIG. 14B exhibit an interconnecting porosity throughout these conformations. Pore throat size surface area averaged 294 $nm^2$, 201 $nm^2$, and 103 $nm^2$, respectively. The descending pore size distribution corresponds to the increased fiber density exhibited in cross-sectional views and also relates to fiber assembly with respect to beading and fiber diameter over each S87, S82, and S76 material group (FIG. 9).

Figure 15A:
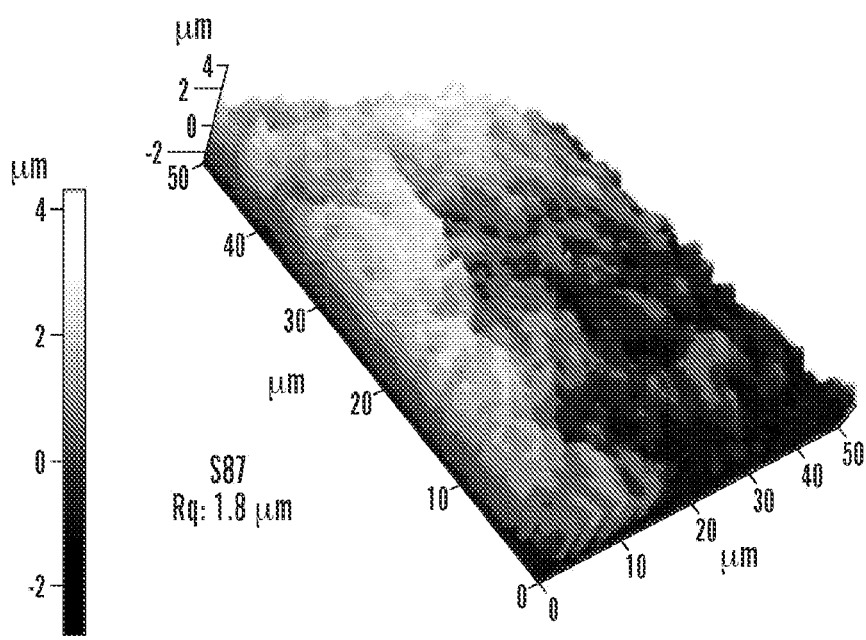
FIG. 15A is a three-dimensional AFM image of the S87 silk mat representing the well-defined surface irregularities of all S87-S57 unconstrained-dried silk mats.
Figure 15B:
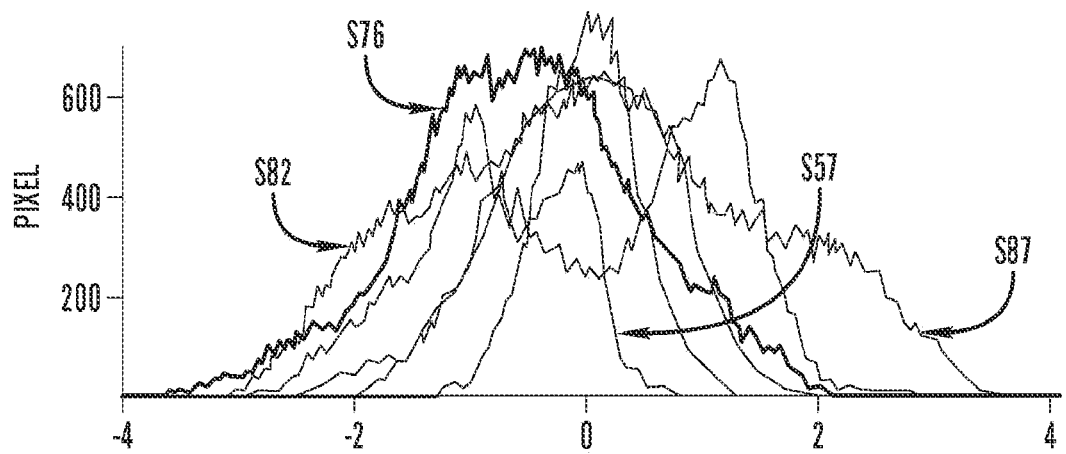
FIG. 15B is a graph showing the histogram disclosing similar z-plane peak to valley height distribution signatures for the unconstrained dried S87-S57 silk mats.

Material surface roughness influences cellular contact guidance via stress/shear free planes which facilitate the net force biomechanical equilibrium that controls cell orientation, attachment, growth, and migration. Representative of the S87 3d AFM image in FIG. 15, all six S87-S57 unconstrained dried samples demonstrated class three surface topographies exhibiting well-defined surface irregularities with root-square-mean roughness values ranging from 500 nm up to 1.4 μm. (n=3). The S87, S82, S76, S67, and S57 groups had a relatively uniform roughness with nano-sized irregularities measuring 1.17±0.00 μm, 0.65±0.10 μm, 0.88±0.17 μm, 0.76±0.16 μm, and 0.78±0.01 μm, respectively. The S61 mats had the greatest variation in regional roughness averaging 1.01±0.43 μm. AFM roughness values for constrain-dried S87, S82, and S76 samples over a 16×16 $μm^2$ area amounted to 0.66 μm, 0.36 μm, and 0.25 μm, respectively. Although having a reduced area size and limited sample size (n=1), the roughness values for the constrain-dried materials are at least 44% flatter than the unconstrained dried samples. The constrain-dried samples decrease linearly in roughness with respect to silk concentration whereas there is no evident trend for the unconstrained dried samples. This observation coincides with the fiber elongation properties of constrained drying compared to the twisted irregularities of unconstrained dried samples.

Absorption. The absorption and EWC properties of a wound dressing contribute in controlling the accumulation of wound exudates which create a feeding bed for bacteria. Referencing Table 7, absorption ranged from 461% to 613%, with all silk material groups averaging 551±54%. Although the average dry weight for the unconstrained dried S87-S57 samples linearly decreased from 22.5 mg down to 13.6 mg, the EWC remained relatively constant at 84±1%. The data suggest that water absorption is independent of fiber diameter, density, and secondary structure assembly properties of each silk concentration. It appears that the equivalent absorption and EWC rates are primarily due to the network of interconnecting pores throughout these matrices and the porosity of electrospun silk fibers. Wang et al., 2004. As water molecules plasticize into the interstitial regions of these non-woven structures and into the bulk region of the biopolymer a proportional amount of swelling occurs across all material groups.

Oxygen Transmission Rate. It is believed that a dressing which promotes oxygen/carbon dioxide gas exchange will reduce wound acidity, inhibit anaerobic bacterial infection and thus produce an environment which promotes wound healing. S87-S57 samples evaluated under hydrated conditions (80% RH) exhibited average OTRs from 25000 $cm^{-3} \cdot m^{-2} \cdot d^{-1}$ down to 7800 $cm^{-3} \cdot m^{-2} \cdot d^{-1}$, respectively (Table 8). Respective to decreasing silk concentration, the linear reduction in OTRs was attributed to the decreasing mat thickness, fiber size, pore throat size, and increased fiber density of each silk material group. OTR linear regression analysis over S87, S82, and S76 material groups had a predicted squared correlation coefficient variance of 96% and a descending OTR rate of 4800 cm $cm^{-3} \cdot m^{-2} \cdot d^{-1}$. In contrast, hydrated S87-S57 samples tested under dry conditions (50% RH) exceeded the 100000 $cm^{-3} \cdot m^{-2} \cdot d^{-1}$ analyzer threshold prior to the completion of one interval of testing. These results reflect that in a dry or near dry state these porous materials have a greater oxygen permeation rate than when oxygen is diffused through water molecules residing in the interstitial space and bulk region of a hydrated non-woven fabric.

TABLE 8

Average $O^2$ gas transmissibility rates (GTRs), WVTRs and thicknesses for S87-S57 material groups measured by 8001 OPA (Illinois Instruments, ASTM 3985-05) and Perm Cup (Gardner Company, ASTM D1653) (±SD, n = 3).

| Silk material group | $O^2$ GTR $cm^3 \cdot m^{-2} \cdot d^{-1}$ | Thickness uncons- trated - dried μm | $O^2$ GTR per thickness $cm^3 \cdot m^{-2} \cdot d^{-1} \cdot μm^{-1}$ | WVTR[a] $g \cdot m^{-2} \cdot d^{-1}$ | WVTR[b] $g \cdot m^{-2} \cdot d^{-1}$ | Thickness unconstrated - dried $g \cdot m^{-2} \cdot d^{-1}$ | WVTR[b] per thickness $g \cdot m^{-2} \cdot d^{-1} \cdot μm^{-1}$ |
|---|---|---|---|---|---|---|---|
| S87 | 25048 ± 3651 | 82 ± 8 | $2.0 \times 10^6$ | 1495 ± 75 | 2097 ± 44 | 31 ± 2 | $6.5 \times 10^4$ |
| S82 | 21972 ± 2465 | 78 ± 11 | $1.7 \times 10^6$ | 1456 ± 86 | 1989 ± 24 | 29 ± 1 | $5.8 \times 10^4$ |

TABLE 8-continued

Average $O^2$ gas transmissibility rates (GTRs), WVTRs and thicknesses for S87-S57
material groups measured by 8001 OPA (Illinois Instruments, ASTM 3985-05) and Perm Cup
(Gardner Company, ASTM D1653) (±SD, n = 3).

| Silk material group | $O^2$ GTR cm$^3 \cdot$m$^{-2} \cdot$d$^{-1}$ | Thickness unconstrated - dried μm | $O^2$ GTR per thickness cm$^3 \cdot$m$^{-2} \cdot$d$^{-1} \cdot$μm$^{-1}$ | WVTR[a] g$\cdot$m$^{-2} \cdot$d$^{-1}$ | WVTR[b] g$\cdot$m$^{-2} \cdot$d$^{-1}$ | Thickness unconstrated - dried g$\cdot$m$^{-2} \cdot$d$^{-1}$ | WVTR[b] per thickness g$\cdot$m$^{-2} \cdot$d$^{-1} \cdot$μm$^{-1}$ |
|---|---|---|---|---|---|---|---|
| S76 | 15459 ± 2610 | 67 ± 5 | 1.0 × 10$^6$ | 1413 ± 42 | 1934 ± 98 | 24 ± 2 | 4.6 × 10$^4$ |
| S67 | 16777 ± 2555 | 53 ± 8 | 0.9 × 10$^6$ | * | * | * | * |
| S61 | 12089 ± 6136 | 47 ± 5 | 0.6 × 106 | * | * | * | * |
| S57 | 7820 ± 6898 | 30 ± 6 | 0.2 × 10$^6$ | * | * | * | * |

[a]For constrain-dried S87-S76 silk materials;
[b]For hydrated S87-S76 silk materials.

Water Vapor Transmissibility Rate. The water vapor transmissibility of a full thickness wound dressing plays a role in controlling the evaporation of body fluids and inhibiting infection at the wound site. Efforts to ascertain WVTRs for S67, S61, and S57 matrices were unsuccessful due to material deformation during drying phases. WVTRs for hydrated and constrain-dried S87, S82, and S76 material groups averaged 1977±35 g$\cdot$m$^{-2}\cdot$d$^{-1}$ and 1469±81 g$\cdot$m$^{-2}\cdot$d$^{-1}$, respectively (Table 8). Saturated samples outperformed dry samples due to increased interfacial energy minimization of the direct liquid/membrane/gas interface versus the liquid/gas/membrane/gas interface. This may be due to the hydrophilic properties of these material systems which enable the expedient presentation of water molecules to the biomaterial surface/gas interface promoting accelerated evaporation. WVTR regression analysis for hydrated and dry S87-S76 material groups predicted a linear fit with squared correlation coefficient variances of 97% and 99% and descending WVTRs of 81 g$\cdot$m$^{-2}\cdot$d$^{-1}$ and 41 g$\cdot$m$^{-2}\cdot$d$^{-1}$. These negligible WVTR differences may be attributed to material thickness, fiber size, fiber density, and porosity.

Figure 16A:
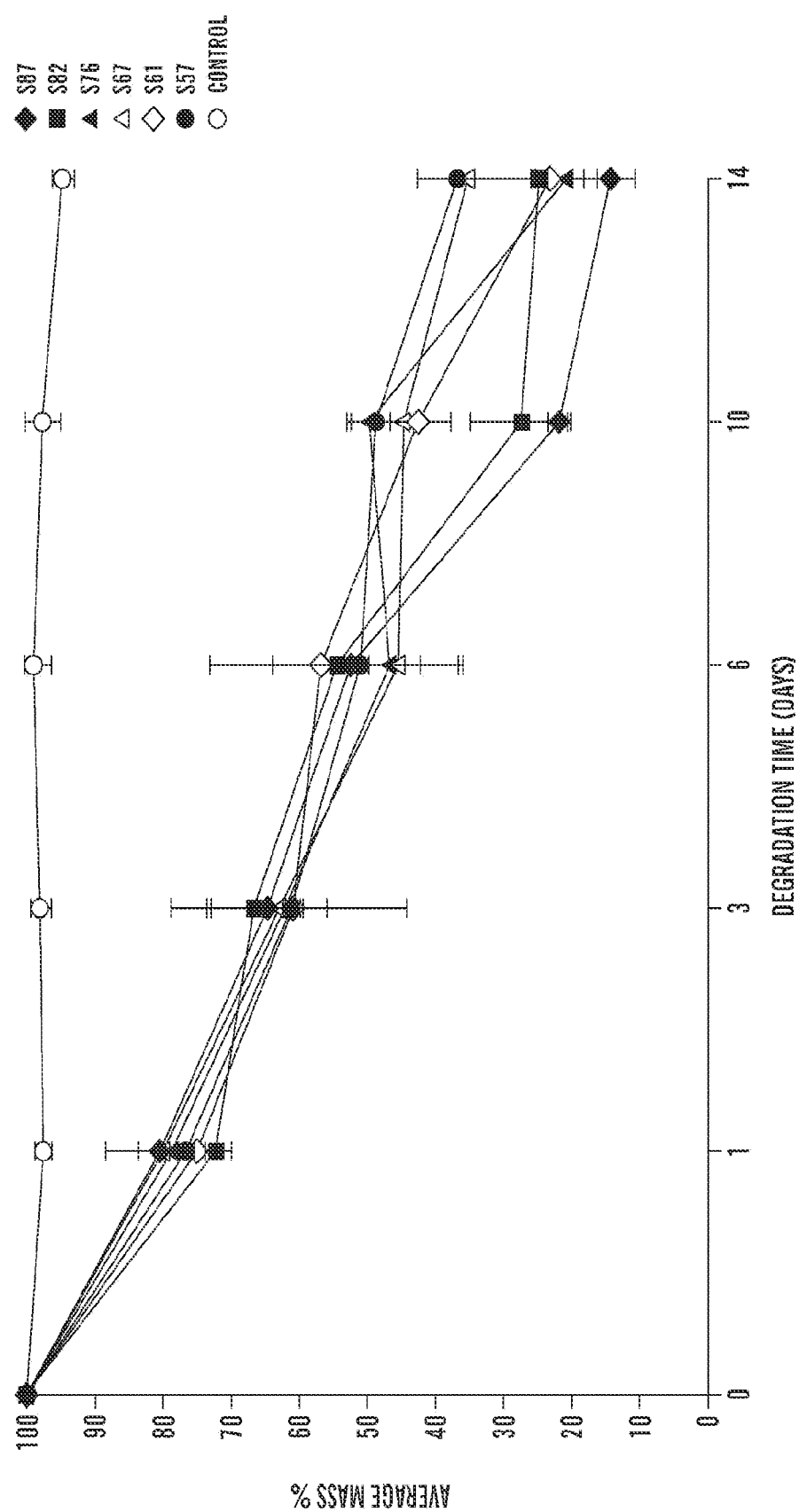
FIGS. 16A-16C are graphs representing in vitro enzymatic biodegradation analysis of S87-S57 silk mats over 1, 3, 6, 10, and 14 d time points. Three-ply 25±5 mg 3.5-cm samples were incubated at 37° C. in a 6 mL solution of 1 mg·mL$^{-1}$ protease XIV in PBS at pH=7.4. Control samples were immersed in PBS without enzyme. Enzymatic and control solutions were replenished daily.

Biodegradability. Enzymatic biodegradation of these silk materials was evaluated to facilitate epithelialization with time release biotherapies. The in vitro biodegradability study revealed a linear degradation trend for all S87-S57 material groups averaging of 22.6±3.4% degradation after 1 d and up to 74.0±8.8% material loss after 14 ds (FIG. 16A). The data suggest that up until 6 days degradation rates for all blends were relatively close at 48.2±4.6%. In contrast, after day 10 a 27% weight loss differential was recorded between the S87 (78%) and S57 (51%) samples. After 14 d, enzymatic degradation ranged from 85.6±3.8 down to 62.5±5.2% over S87-S57 samples, respectively. Upon visual inspection, all the materials systems morphologically degraded via surface erosion over the first 6 d. After 10 d, the S87 and S82 matrices demonstrated increased fiber cleavage resulting in material fraying, fragmentation, and disintegration into particulate debris. The morphological degradation of S87 and S82 samples was attributed to enzymatic access to the interior mat structure due to the increased fiber size, mat porosity, and decreased fiber density properties of these matrices.

Figure 16B:
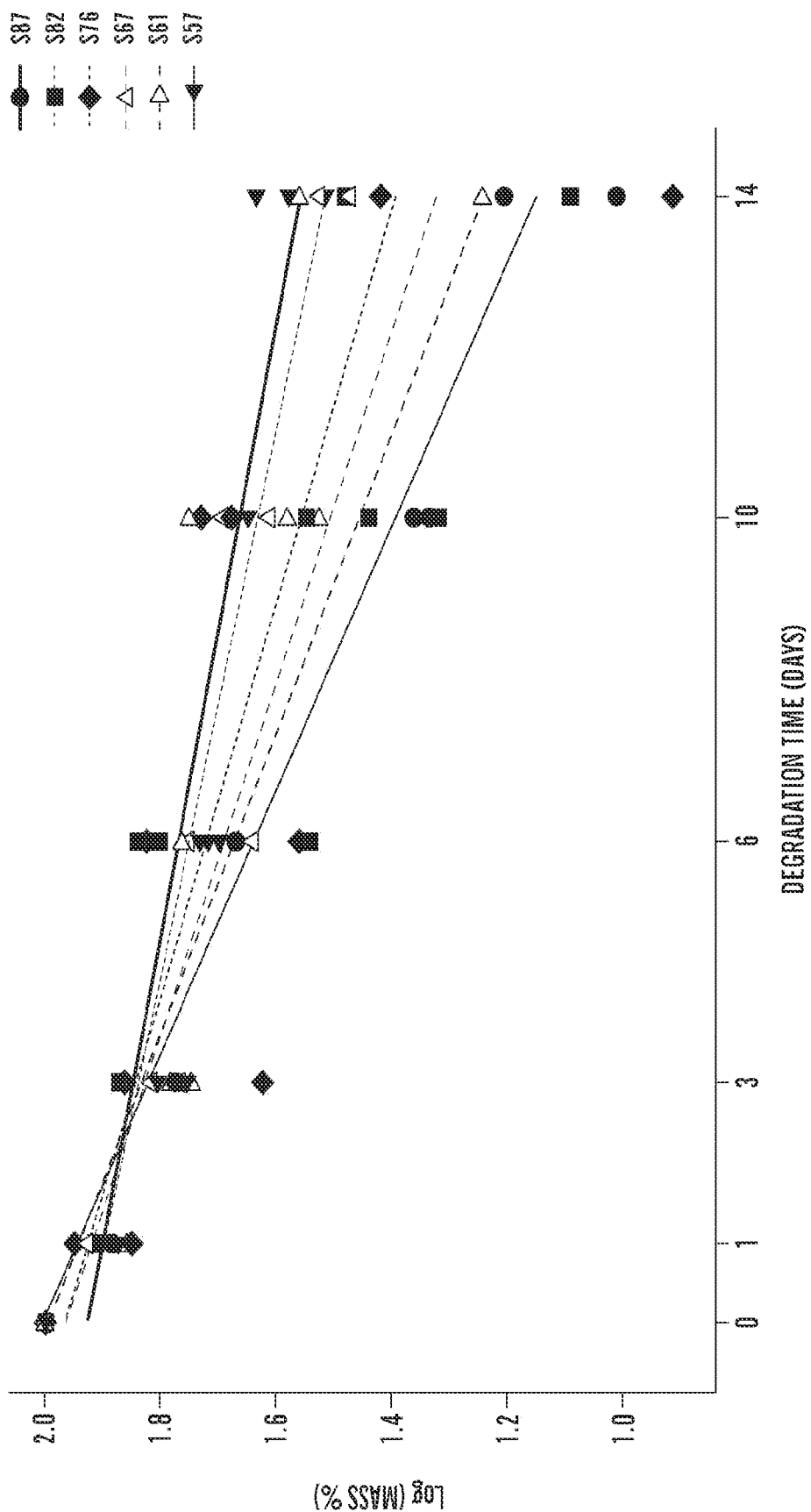
Figure 16C:
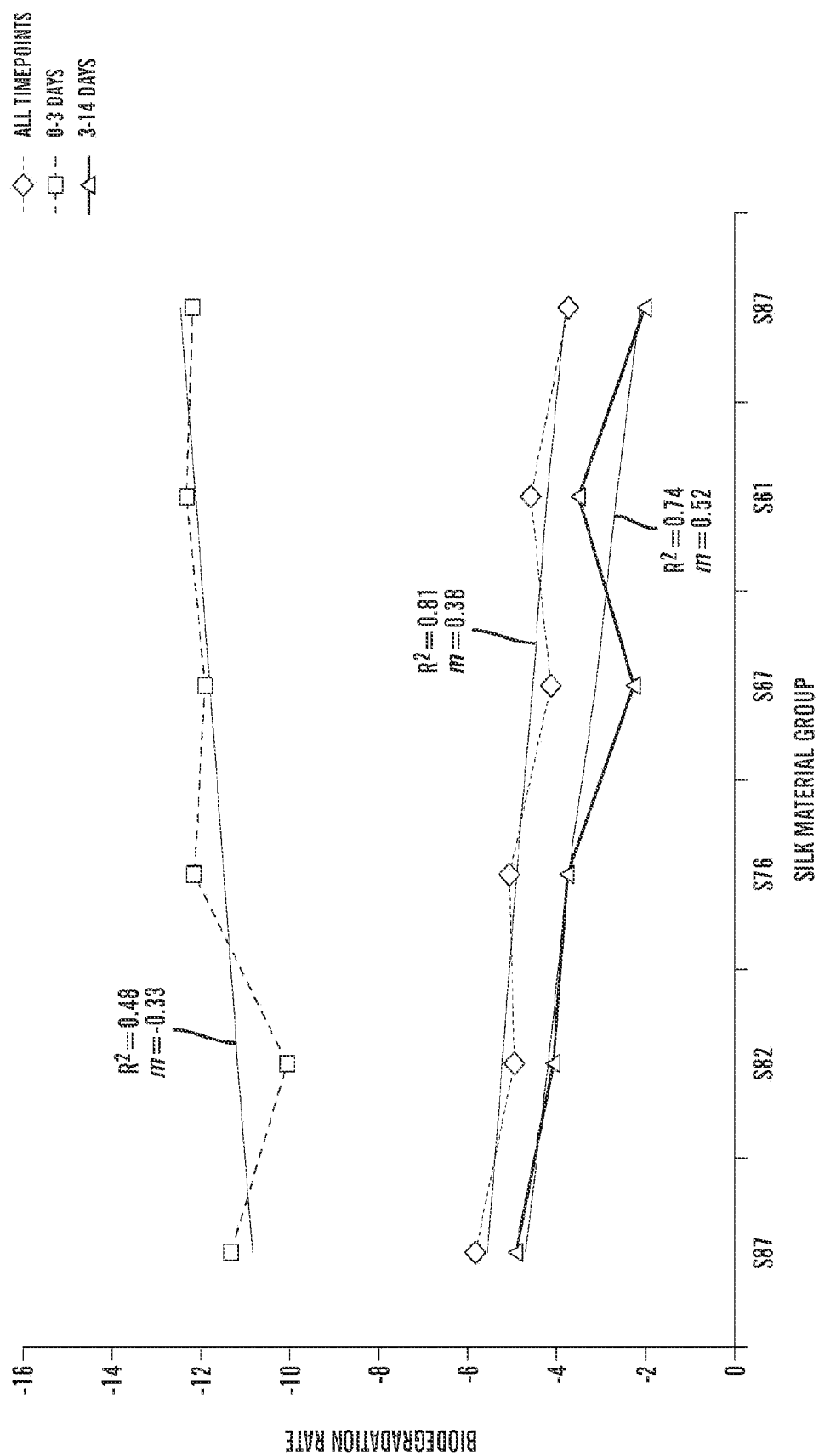

Referencing the scatter plot in FIG. 16B, a logarithmic transformation executed over each material group revealed a distinct transition point for all material groups just prior to the day three degradation time point. Regression analysis was then performed for each material group over all time points, from day 0 to day 3 and between day 3 and 14 time points. As displayed in FIG. 16C, the degradation slopes for all material groups were substantially altered after day 3. From day 0 to day 3, the enzymatic degradation rate averaged −11.7±0.9. After day 3 until day 14, the rate of degradation leveled off at −3.4±1.1. The initial accelerated degradation rate maybe attributed to the degradation of surface substrate amorphous regions compared to latent crystalline regions A material for a full thickness burn wound dressing may present many useful properties including the ability to provide an impermeable barrier to bacterial pathogens, manage wound site edema and dehydration, and support time synchronized antibiotic, immunological, and tissue regeneration biotherapies. Variant electrospun silk/PEO were design and the conformational and biofunctional properties of these PEO extracted silk material systems were studied for utility as full thickness wound dressings. Employing constrained drying techniques, it was discovered that silk concentration played a role in material structural properties including material thickness, fiber density, fiber orientation, phase dispersion, and porosity. Through this drying technique, the S87, S82, and S76 silk percent material groups were transformed into flat pliable membrane-like conformations with minimal surface area loss, which are ideal for a distributable wound dressing with a sustainable shelf life.

To maintain a stable homeostatic state, normal skin permeates body fluid at a rate of 204 g$\cdot$m$^{-2}\cdot$d$^{-1}$. A full thickness granulating wound has an evaporative water loss of 5138 g$\cdot$m$^{-2}\cdot$d$^{-1}$. It has been determined that a full thickness wound dressing having a water transmissibility rate of 2000-2500 g$\cdot$m$^{-2}\cdot$d$^{-1}$ permits adequate moisture level while preventing excessive dehydration. Referencing the absorption, EWC and water vapor transmissibility properties in Table 9, the constrain-dried S87-S76 materials performed comparatively to proposed sponge-like natural chitosan wound dressings. Although the chitosan/poloxamer dressing candidate exhibited strong absorption and EWC properties, these tests were conducted with PBS (pH=7.4) at 37° C. Additionally, the oxygen transmissibility disparities between the S87-S76 material systems and the asymmetric and bilayer chitosan materials were attributed to test conditions. OTRs for the chitosan derivatives were tested in dry conditions at 0% RH whereas dH$_2$O saturated silk materials were evaluated in a hydrated environment at 80% RH to emulate an exovasating wound environment.

TABLE 9

Average absorption, EWC, WVTR, O₂ GTR, and thickness comparison between chitosan derivative-based wound dressings and S87-S76 material systems.

| Dressing biomaterial | Absorption % | EWC % | WVTR g·m⁻²·d⁻¹ | O² GTR cm·m⁻²·d⁻¹ | Thickness μm |
|---|---|---|---|---|---|
| S87-S76 | 460-610 | 82-86 | 1900-2100 | $15.5\text{-}25.0 \times 10^3$ | 30-80 |
| bilayer chitosan | 280-950 | N/A | 1187-1230 | $4.6\text{-}18.4 \times 10^{5a)}$ | 250-800 |
| asymmetric chitosan | 130-760 | N/A | 2100-2800 | $2.8\text{-}84.2 \times 10^{5a)}$ | 60-450 |
| chitosan/poloxamer | 1700-2400[b)] | 94-96[b)] | 1900-2100 | N/A | N/A |
| B-chitin | N/A | N/A | 2400-2800 | N/A | 45-80 |

[a)]Oxygen transmission analysis performed at 35° C. and 0% RH;
[b)]Absorption and EWC measured with PBS (pH = 7.4).

Normal human skin regenerates in about 21 d. The enzymatic degradation times of these silk materials was evaluated to facilitate full-thickness wound epithelialization by employing a multi-layer wound dressing delivering time released biotherapies. Results revealed that after 14 d, the S87-S76 matrices degraded 80%, which compared favorably to the lysozyme exposed chitosan/poloxamer dressing which degraded 82% over the same time period. In contrast, the PLGA/PLLA (90/10) co-block polymer system only had a 20% degradation rate after 14 d in PBS. Because enzyme levels will vary significantly, the degradation rates in vivo should also be considered. It has been shown that silk biomaterials can degrade in weeks to years in vivo depending on material format, location, and related variables.

What is claimed is:

1. A process for producing a silk mat, comprising: electrospinning a blended polyethylene oxide (PEO) and aqueous silk fibroin solution, thereby forming a silk protein/PEO blended mat; and constraint-drying the electrospun silk mat, wherein the silk mat has a silk fibroin content ranging from about 50 wt % to about 100 wt % and wherein the silk mat has a thickness of about 20-30 microns.

2. The process of claim 1, further comprising treating the electrospun silk mat with alcohol.

3. The process of claim 1, further comprising extracting the PEO from the silk mat.

4. The process of claims 1, further comprising embedding at least one active agent in the silk mat.

5. The process of claim 4, wherein the active agent is a therapeutic agent or a biological material, selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and combinations thereof.

6. The process of claim 5, wherein the active agent is a cell selected from the group consisting of progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, precursor cells, and combinations thereof.

7. The process of claim 6, the active agent further comprises a cell growth media.

8. The process of claim 6, wherein the active agent is an antibiotic.

9. An electrospun silk mat comprising a silk fibroin protein content ranging from about 50 wt % to about 100 wt %, wherein the silk mat has a thickness of about 20-30 microns.

10. The electrospun silk mat of claim 9, wherein the content of silk fibroin protein in the electrospun silk mat ranges from about 75 wt % to about 90 wt %.

11. The electrospun silk mat of claim 9, further comprising upto 50 wt % of a polyethylene oxide (PEO) in the electrospun silk mat.

12. The electrospun silk mat of claim 11, wherein the electrospun silk mat comprises PEO in an amount from about 10 wt % to about 25 wt %.

13. The electrospun silk mat of claim 9, further comprising at least one active agent.

14. The electrospun silk mat of claim 13, wherein the active agent is a therapeutic agent or a biological material, selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and combinations thereof.

15. The electrospun silk mat of claim 9, wherein the silk mats have interconnected pores with a pore diameter averaging from about 0.1 to about 0.3 microns.

16. The electrospun silk mat claim 9, wherein the silk mat has a water absorption content of more than about 460%.

17. The electrospun silk mat of claim 14, wherein the active agent is a cell selected from the group consisting of progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, precursor cells, and combinations thereof.

18. The electrospun silk mat of claim 14, wherein the silk mat further comprises a cell growth media.

19. The electrospun silk mat of claim 14, wherein the active agent is an antibiotic.

20. A method of promoting wound healing comprising contacting a wound with at least one electrospun silk mat comprising a silk fibroin protein and, optionally, at least one active agent;

wherein the silk fibroin protein ranges from about 50 wt % to about 90 wt %, wherein the silk mat has a thickness of about 20 microns to about 30 microns;

wherein the silk mat has a water absorption content of more than about 460%, or equilibrium water content more than about 82%; and wherein the resulting silk mat has an oxygen transmission rate of more than about 15460 $cm^3/m^2/day$.

21. The method of claim 20, wherein the silk fibroin protein ranges from about 75 wt % to about 90 wt %.

22. A method of promoting wound healing comprising contacting a wound with at least one electrospun silk mat of claim 9.

\* \* \* \* \*